United States Patent
El Sayed et al.

(10) Patent No.: US 9,115,145 B2
(45) Date of Patent: Aug. 25, 2015

(54) TOCOTRIENOL DERIVATIVES AND ASSOCIATED METHODS

(71) Applicants: Khalid A. El Sayed, West Monroe, LA (US); Paul W. Sylvester, West Monroe, LA (US); Fathy A. Behery, Riyadh (SA)

(72) Inventors: Khalid A. El Sayed, West Monroe, LA (US); Paul W. Sylvester, West Monroe, LA (US); Fathy A. Behery, Riyadh (SA)

(73) Assignee: FIRST TECH INTERNATIONAL LIMITED, Beijing (CN)

( * ) Notice: Subject to any disclaimer, the term of this patent is extended or adjusted under 35 U.S.C. 154(b) by 0 days.

(21) Appl. No.: 14/336,120

(22) Filed: Jul. 21, 2014

(65) Prior Publication Data

US 2014/0329808 A1  Nov. 6, 2014

Related U.S. Application Data

(62) Division of application No. 13/690,910, filed on Nov. 30, 2012, now Pat. No. 8,816,071.

(60) Provisional application No. 61/566,286, filed on Dec. 2, 2011.

(51) Int. Cl.
| | | |
|---|---|---|
| A01N 43/16 | (2006.01) | |
| A61K 31/35 | (2006.01) | |
| C07D 498/04 | (2006.01) | |
| C07D 311/72 | (2006.01) | |
| C07D 311/70 | (2006.01) | |

(52) U.S. Cl.
CPC ............ *C07D 498/04* (2013.01); *C07D 311/70* (2013.01); *C07D 311/72* (2013.01)

(58) Field of Classification Search
None
See application file for complete search history.

(56) References Cited

U.S. PATENT DOCUMENTS

| | | |
|---|---|---|
| 2002/0107207 A1 | 8/2002 | Sanders et al. |
| 2004/0126340 A1 | 7/2004 | Jo |
| 2005/0065099 A1 | 3/2005 | Walkinshaw et al. |
| 2005/0124688 A1 | 6/2005 | Couladouros et al. |
| 2010/0273869 A1 | 10/2010 | Sylvester et al. |
| 2010/0297262 A1 | 11/2010 | Basu et al. |
| 2011/0196030 A1 | 8/2011 | El Sayed et al. |

FOREIGN PATENT DOCUMENTS

| | | |
|---|---|---|
| WO | 2011001258 A1 | 1/2011 |
| WO | WO 2011001258 A1 * | 1/2011 |

OTHER PUBLICATIONS

Sylvester et al. (Journal of the American College of Nutrition, 2010, 29, 324S-333S).*

Suga, Akina, Inhibition of NO Production in LPS-stimulated Mouse Macrophage-like Cells by Benzo[b]cyclohept[e][1,4]oxazine and 2-Aminotropone Derivatives, In Vivo, 2009, 691-698, vol. 23.

Liebner, Falk et al., Confirmation by trapping, synthesis, and reactivity of 2,3-dehydro-N-methylmorpholine (DNMM), Tetrahedron, Sep. 26, 2007, 11817-11821, vol. 63, Elsevier, online.

J. G. Cannon Chapter Nineteen in Burger's Medicinal Chemistry and Drug Discovery, Fifth Edition, vol. I: Principles and Practice, Wiley-Interscience 1995, pp. 783-802, 784.

Sheng Wang. Novel hexacyclic camptothecin derivatives. Part 1: Synthesis and cytotoxicity of camptothecins with an A-ring fused 1,3-oxazine ring, Bioorganic & Medicinal Chemistry Letters 18 (2008) 4095-4097.

Paul Sylvester, The Value of Tocotrienols in the Prevention and Treatment of Cancer, Journal of the American College of Nutrition, vol. 29, No. 3, 324S-333S (2010) Published by the American College of Nutrition.

* cited by examiner

*Primary Examiner* — Dennis Heyer
*Assistant Examiner* — Daniel M Podgorski
(74) *Attorney, Agent, or Firm* — John B. Edel; Edel Patents LLC

(57) ABSTRACT

Compositions of matter including (R)-2,5,6,8-tetramethyl-8-((3E,7E)-4,8,12-trimethyltrideca-3,7,11-trienyl)-1,2,3,8,9,10-hexahydrochromeno[5,6-e][1,3]oxazine and (R)-2,6,8-trimethyl-8-((3E,7E)-4,8,12-trimethyltrideca-3,7,11-trienyl)-1,2,3,8,9,10-hexahydrochromeno[5,6-e][1,3] oxazine are disclosed herein. Further disclosed are methods of preparation of such compounds and the use of such compounds as anticancer agents.

19 Claims, 109 Drawing Sheets

| $^{13}$C-NMR Data of Compounds 3-6[a]: | | | $\delta_C$, mult. | |
| --- | --- | --- | --- | --- |
| Position | 3 | 4 | 5 | 6 |
| 2 | 74.5, C | 74.6, C | 74.5, C | 74.6, C |
| 2-CH₃ | 23.9, CH₃ | 23.9, CH₃ | 23.9, CH₃ | 23.9, CH₃ |
| 3 | 31.1, CH₂ | 31.0, CH₂ | 31.1, CH₂ | 31.1, CH₂ |
| 4 | 18.9, CH₂ | 19.1, CH₂ | 18.9, CH₂ | 19.0, CH₂ |
| 5 | 114.7, C | 115.3, C | 114.8, C | 114.8, C |
| 6 | 145.2, C | 146.0, C | 145.2, C | 145.2, C |
| 7 | 124.0, C | 113.3, C | 124.0, C | 124.1, C |
| 7-CH₃ | 11.4, CH₃ | --- | 11.5, CH₃ | 11.5, CH₃ |
| 8 | 123.0, C | 125.7, C | 123.1, C | 123.1, C |
| 8-CH₃ | 11.7, CH₃ | 16.0, CH₃ | 11.7, CH₃ | 11.8, CH₃ |
| 9 | 115.0, C | 117.9, C | 115.1, C | 115.2, C |
| 10 | 144.6, C | 145.9, C | 145.0, C | 145.1, C |
| 1' | 39.8, CH₂ | 39.7, CH₂ | 39.8, CH₂ | 39.8, CH₂ |
| 2' | 22.3, CH₂ | 22.2, CH₂ | 22.3, CH₂ | 22.3, CH₂ |
| 3' | 124.5, CH | 124.3, CH | 124.5, CH | 124.5, CH |
| 4' | 135.2, C | 135.2, C | 135.2, C | 135.2, C |
| 4'-CH₃ | 16.1, CH₃ | 16.1, CH₃ | 16.1, CH₃ | 16.1, CH₃ |
| 5' | 39.8, CH₂ | 39.7, CH₂ | 39.8, CH₂ | 39.8, CH₂ |
| 6' | 26.8, CH₂ | 26.8, CH₂ | 26.8, CH₂ | 26.9, CH₂ |
| 7' | 124.4, CH | 124.4, CH | 124.4, CH | 124.4, CH |
| 8' | 135.0, C | 135.0, C | 135.0, C | 135.1, C |
| 8'-CH₃ | 11.7, CH₃ | 16.1, CH₃ | 16.0, CH₃ | 16.0, CH₃ |
| 9' | 39.8, CH₂ | 39.7, CH₂ | 39.8, CH₂ | 39.8, CH₂ |
| 10' | 26.7, CH₂ | 26.7, CH₂ | 26.7, CH₂ | 26.7, CH₂ |
| 11' | 124.3, CH | 124.3, CH | 124.3, CH | 124.2, CH |
| 12' | 131.3, C | 131.3, C | 131.4, C | 131.4, C |
| 12'a-CH₃ | 17.8, CH₃ | 17.8, CH₃ | 17.8, CH₃ | 17.8, CH₃ |
| 12'b-CH₃ | 25.8, CH₃ | 25.8, CH₃ | 25.8, CH₃ | 25.8, CH₃ |
| 2" | 83.0, CH₂ | 83.0, CH₂ | 81.5, CH₂ | 81.7, CH₂ |
| 4" | 50.5, CH₂ | 50.3, CH₂ | 47.7, CH₂ | 47.9, CH₂ |

Fig. 1A

| $^{13}$C-NMR Data of Compounds 3-6[a] continued: | | | | $\delta_C$, mult. |
|---|---|---|---|---|
| Position | 3 | 4 | 5 | 6 |
| 5" | 40.4, CH$_3$ | 40.4, CH$_3$ | 55.1, CH$_2$ | 56.1, CH$_2$ |
| 6" | | | 135.7, CH | 138.7, C |
| 7" | | | 118.0, CH$_2$ | 129.0, CH |
| 8" | | | | 128.5, CH |
| 9" | | | | 127.3, CH |
| 10" | | | | 128.5, CH |
| 11" | | | | 129.0, CH |
| 12" | | | | |
| 13" | | | | |
| 14" | | | | |
| 15" | | | | |
| 16" | | | | |
| 17" | | | | |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 1B

| $^{13}$C-NMR Data of Compounds 7-10.$^a$ | | | | $\delta_C$, mult. |
| --- | --- | --- | --- | --- |
| Position | 7 | 8 | 9 | 10 |
| 2 | 74.5, C | 74.6, C | 74.6, C | 74.7, C |
| 2-CH$_3$ | 23.9, CH$_3$ | 23.9, CH$_3$ | 23.9, CH$_3$ | 23.9, CH$_3$ |
| 3 | 31.1, CH$_2$ | 31.0, CH$_2$ | 31.0, CH$_2$ | 31.0, CH$_2$ |
| 4 | 19.0, CH$_2$ | 19.2, CH$_2$ | 19.0, CH$_2$ | 19.1, CH$_2$ |
| 5 | 114.6, C | 116.7, C | 114.6, C | 115.2, C |
| 6 | 145.9, C | 147.7, C | 145.3, C | 146.3, C |
| 7 | 123.8, C | 116.4, CH | 124.3, C | 116.4, CH |
| 7-CH$_3$ | 11.5, CH$_3$ | | 11.5, CH$_3$ | |
| 8 | 123.1, C | 125.5, C | 123.3, C | 126.0, C |
| 8-CH$_3$ | 11.7, CH$_3$ | 15.9, CH$_3$ | 11.7, CH$_3$ | 15.9, CH$_3$ |
| 9 | 116.1, C | 117.5, C | 114.9, C | 117.8, C |
| 10 | 145.0, C | 147.3, C | 145.0, C | 146.0, C |
| 1' | 39.8, CH$_2$ | 39.7, CH$_2$ | 39.8, CH$_2$ | 39.6, CH$_2$ |
| 2' | 22.3, CH$_2$ | 22.2, CH$_2$ | 22.3, CH$_2$ | 22.2, CH$_2$ |
| 3' | 124.5, CH | 124.5, CH | 124.5, CH | 124.5, CH |
| 4' | 135.2, C | 135.3, C | 135.2, C | 135.3, C |
| 4'-CH$_3$ | 16.1, CH$_3$ | 16.1, CH$_3$ | 16.1, CH$_3$ | 16.1, CH$_3$ |
| 5' | 39.8, CH$_2$ | 39.8, CH$_2$ | 39.8, CH$_2$ | 39.8, CH$_2$ |
| 6' | 26.9, CH$_2$ | 26.9, CH$_2$ | 26.8, CH$_2$ | 26.8, CH$_2$ |
| 7' | 124.4, CH | 124.4, CH | 124.4, CH | 124.3, CH |
| 8' | 135.1, C | 135.1, C | 135.1, C | 135.1, C |
| 8'-CH$_3$ | 16.0, CH$_3$ | 16.0, CH$_3$ | 16.0, CH$_3$ | 16.0, CH$_3$ |
| 9' | 39.8, CH$_2$ | 39.8, CH$_2$ | 39.8, CH$_2$ | 39.8, CH$_2$ |
| 10' | 26.7, CH$_2$ | 26.7, CH$_2$ | 26.7, CH$_2$ | 26.7, CH$_2$ |
| 11' | 124.3, CH | 124.3, CH | 124.3, CH | 124.2, CH |
| 12' | 131.4, C | 131.3, C | 131.4, C | 131.4, C |
| 12'a-CH$_3$ | 17.9, CH$_3$ | 17.8, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.8, CH$_3$ |
| 2''' | 79.9, CH$_2$ | 80.8, CH$_2$ | 81.9, CH$_2$ | 81.9, CH$_2$ |

Fig. 2A

| $^{13}$C-NMR Data of Compounds 7-10.[a] continued | | | | δC, mult. |
|---|---|---|---|---|
| Position | 7 | 8 | 9 | 10 |
| 4" | 45.1, CH2 | 44.8, CH2 | 48.1, CH2 | 47.9, CH2 |
| 5" | 57.7, CH | 57.6, CH | 59.2, CH2 | 53.9, CH2 |
| 6" | 30.9, CH2 | 30.9, CH2 | 54.0, CH2 | 59.2, CH2 |
| 7" | 53.0, CH2 | 53.0, CH2 | | |
| 8" | | | | |
| 9" | 53.0, CH2 | 53.0, CH2 | | |
| 10" | 30.9, CH2 | 30.9, CH2 | | |
| 11" | 63.2, CH2 | 63.1, CH2 | | |
| 12" | 138.4, C | 138.3, C | | |
| 13" | 129.3, CH | 129.3, CH | | |
| 14" | 128.2, CH | 128.3, CH | | |
| 15" | 127.1, CH | 127.1, CH | | |
| 16" | 128.2, CH | 128.3, CH | | |
| 17" | 129.3, CH | 129.3, CH | | |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 2B

| $^{13}$C-NMR Data of Compounds 11-14.[a] | | | | $\delta_C$, mult. |
|---|---|---|---|---|
| Position | 11 | 12 | 13 | 14 |
| 2 | 75.6, C | 74.2, C | 74.2, C | 74.5, C |
| 2-CH$_3$ | 24.2, CH$_3$ | 23.7, CH$_3$ | 23.7, CH$_3$ | 23.9, CH$_3$ |
| 3 | 31.3, CH$_2$ | 31.7, CH$_2$ | 31.5, CH$_2$ | 31.1, CH$_2$ |
| 4 | 22.3, CH$_2$ | 20.5, CH$_2$ | 20.6, CH$_2$ | 18.9, CH$_2$ |
| 5 | 113.7, CH | 115.1, C | 116.3, C | 114.9, C |
| 6 | 146.4, C | 148.8, C | 150.3, C | 145.1, C |
| 7 | 123.4, C | 125.1, C | 117.0, CH | 124.0, C |
| 7-CH$_3$ | | 11.8, CH$_3$ | | 11.4, CH$_3$ |
| 8 | 120.5, C | 123.2, C | 127.1, C | 123.0, C |
| 8-CH$_3$ | 10.5, CH$_3$ | 12.0, CH$_3$ | 15.9, CH$_3$ | 11.7, CH$_3$ |
| 9 | 116.9, C | 116.2, C | 119.0, C | 115.0, C |
| 10 | 146.0, C | 144.4, C | 145.1, C | 145.1, C |
| 1' | 39.9, CH$_2$ | 39.7, CH$_2$ | 39.7, CH$_2$ | 39.8, CH$_2$ |
| 2' | 22.4, CH$_2$ | 22.3, CH$_2$ | 22.2, CH$_2$ | 22.3, CH$_2$ |
| 3' | 124.5, CH | 124.5, CH | 124.5, CH | 124.5, CH |
| 4' | 135.3, C | 135.2, C | 135.2, C | 135.2, C |
| 4'-CH$_3$ | 16.1, CH$_3$ | 16.1, CH$_3$ | 16.2, CH$_3$ | 16.1, CH$_3$ |
| 5' | 39.8, CH$_2$ | 39.8, CH$_2$ | 39.8, CH$_2$ | 39.8, CH$_2$ |
| 6' | 26.8, CH$_2$ | 26.8, CH$_2$ | 26.8, CH$_2$ | 26.8, CH$_2$ |
| 7' | 124.3, CH | 124.4, CH | 124.4, CH | 124.4, CH |
| 8' | 135.1, C | 135.0, C | 135.1, C | 135.0, C |
| 8'-CH$_3$ | 16.0, CH$_3$ | 16.0, CH$_3$ | 16.1, CH$_3$ | 16.0, CH$_3$ |
| 9' | 39.8, CH$_2$ | 39.8, CH$_2$ | 39.8, CH$_2$ | 39.8, CH$_2$ |
| 10' | 26.7, CH$_2$ | 26.7, CH$_2$ | 26.7, CH$_2$ | 26.7, CH$_2$ |
| 11' | 124.2, CH | 124.3, CH | 124.3, CH | 124.3, CH |
| 12' | 131.4, C | 131.3, C | 131.4, C | 131.3, C |
| 12'a-CH$_3$ | 17.8, CH$_3$ | 17.8, CH$_3$ | 17.8, CH$_3$ | 17.7, CH$_3$ |
| 12'b-CH$_3$ | 25.8, CH$_3$ | 25.8, CH$_3$ | 25.8, CH$_3$ | 25.7, CH$_3$ |
| 2" | 81.6, CH$_2$ | 83.3, CH$_2$ | 83.4, CH$_2$ | 81.8, CH$_2$ |
| 4" | 48.7, CH$_2$ | 49.4, CH$_2$ | 49.2, CH$_2$ | 48.6, CH$_2$ |
| 5" | 53.9, CH$_2$ | 49.1, CH$_2$ | 49.1, CH$_2$ | 47.8, CH$_2$ |
| 6" | 58.9, CH$_2$ | 27.9, CH$_2$ | 28.6, CH$_2$ | 32.6, CH$_2$ |
| 7" | | 68.0, CH$_2$ | 68.0, CH$_2$ | 101.3, CH |
| 8" | | | | 61.2, CH$_2$ |
| 9" | | | | 15.4, CH$_3$ |
| 10" | | | | 61.2, CH$_2$ |
| 11" | | | | 15.4, CH$_3$ |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 3

| $^{13}$C-NMR Data of Compounds 15-18[a]. | | | | $\delta_C$, mult. |
|---|---|---|---|---|
| Position | 15 | 16 | 17 | 18 |
| 2 | 74.7, C | 74.5, C | 74.5, C | 74.6, C |
| 2-CH$_3$ | 23.9, CH$_3$ | 23.8, CH$_3$ | 23.9, CH$_3$ | 23.9, CH$_3$ |
| 3 | 30.9, CH$_2$ | 31.7, CH$_2$ | 31.1, CH$_2$ | 30.9, CH$_2$ |
| 4 | 19.1, CH$_2$ | 19.0, CH$_2$ | 19.0, CH$_2$ | 19.1, CH$_2$ |
| 5 | 117.9, C | 115.0, C | 114.9, C | 115.2, C |
| 6 | 145.9, C | 149.1, C | 145.2, C | 146.3, C |
| 7 | 116.3, CH | 124.8, C | 124.0, C | 116.2, CH |
| 7-CH$_3$ | | 11.8, CH$_3$ | 11.5, CH$_3$ | |
| 8 | 125.9, C | 124.0, C | 123.0, C | 125.8, C |
| 8-CH$_3$ | 15.9, CH$_3$ | 12.0, CH$_3$ | 11.7, CH$_3$ | 15.9, CH$_3$ |
| 9 | 117.9, C | 115.9, C | 115.0, C | 117.8, C |
| 10 | 145.9, C | 145.1, C | 145.1, C | 145.9, C |
| 1' | 39.7, CH$_2$ | 39.8, CH$_2$ | 39.8, CH$_2$ | 39.7, CH$_2$ |
| 2' | 22.2, CH$_2$ | 22.3, CH$_2$ | 22.3, CH$_2$ | 22.2, CH$_2$ |
| 3' | 124.5, CH | 124.5, CH | 124.5, CH | 124.4, CH |
| 4' | 135.3, C | 135.2, C | 135.2, C | 135.2, C |
| 4'-CH$_3$ | 16.1, CH$_3$ | 16.1, CH$_3$ | 16.1, CH$_3$ | 16.1, CH$_3$ |
| 5' | 39.8, CH$_2$ | 39.8, CH$_2$ | 39.8, CH$_2$ | 39.7, CH$_2$ |
| 6' | 26.8, CH$_2$ | 26.8, CH$_2$ | 26.8, CH$_2$ | 26.8, CH$_2$ |
| 7' | 124.3, CH | 124.4, CH | 124.4, CH | 124.3, CH |
| 8' | 135.1, C | 135.0, C | 135.1, C | 135.0, C |
| 8'-CH$_3$ | 16.0, CH$_3$ | 16.0, CH$_3$ | 16.0, CH$_3$ | 16.0, CH$_3$ |
| 9' | 39.8, CH$_2$ | 39.8, CH$_2$ | 39.8, CH$_2$ | 39.7, CH$_2$ |
| 10' | 26.7, CH$_2$ | 26.7, CH$_2$ | 26.7, CH$_2$ | 26.6, CH$_2$ |
| 11' | 124.2, CH | 124.3, CH | 124.3, CH | 124.2, CH |
| 12' | 131.4, C | 131.4, C | 131.3, C | 131.3, C |
| 12'a-CH$_3$ | 17.8, CH$_3$ | 17.8, CH$_3$ | 17.8, CH$_3$ | 17.7, CH$_3$ |
| 12'b-CH$_3$ | 25.8, CH$_3$ | 25.8, CH$_3$ | 25.8, CH$_3$ | 25.7, CH$_3$ |
| 2" | 81.3, CH$_2$ | 82.2, CH$_2$ | 81.6, CH$_2$ | 81.3, CH$_2$ |
| 4" | 48.4, CH$_2$ | 49.3, CH$_2$ | 48.6, CH$_2$ | 48.4, CH$_2$ |
| 5" | 47.7, CH$_2$ | 53.2, CH$_2$ | 51.9, CH$_2$ | 51.7, CH$_2$ |
| 6" | 29.8, CH$_2$ | 34.6, CH$_2$ | 32.6, CH$_2$ | 32.5, CH$_2$ |
| 7" | 101.2, CH | 31.1, CH$_2$ | 23.5, CH$_2$ | 23.4, CH$_2$ |
| 8" | 61.4, CH$_2$ | 56.9, CH$_2$ | 27.9, CH$_2$ | 27.7, CH$_2$ |
| 9" | 15.4, CH$_3$ | | 62.9, CH$_2$ | 62.7, CH$_2$ |
| 10" | 61.4, CH$_2$ | 56.9, CH$_2$ | | |
| 11" | 15.4, CH$_3$ | 31.1, CH$_2$ | | |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 4

| $^{13}$C-NMR Data of Compounds 19-22.$^a$ $\delta_C$, mult. | | | | |
|---|---|---|---|---|
| Position | 19 | 20 | 21 | 22 |
| 2 | 74.6, C | 74.8, C | 74.6, C | 74.7, C |
| 2-CH$_3$ | 23.8, CH$_3$ | 23.9, CH$_3$ | 23.8, CH$_3$ | 23.9, CH$_3$ |
| 3 | 31.0, CH$_2$ | 30.9, CH$_2$ | 31.1, CH$_2$ | 30.9, CH$_2$ |
| 4 | 18.9, CH$_2$ | 19.1, CH$_2$ | 19.0, CH$_2$ | 19.1, CH$_2$ |
| 5 | 114.1, C | 114.4, C | 114.5, C | 115.1, C |
| 6 | 145.4, C | 146.3, C | 145.3, C | 146.1, C |
| 7 | 123.1, C | 116.3, CH | 124.1, C | 116.2, CH |
| 7-CH$_3$ | 11.5, CH$_3$ | | 11.5, CH$_3$ | |
| 8 | 123.1, C | 126.2, C | 123.1, C | 125.8, C |
| 8-CH$_3$ | 11.7, CH$_3$ | 16.0, CH$_3$ | 11.7, CH$_3$ | 16.0, CH$_3$ |
| 9 | 115.1, C | 118.0, C | 115.0, C | 117.9, C |
| 10 | 144.6, C | 145.8, C | 144.8, C | 146.0, C |
| 1' | 39.8, CH$_2$ | 39.7, CH$_2$ | 39.8, CH$_2$ | 39.8, CH$_2$ |
| 2' | 22.3, CH$_2$ | 22.2, CH$_2$ | 22.3, CH$_2$ | 22.2, CH$_2$ |
| 3' | 124.5, CH | 124.5, CH | 124.5, CH | 124.5, CH |
| 4' | 135.2, C | 135.3, C | 135.2, C | 135.2, C |
| 4'-CH$_3$ | 16.1, CH$_3$ | 16.1, CH$_3$ | 16.1, CH$_3$ | 16.1, CH$_3$ |
| 5' | 39.8, CH$_2$ | 39.7, CH$_2$ | 39.8, CH$_2$ | 39.8, CH$_2$ |
| 6' | 26.8, CH$_2$ | 26.8, CH$_2$ | 26.8, CH$_2$ | 26.8, CH$_2$ |
| 7' | 124.4, CH | 124.3, CH | 124.4, CH | 124.4, CH |
| 8' | 135.1, C | 135.1, C | 135.0, C | 135.0, C |
| 8'-CH$_3$ | 16.0, CH$_3$ | 16.1, CH$_3$ | 16.0, CH$_3$ | 16.1, CH$_3$ |
| 9' | 39.8, CH$_2$ | 39.7, CH$_2$ | 39.8, CH$_2$ | 39.8, CH$_2$ |

Fig. 5A

| $^{13}$C-NMR Data of Compounds 19-22.$^a$ Continued $\delta_C$, mult. | | | | |
|---|---|---|---|---|
| Position | 19 | 20 | 21 | 22 |
| 10' | 26.7, CH$_2$ | 26.7, CH$_2$ | 26.7, CH$_2$ | 26.7, CH$_2$ |
| 11' | 124.3, CH | 124.2, CH | 124.3, CH | 124.3, CH |
| 12' | 131.3, C | 131.4, C | 131.3, C | 131.3, C |
| 12'a-CH$_3$ | 17.8, CH$_3$ | 17.8, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.7, CH$_3$ |
| 2" | 80.7, CH$_2$ | 80.2, CH$_2$ | 81.0, CH$_2$ | 80.8, CH$_2$ |
| 4" | 48.3, CH$_2$ | 48.1, CH$_2$ | 48.4, CH$_2$ | 48.2, CH$_2$ |
| 5" | 51.1, CH$_2$ | 51.0, CH$_2$ | 51.5, CH$_2$ | 51.4, CH$_2$ |
| 6" | 22.8, CH$_2$ | 22.7, CH$_2$ | 26.8, CH$_2$ | 26.8, CH$_2$ |
| 7" | 29.8, CH$_2$ | 26.6, CH$_2$ | 24.7, CH$_2$ | 24.7, CH$_2$ |
| 8" | 34.0, CH$_2$ | 34.0, CH$_2$ | 27.5, CH$_2$ | 27.4, CH$_2$ |
| 9" | 176.8, C | 177.5, C | 34.1, CH$_2$ | 34.1, CH$_2$ |
| 10" | | | 178.6, C | 178.4, C |
| 11" | | | | |
| 12" | | | | |
| 13" | | | | |
| 14" | | | | |

$^a$ In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 5B

| $^{13}$C-NMR Data of Compounds 23-26.$^a$ $\delta_C$, mult. | | | | |
|---|---|---|---|---|
| Position | 23 | 24 | 25 | 26 |
| 2 | 74.5, C | 74.7, C | 74.7, C | 74.6, C |
| 2-CH$_3$ | 23.8, CH$_3$ | 23.9, CH$_3$ | 23.9, CH$_3$ | 23.9, CH$_3$ |
| 3 | 31.1, CH$_2$ | 30.9, CH$_2$ | 30.9, CH$_2$ | 31.1, CH$_2$ |
| 4 | 19.0, CH$_2$ | 19.1, CH$_2$ | 19.1, CH$_2$ | 18.9, CH$_2$ |
| 5 | 115.0, C | 115.1, C | 115.1, C | 114.8, C |
| 6 | 145.2, C | 146.3, C | 146.3, C | 145.2, C |
| 7 | 124.0, C | 116.4, CH | 116.4, CH | 124.0, C |
| 7-CH$_3$ | 11.5, CH$_3$ | | | 11.5, CH$_3$ |
| 8 | 123.1, C | 126.0, C | 126.0, C | 123.1, C |
| 8-CH$_3$ | 11.7, CH$_3$ | 16.0, CH$_3$ | 16.0, CH$_3$ | 11.7, CH$_3$ |
| 9 | 115.0, C | 117.9, C | 117.9, C | 115.0, C |
| 10 | 145.2, C | 146.0, C | 146.0, C | 145.1, C |
| 1' | 39.8, CH$_2$ | 39.1, CH$_2$ | 39.1, CH$_2$ | 39.2, CH$_2$ |
| 2' | 22.3, CH$_2$ | 22.2, CH$_2$ | 22.2, CH$_2$ | 22.3, CH$_2$ |
| 3' | 124.5, CH | 124.5, CH | 124.5, CH | 124.5, CH |
| 4' | 135.2, C | 135.3, C | 135.3, C | 135.2, C |
| 4'-CH$_3$ | 16.1, CH$_3$ | 16.1, CH$_3$ | 16.1, CH$_3$ | 16.1, CH$_3$ |
| 5' | 39.8, CH$_2$ | 39.8, CH$_2$ | 39.8, CH$_2$ | 39.2, CH$_2$ |
| 6' | 26.8, CH$_2$ | 26.8, CH$_2$ | 26.8, CH$_2$ | 26.8, CH$_2$ |
| 7' | 124.4, CH | 124.3, CH | 124.3, CH | 124.4, CH |
| 8' | 135.1, C | 135.1, C | 135.1, C | 135.1, C |
| 8'-CH$_3$ | 16.0, CH$_3$ | 16.1, CH$_3$ | 16.1, CH$_3$ | 16.0, CH$_3$ |
| 9' | 39.8, CH$_2$ | 39.8, CH$_2$ | 39.8, CH$_2$ | 39.2, CH$_2$ |
| 10' | 26.7, CH$_2$ | 26.7, CH$_2$ | 26.7, CH$_2$ | 26.7, CH$_2$ |

Fig. 6A

| $^{13}$C-NMR Data of Compounds 23-26.[a] Continued $\delta_C$, mult. | | | | |
|---|---|---|---|---|
| Position | 23 | 24 | 25 | 26 |
| 11' | 124.3, CH | 124.2, CH | 124.2, CH | 124.3, CH |
| 12' | 131.4, C | 131.4, C | 131.4, C | 132.1, C |
| 12'a-CH$_3$ | 17.8, CH$_3$ | 17.8, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.8, CH$_3$ |
| 2" | 81.7, CH$_2$ | 81.2, CH$_2$ | 81.2, CH$_2$ | 81.5, CH$_2$ |
| 4" | 48.8, CH$_2$ | 48.7, CH$_2$ | 48.7, CH$_2$ | 48.8, CH$_2$ |
| 5" | 53.8, CH$_2$ | 53.6, CH$_2$ | 53.6, CH$_2$ | 53.9, CH$_2$ |
| 6" | 34.8, CH$_2$ | 34.5, CH$_2$ | 34.5, CH$_2$ | 34.0, CH$_2$ |
| 7" | 132.7, C | 132.3, C | 132.3, C | 131.3, C |
| 8" | 112.0, CH | 112.0, CH | 112.0, CH | 129.8, CH |
| 9" | 148.9, C | 148.9, C | 148.9, C | 115.3, CH |
| 10" | 147.5, C | 147.5, C | 147.5, C | 154.1, C |
| 11" | 111.3, CH | 111.3, CH | 111.3, CH | 115.3, CH |
| 12" | 120.6, CH | 120.6, CH | 120.6, CH | 129.8, CH |
| 13" | 56.0, CH$_3$ | 56.0, CH$_3$ | 56.0, CH$_3$ | |
| 14" | 56.0, CH$_3$ | 56.0, CH$_3$ | 56.0, CH$_3$ | | a In CDCl3, 100 MHz for 13C-NMR. Carbon multiplicities were determined by APT experiments, C = quaternary, CH = methine, CH2 = methylene, CH3 = methyl carbons.

Fig. 6B

| $^{13}$C-NMR Data of Compounds 27-30.[a] | | | $\delta_C$, mult. | |
|---|---|---|---|---|
| Position | 27 | 28 | 29 | 30 |
| 2 | 74.7, C | 74.6, C | 74.7, C | 74.1, C |
| 2-CH$_3$ | 23.9, CH$_3$ | 23.8, CH$_3$ | 23.9, CH$_3$ | 23.7, CH$_3$ |
| 3 | 30.9, CH$_2$ | 31.0, CH$_2$ | 30.9, CH$_2$ | 31.6, CH$_2$ |
| 4 | 19.1, CH$_2$ | 18.9, CH$_2$ | 19.1, CH$_2$ | 20.4, CH$_2$ |
| 5 | 114.9, C | 114.3, C | 115.0, C | 115.5, C |
| 6 | 146.1, C | 145.4, C | 146.3, C | 147.7, C |
| 7 | 116.3, CH | 123.2, C | 116.4, CH | 123.0, C |
| 7-CH$_3$ |  | 11.5, CH$_3$ | ---- | 11.8, CH$_3$ |
| 8 | 126.0, C | 123.2, C | 126.1, C | 124.9, C |
| 8-CH$_3$ | 15.9, CH$_3$ | 11.7, CH$_3$ | 14.2, CH$_3$ | 12.0, CH$_3$ |
| 9 | 117.9, C | 115.1, C | 118.0, C | 116.2, C |
| 10 | 146.1, C | 144.9, C | 146.0, C | 144.2, C |
| 1' | 39.8, CH$_2$ | 39.8, CH$_2$ | 39.7, CH$_2$ | 39.8, CH$_2$ |
| 2' | 22.2, CH$_2$ | 22.2, CH$_2$ | 22.2, CH$_2$ | 22.3, CH$_2$ |
| 3' | 124.5, CH | 124.5, CH | 124.6, CH | 124.4, CH |
| 4' | 135.3, C | 135.2, C | 135.3, C | 135.2, C |
| 4'-CH$_3$ | 16.1, CH$_3$ | 16.1, CH$_3$ | 16.1, CH$_3$ | 16.1, CH$_3$ |
| 5' | 39.8, CH$_2$ | 39.8, CH$_2$ | 39.7, CH$_2$ | 39.8, CH$_2$ |
| 6' | 26.8, CH$_2$ | 26.8, CH$_2$ | 26.8, CH$_2$ | 26.8, CH$_2$ |
| 7' | 124.3, CH | 124.4, CH | 124.3, CH | 124.3, CH |
| 8' | 135.1, C | 135.1, C | 135.1, C | 135.0, C |
| 8'-CH$_3$ | 16.0, CH$_3$ | 16.0, CH$_3$ | 16.0, CH$_3$ | 16.0, CH$_3$ |
| 9' | 39.8, CH$_2$ | 39.8, CH$_2$ | 39.7, CH$_2$ | 39.8, CH$_2$ |
| 10' | 26.7, CH$_2$ | 26.7, CH$_2$ | 26.7, CH$_2$ | 26.7, CH$_2$ |

Fig. 7A

| $^{13}$C-NMR Data of Compounds 27-30.$^a$ Continued | | | | $\delta_C$, mult. |
|---|---|---|---|---|
| Position | 27 | 28 | 29 | 30 |
| 11' | 124.3, CH | 124.3, CH | 124.2, CH | 124.3, CH |
| 12' | 131.4, C | 131.1, C | 131.4, C | 131.4, C |
| 12'a-CH$_3$ | 17.8, CH$_3$ | 17.8, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.8, CH$_3$ |
| 1" | | | | 47.6, CH$_2$ |
| 2" | 81.1, CH$_2$ | 81.7, CH$_2$ | 81.6, CH$_2$ | |
| 3" | | | | 50.0, CH$_2$ |
| 4" | 48.6, CH$_2$ | 48.1, CH$_2$ | 48.0, CH$_2$ | 35.6, CH$_2$ |
| 5" | 53.7, CH$_2$ | 55.4, CH$_2$ | 55.3, CH$_2$ | 131.8, C |
| 6" | 33.7, CH$_2$ | 141.3, C | 141.1, C | 111.9, CH |
| 7" | 131.5, C | 123.6, CH | 123.6, CH | 149.3, C |
| 8" | 129.8, CH | 148.7, C | 148.6, C | 149.1, C |
| 9" | 115.4, CH | 122.4, CH | 122.5, CH | 111.4, CH |
| 10" | 154.3, C | 129.4, CH | 129.4, CH | 120.7, CH |
| 11" | 115.4, CH | 134.8, CH | 134.8, CH | 56.0, CH$_3$* |
| 12" | 129.8, CH | | | 55.9, CH$_3$* |

$^a$ In CDCl$_3$, 100 MHz for $^{13}$C-NMR. Carbon multiplicities were determined by APT experiments, C = quaternary, CH = methine, CH$_2$ = methylene, CH$_3$ = methyl carbons. * Ambiguous.

Fig. 7B

| $^{13}$C-NMR Data of Compounds 31-34.[a] | | | | $\delta_C$, mult. |
|---|---|---|---|---|
| Position | 31 | 32 | 33 | 34 |
| 2 | 74.2, C | 74.4, C | 74.5, C | 75.5, C |
| 2-CH₃ | 23.7, CH₃ | 23.8, CH₃ | 23.8, CH₃ | 24.1, CH₃ |
| 3 | 31.6, CH₂ | 31.5, CH₂ | 31.4, CH₂ | 31.3, CH₂ |
| 4 | 20.4, CH₂ | 19.9, CH₂ | 19.9, CH₂ | 22.3, CH₂ |
| 5 | 116.2, C | 115.2, C | 118.3, C | 113.7, CH |
| 6 | 149.0, C | 147.4, C | 148.3, C | 148.8, C |
| 7 | 125.0, C | 125.9, C | 116.8, CH | 124.1, C |
| 7-CH₃ | 11.9, CH₃ | 11.5, CH₃ | | |
| 8 | 123.1, C | 123.1, C | 127.3, C | 122.3, C |
| 8-CH₃ | 12.0, CH₃ | 12.0, CH₃ | 15.9, CH₃ | 11.2, CH₃ |
| 9 | 116.2, C | 118.8, C | 119.9, C | 121.3, C |
| 10 | 144.3, C | 144.9, C | 145.5, C | 145.3, C |
| 1' | 39.7, CH₂ | 39.5, CH₂ | 39.5, CH₂ | 39.8, CH₂ |
| 2' | 22.3, CH₂ | 22.3, CH₂ | 22.2, CH₂ | 22.5, CH₂ |
| 3' | 124.5, CH | 124.5, CH | 124.5, CH | 124.5, CH |
| 4' | 135.2, C | 135.2, C | 135.3, C | 135.2, C |
| 4'-CH₃ | 16.1, CH₃ | 16.0, CH₃ | 16.2, CH₃ | 16.0, CH₃ |
| 5' | 39.7, CH₂ | 39.8, CH₂ | 39.8, CH₂ | 39.8, CH₂ |
| 6' | 26.8, CH₂ | 26.8, CH₂ | 26.8, CH₂ | 26.8, CH₂ |
| 7' | 124.4, CH | 124.4, CH | 124.3, CH | 124.3, CH |
| 8' | 135.1, C | 135.1, C | 135.1, C | 135.1, C |
| 8'-CH₃ | 16.0, CH₃ | 15.9, CH₃ | 16.1, CH₃ | 15.9, CH₃ |
| 9' | 39.7, CH₂ | 39.8, CH₂ | 39.8, CH₂ | 39.8, CH₂ |
| 10' | 26.7, CH₂ | 26.7, CH₂ | 26.7, CH₂ | 26.7, CH₂ |
| 11' | 124.3, CH | 124.3, CH | 124.3, CH | 124.2, CH |
| 12' | 131.4, C | 131.3, C | 131.4, C | 131.4, C |

Fig. 8A

| $^{13}$C-NMR Data of Compounds 31-34.[a] Continued | | | | $\delta_C$, mult. |
|---|---|---|---|---|
| Position | 31 | 32 | 33 | 34 |
| 12'a-CH$_3$ | 17.8, CH$_3$ | 17.5, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.8, CH$_3$ |
| 1" | 47.4, CH$_2$ | 60.1, CH$_2$ | 59.6, CH$_2$ | 60.6, CH$_2$ |
| 2" | | | | |
| 3" | 49.9, CH$_2$ | | | |
| 4" | 34.9, CH$_2$ | | | |
| 5" | 130.8, C | | | |
| 6" | 129.9, CH | | | |
| 7" | 115.6, CH | | | |
| 8" | 154.6, C | | | |
| 9" | 115.6, CH | | | |
| 10" | 129.9, CH | | | |
| 11" | | | | |
| 12" | | | | |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons.

Fig. 8B

| ¹³C-NMR Data of Compounds 35-40.ᵃ | | | | | $\delta_C$, mult. | |
|---|---|---|---|---|---|---|
| Position | 35 | 36 | 37 | 38 | 39 | 40 |
| 2 | 74.6, C | 74.7, C | 74.5, C | 74.6, C | 74.5, C | 74.6, C |
| 2-CH₃ | 23.9, CH₃ | 23.9, CH₃ | 23.9, CH₃ | 23.9, CH₃ | 23.9, CH₃ | 32.9, CH₃ |
| 3 | 31.8, CH₂ | 31.6, CH₂ | 31.1, CH₂ | 31.0, CH₂ | 31.1, CH₂ | 31.0, CH₂ |
| 4 | 19.0, CH₂ | 19.1, CH₂ | 19.0, CH₂ | 19.1, CH₂ | 19.0, CH₂ | 19.1, CH₂ |
| 5 | 114.3, C | 115.0, C | 114.9, C | 115.6, C | 115, C | 115.6, C |
| 6 | 145.4, C | 146.6, C | 145.1, C | 146.5, C | 145.1, C | 146.5, C |
| 7 | 115.0, C | 116.3, CH | 115.0, C | 116.2, CH | 115.0, C | 116.2, CH |
| 7-CH₃ | 11.5, CH₃ | | 11.5, CH₃ | | 11.5, CH₃ | |
| 8 | 124.5, C | 126.0, C | 124.0, C | 125.7, C | 123.9, C | 125.7, C |
| 8-CH₃ | 11.7, CH₃ | 16.0, CH₃ | 11.7, CH₃ | 16.0, CH₃ | 11.7, CH₃ | 16.0, CH₃ |
| 9 | 123.1, C | 117.9, C | 123.0, C | 117.9, C | 123.0, C | 117.9, C |
| 10 | 144.8, C | 146.0, C | 145.1, C | 145.8, C | 145.1, C | 145.8, C |
| 1' | 39.8, CH₂ | 39.7, CH₂ | 39.8, CH₂ | 39.7, CH₂ | 39.8, CH₂ | 39.7, CH₂ |
| 2' | 22.3, CH₂ | 22.2, CH₂ | 22.3, CH₂ | 22.2, CH₂ | 22.3, CH₂ | 22.2, CH₂ |
| 3' | 124.5, CH | 124.5, CH | 124.5, CH | 124.5, CH | 124.5, CH | 124.5, CH |
| 4' | 135.2, C | 135.3, C | 135.2, C | 135.2, C | 135.2, C | 135.2, C |
| 4'-CH₃ | 16.1, CH₃ | 16.1, CH₃ | 16.1, CH₃ | 16.1, CH₃ | 16.1, CH₃ | 16.1, CH₃ |
| 5' | 39.8, CH₂ | 39.7, CH₂ | 39.8, CH₂ | 39.7, CH₂ | 39.8, CH₂ | 39.7, CH₂ |
| 6' | 26.8, CH₂ | 26.8, CH₂ | 26.8, CH₂ | 26.8, CH₂ | 26.8, CH₂ | 26.8, CH₂ |
| 7' | 124.4, CH | 124.3, CH | 124.4, CH | 124.4, CH | 124.4, CH | 124.4, CH |
| 8' | 135.1, C | 135.1, C | 135.1, C | 135.0, C | 135.0, C | 135.0, C |
| 8'-CH₃ | 16.0, CH₃ | 16.1, CH₃ | 16.0, CH₃ | 16.0, CH₃ | 16.0, CH₃ | 16.0, CH₃ |
| 9' | 39.8, CH₂ | 39.7, CH₂ | 39.8, CH₂ | 39.7, CH₂ | 39.8, CH₂ | 39.7, CH₂ |
| 10' | 26.7, CH₂ | 26.7, CH₂ | 26.7, CH₂ | 26.7, CH₂ | 26.7, CH₂ | 26.7, CH₂ |
| 11' | 124.3, CH | 124.2, CH | 124.3, CH | 124.3, CH | 124.3, CH | 124.3, CH |

Fig. 9A

| $^{13}$C-NMR Data of Compounds 35-40.[a] Continued | | | | | $\delta_C$, mult. | |
|---|---|---|---|---|---|---|
| Position | 35 | 36 | 37 | 38 | 39 | 40 |
| 12' | 131.3, C | 131.4, C | 131.4, C | 131.3, C | 131.3, C | 131.3, C |
| 12'a-CH$_3$ | 17.8, CH$_3$ | 17.8, CH$_3$ | 17.8, CH$_3$ | 17.8, CH$_3$ | 17.8, CH$_3$ | 17.8, CH$_3$ |
| 12'b-CH$_3$ | 25.8, CH$_3$ | 25.8, CH$_3$ | 25.8, CH$_3$ | 25.8, CH$_3$ | 25.8, CH$_3$ | 25.8, CH$_3$ |
| 2" | 81.1, CH$_2$ | 81.1, CH$_2$ | 81.6, CH$_2$ | 81.5, CH$_2$ | 81.7, CH$_2$ | 81.5, CH$_2$ |
| 4" | 48.2, CH$_2$ | 48.1, CH$_2$ | 48.6, CH$_2$ | 48.5, CH$_2$ | 48.6, CH$_2$ | 48.5, CH$_2$ |
| 5" | 51.8, CH$_2$ | 51.8, CH$_2$ | 51.9, CH$_2$ | 51.8, CH$_2$ | 52.1, CH$_2$ | 52.0, CH$_2$ |
| 6" | 25.7, CH$_2$ | 25.6, CH$_2$ | 28.2, CH$_2$ | 28.2, CH$_2$ | 28.3, CH$_2$ | 28.3, CH$_2$ |
| 7" | 31.0, CH$_2$ | 30.9, CH$_2$ | 25.7, CH$_2$ | 25.7, CH$_2$ | 27.3, CH$_2$ | 27.3, CH$_2$ |
| 8" | 62.9, CH$_2$ | 62.9, CH$_2$ | 27.1, CH$_2$ | 27.1, CH$_2$ | 29.5, CH$_2$ | 29.5, CH$_2$ |
| 9" | | | 32.8, CH$_2$ | 32.8, CH$_2$ | 29.6, CH$_2$ | 29.6, CH$_2$ |
| 10" | | | 63.0, CH$_2$ | 62.9, CH$_2$ | 25.8, CH$_2$ | 25.8, CH$_2$ |
| 11" | | | | | 32.9, CH$_2$ | 32.8, CH$_2$ |
| 12" | | | | | 63.1, CH$_2$ | 63.1, CH$_2$ |

[a] In CDCl$_3$, 100 MHz for $^{13}$C-NMR. Carbon multiplicities were determined by APT experiments, C = quaternary, CH = methine, CH$_2$ = methylene, CH$_3$ = methyl carbons. * Ambiguous.

Fig. 9B

| Position | \(^1\)H-NMR Data of Compounds 3-7\(^a\) $\delta_H$, mult., *J* | | | | |
|---|---|---|---|---|---|
| | 3 | 4 | 5 | 6 | 7 |
| 2-CH₃ | 1.24, s | 1.25, s | 1.24, s | 1.25, s | 1.25, s |
| 3 | 1.78, m | 1.78, m | 1.76, m | 1.77, m | 1.78, m |
| 4 | 2.44, m | 2.45, m | 2.43, m | 2.38, m | 2.47, m |
| 5 | | | | | |
| 7 | | 6.50, s | | | |
| 7-CH₃ | 2.10, s | | 2.11, s | 2.15, s | 2.10, s |
| 8-CH₃ | 2.10, s | 2.13, s | 2.10, s | 2.14, s | 2.07, s |
| 1' | 1.54, m | 1.55, m | 1.54, m | 1.54, m | 1.55, m |
| 2' | 2.07, m | 2.10, m | 2.13, m | 2.12, m | 2.12, m |
| 3' | 5.13, m | 5.10, m | 5.09, m | 5.14, m | 5.10, m |
| 4'-CH₃ | 1.59, s | 1.59, s | 1.60, s | 1.61, s | 1.60, s |
| 5' | 1.97, m | 1.97, m | 1.97, m | 2.07, m | 1.98, m |
| 6' | 2.05, m | 2.05, m | 2.05, m | 2.99, m | 2.05, m |
| 7' | 5.13, m | 5.10, m | 5.09, m | 5.14, m | 5.10, m |
| 8'-CH₃ | 1.59, s | 1.59, s | 1.60, s | 1.61, s | 1.60, s |
| 9' | 1.97, m | 1.97, m | 1.97, m | 2.07, m | 1.98, m |
| 10' | 2.05, m | 2.05, m | 2.05, m | 2.99, m | 2.05, m |
| 11' | 5.13, m | 5.10, m | 5.09, m | 5.14, m | 5.10, m |
| 12'a-CH₃ | 1.59, s | 1.59, s | 1.58, s | 1.60, s | 1.60, s |
| 12'b-CH₃ | 1.67, s | 1.67, s | 1.67, s | 1.69, s | 1.69, s |
| 2" | 4.67, s | 4.65, s | 4.76, s | 4.81, s | 4.87, s |
| 4" | 3.76, s | 3.77, s | 3.80, s | 3.80, s | 3.89, s |
| 5" | 2.58, s | 2.59, s | 3.37, d, 6.6 | 3.93, s | 2.71, m |
| 6" | | | 5.92, m | | 1.90, 1.98, m |
| 7" | | | 5.21, m | 7.33, m | 2.90, 2.09, m |
| 8" | | | | 7.33, m | |
| 9" | | | | 7.33, m | 2.90, 2.09, m |
| 10" | | | | 7.33, m | 1.90, 1.98, m |
| 11" | | | | 7.33, m | 3.46, s |
| 13" | | | | | 7.28, m |
| 14" | | | | | 7.28, m |
| 15" | | | | | 7.28, m |
| 16" | | | | | 7.28, m |
| 17" | | | | | 7.28, m |

$^a$ In CDCl₃, *J* in Hz. 400 MHz for ¹H-NMR.

Fig. 10

| | ¹H-NMR Data of Compounds 8-12[a] $\delta_H$, mult., $J$ | | | | |
|---|---|---|---|---|---|
| Position | 8 | 9 | 10 | 11 | 12 |
| 2-CH₃ | 1.26, s | 1.24, s | 1.25, s | 1.25, s | 1.24, s |
| 3 | 1.78, m | 1.77, m | 1.67, m | 1.75, m | 1.77, m |
| 4 | 2.48, m | 2.44, m | 2.45, m | 2.69, m | 2.65, m |
| 5 | | | | 6.39, s | |
| 7 | 6.45, s | | 6.49, s | | |
| 7-CH₃ | | 2.10, s | | | 2.10, s |
| 8-CH₃ | 2.11, s | 2.09, s | 2.12, s | 1.98, s | 2.09, s |
| 1' | 1.56, m | 1.55, m | 1.55, m | 1.52, m | 1.54, m |
| 2' | 2.12, m | 2.13, m | 2.14, m | 2.11, m | 2.13, m |
| 3' | 5.10, m | 5.09, m | 5.09, m | 5.10, m | 5.12, m |
| 4'-CH₃ | 1.60, s | 1.59, s | 1.59, s | 1.59, s | 1.59, s |
| 5' | 1.99, m | 1.97, m | 1.96, m | 1.96, m | 1.96, m |
| 6' | 2.09, m | 2.05, m | 2.05, m | 2.04, m | 2.04, m |
| 7' | 5.10, m | 5.09, m | 5.09, m | 5.10, m | 5.12, m |
| 8'-CH₃ | 1.60, s | 1.59, s | 1.59, s | 1.59, s | 1.59, s |
| 9' | 1.99, m | 1.97, m | 1.96, m | 1.96, m | 1.96, m |
| 10' | 2.09, m | 2.05, m | 2.05, m | 2.04, m | 2.04, m |
| 11' | 5.10, m | 5.09, m | 5.09, m | 5.10, m | 5.12, m |
| 12'a-CH₃ | 1.60, s | 1.58, s | 1.58, s | 1.58, s | 1.67, s |
| 12'b-CH₃ | 1.69, s | 1.67, s | 1.67, s | 1.67, s | 1.58, s |
| 2" | 4.85, s | 4.78, s | 4.74, s | 4.75, s | 4.30, s |
| 4" | 3.90, s | 3.84, s | 3.84, s | 3.90, s | 3.94, s |
| 5" | 2.71, m | 2.95, t, 5.2 | 2.95, t, 5.1 | 2.95, t, 5.1 | 2.97, t 6.6 |
| 6" | 1.90, 1.99, m | 3.69, t, 5.2 | 3.67, t, 5.2 | 3.68, t, 4.8 | 1.77, hidden |
| 7" | 2.90, 2.06, m | | | | 3.86, m |
| 8" | | | | | |
| 9" | 2.90, 2.06, m | | | | |
| 10" | 1.90, 1.99, m | | | | |
| 11" | 3.49, s | | | | |
| 13" | 7.28, m | | | | |
| 14" | 7.28, m | | | | |
| 15" | 7.28, m | | | | |
| 16" | 7.28, m | | | | |
| 17" | 7.28, m | | | | |

[a] In CDCl₃, $J$ in Hz. 400 MHz for ¹H-NMR.

Fig. 11

| $^1$H-NMR Data of Compounds 13-16.$^a$ | | | | $\delta_H$, mult., $J$ |
|---|---|---|---|---|
| Position | 13 | 14 | 15 | 16 |
| 2-CH$_3$ | 1.22, s | 1.24, s | 1.24, s | 1.23, s |
| 3 | 1.78, m | 1.78, m | 1.77, m | 1.73, m |
| 4 | 2.65, m | 2.44, m | 2.45, m | 2.42, m |
| 7 | 6.55, s | | 6.48, s | |
| 7-CH$_3$ | | 2.09, s | | 2.12, s |
| 8-CH$_3$ | 1.59, s | 2.08, s | 2.13, s | 2.09, s |
| 1' | 1.53, m | 1.54, m | 1.54, m | 1.52, m |
| 2' | 2.13, m | 2.12, m | 2.09, m | 2.12, m |
| 3' | 5.08, m | 5.09, m | 5.09, m | 5.07, m |
| 4'-CH$_3$ | 1.58, s | 1.59, s | 1.59, s | 1.58, s |
| 5' | 1.95, m | 1.96, m | 1.97, m | 1.95, m |
| 6' | 2.04, m | 2.04, m | 2.05, m | 2.03, m |
| 7' | 5.08, m | 5.09, m | 5.09, m | 5.07, m |
| 8'-CH$_3$ | 1.58, s | 1.59, s | 1.59, s | 1.58, s |
| 9' | 1.95, m | 1.96, m | 1.97, m | 1.95, m |
| 10' | 2.04, m | 2.04, m | 2.05, m | 2.03, m |
| 11' | 5.08, m | 5.09, m | 5.09, m | 5.07, m |
| 12'a-CH$_3$ | 1.59, s | 1.58, s | 1.58, s | 1.66, s |
| 12'b-CH$_3$ | 1.66, s | 1.67, s | 1.67, s | 1.57, s |
| 2" | 4.33, s | 4.77, s | 4.72, s | 4.69, s |
| 4" | 3.95, s | 3.79, s | 3.81, s | 3.75, s |
| 5" | 3.00, t, 5.5 | 2.80, t, 7.3 | 2.82, t, 6.9 | 2.60, m |
| 6" | 1.78, m | 1.88, q, 6.2 | 1.89, q, 6.6 | 1.23, m |
| 7" | 3.85, m | 4.62, t, 5.7 | 4.62, t, 5.8 | 1.78, 1.29, m |
| 8" | | 3.65, dq, 2.6, 7.3 | 3.63, dq, 2.6, 7.3 | 2.60, m, 3.60, s |
| | | 3.50, dq, 2.2, 7.0 | 3.50, dq, 2.6, 7.3 | |
| 9" | | 1.20, t, 6.9 | 1.19, t, 6.9 | |
| 10" | | 3.65, dq, 2.6, 7.3 | 3.63, dq, 2.6, 7.3 | 2.60, m, 3.60, s |
| | | 3.50, dq, 2.2, 7.0 | 3.50, dq, 2.6, 7.3 | |
| 11" | | 1.20, t, 6.9 | 1.19, t, 6.9 | 1.78, 1.29, m |

$^a$ In CDCl$_3$, $J$ in Hz. 400 MHz for $^1$H-NMR.

Fig. 12

| $^1$H-NMR Data of Compounds 17-20.$^a$ | | | | $\delta_H$, mult., $J$ |
|---|---|---|---|---|
| Position | 17 | 18 | 19 | 20 |
| 2-CH$_3$ | 1.24, s | 1.20, s | 1.25, s | 1.24, s |
| 3 | 1.77, m | 1.75, m | 1.77, m | 1.78, m |
| 4 | 2.45, m | 2.42, m | 2.44, m | 2.46, m |
| 7 | | 6.44, s | | 6.50, s |
| 7-CH$_3$ | 2.09, s | | 2.09, s | |
| 8-CH$_3$ | 2.08, s | 2.08, s | 2.08, s | 1.59, s |
| 1' | 1.55, m | 1.50, m | 1.56, m | 1.54, m |
| 2' | 2.13, m | 2.08, m | 2.12, m | 2.10, m |
| 3' | 5.10, m | 5.05, m | 5.09, m | 5.08, m |
| 4'-CH$_3$ | 1.59, s | 1.55, s | 1.59, s | 1.59, s |
| 5' | 1.97, m | 1.95, m | 1.96, m | 1.97, m |
| 6' | 2.05, m | 2.03, m | 2.06, m | 2.05, m |
| 7' | 5.10, m | 5.05, m | 2.09, m | 5.08, m |
| 8'-CH$_3$ | 1.59, s | 1.55, s | 1.59, s | 2.12, s |
| 9' | 1.97, m | 1.95, m | 1.96, m | 1.97, m |
| 10' | 2.05, m | 2.03, m | 2.06, m | 2.05, m |
| 11' | 5.10, m | 5.05, m | 5.09, m | 5.08, m |
| 12'a-CH$_3$ | 1.58, s | 1.54, s | 1.58, s | 1.58, s |
| 12'b-CH$_3$ | 1.67, s | 1.63, s | 1.67, s | 1.67, s |
| 2" | 4.74, s | 4.70, s | 4.73, s | 4.74, s |
| 4" | 3.80, s | 3.79, s | 3.82, s | 3.86, s |
| 5" | 2.73, t, 7.3 | 2.72, t, 7.1 | 2.78, t, 6.9 | 2.80, t, 6.6 |
| 6" | 1.59, m | 1.55, m | 1.67, m | 1.67, m |
| 7" | 1.43, m | 1.38, m | 1.67, m | 1.67, m |
| 8" | 1.59, m | 1.55, m | 2.36, t, 5.8 | 2.35, t, 6.1 |
| 9" | 3.64, t, 6.4 | 3.60, t, 6.6 | | |
| 10" | | | | |
| 11" | | | | |

$^a$ In CDCl$_3$, $J$ in Hz. 400 MHz for $^1$H-NMR.

Fig. 13

| $^1$H-NMR Data of Compounds 21-25.$^a$ | | | $\delta_H$, mult., $J$ | | |
|---|---|---|---|---|---|
| Position | 21 | 22 | 23 | 24 | 25 |
| 2-CH$_3$ | 1.24, s | 1.23, s | 1.24, s | 1.24, s | 1.24, s |
| 3 | 1.75, m | 1.76, m | 1.75, m | 1.76, m | 1.76, m |
| 4 | 2.45, m | 2.44, m | 2.43, m | 2.42, m | 2.42, m |
| 7 | | 6.47, s | | 6.50, s | 6.50, s |
| 7-CH$_3$ | 2.10, s | | 2.10, s | | |
| 8-CH$_3$ | 2.09, s | 2.10, s | 2.09, s | 2.12, s | 2.12, s |
| 1' | 1.56, m | 1.55, m | 1.55, m | 1.53, m | 1.53, m |
| 2' | 2.13, m | 2.14, m | 2.12, m | 2.14, m | 2.14, m |
| 3' | 5.11, m | 5.08, m | 5.11, m | 5.10, m | 5.10, m |
| 4'-CH$_3$ | 1.60, s | 1.58, s | 1.59, s | 1.60, s | 1.60, s |
| 5' | 1.98, m | 1.97, m | 1.97, m | 1.96, m | 1.96, m |
| 6' | 2.05, m | 2.04, m | 2.05, m | 2.05, m | 2.05, m |
| 7' | 5.11, m | 5.08, m | 5.11, m | 5.10, m | 5.10, m |
| 8'-CH$_3$ | 1.60, s | 1.58, s | 1.59, s | 1.60, s | 1.60, s |
| 9' | 1.98, m | 1.97, m | 1.97, m | 1.96, m | 1.96, m |
| 10' | 2.05, m | 2.04, m | 2.05, m | 2.05, m | 2.05, m |
| 11' | 5.11, m | 5.08, m | 5.11, m | 5.10, m | 5.10, m |
| 12'a-CH$_3$ | 1.59, s | 1.57, s | 1.58, s | 1.58, s | 1.58, s |
| 12'b-CH$_3$ | 1.67, s | 1.66, s | 1.67, s | 1.67, s | 1.67, s |
| 2" | 4.74, s | 4.71, s | 4.78, s | 4.78, s | 4.78, s |
| 4" | 3.81, s | 3.81, s | 3.85, s | 3.88, s | 3.88, s |
| 5" | 2.74, t, 7.32 | 2.74, t, 7.52 | 2.99, t, 6.22 | 3.03, t, 6.42 | 3.03, t, 6.42 |
| 6" | 1.39, m | 1.37, m | 2.85, t, 6.42 | 2.86, t, 6.96 | 2.86, t, 6.96 |
| 7" | 1.65, m | 1.64, m | | | |
| 8" | 1.65, m | 1.64, m | 6.74-6.77, m | 6.74-6.79, m | 6.74-6.79, m |
| 9" | 2.33, t, 7.36 | 2.32, t, 7.52 | | | |
| 10" | | | | | |
| 11" | | | 6.74-6.77, m | 6.74-6.79, m | 6.74-6.79, m |
| 12" | | | 6.74-6.77, m | 6.74-6.79, m | 6.74-6.79, m |
| 13" | | | 3.86, s | 3.85, s | 3.85, s |
| 14" | | | 3.84, s | 3.84, s | 3.84, s |

$^a$ In CDCl$_3$, $J$ in Hz. 400 MHz for $^1$H- NMR.

Fig. 14

| $^1$H-NMR Data of Compounds 26-29.$^a$ | | | $\delta_H$, mult., $J$ | |
|---|---|---|---|---|
| Position | 26 | 27 | 28 | 29 |
| 2-CH$_3$ | 1.24, s | 1.24, s | 1.23, s | 1.18, s |
| 3 | 1.77, m | 1.77, m | 1.73, m | 1.69, m |
| 4 | 2.42, m | 2.42, m | 2.34, m | 2.31, m |
| 7 | | 6.50, s | | 6.47, s |
| 7-CH$_3$ | 2.10, s | | 2.12, s | --- |
| 8-CH$_3$ | 2.09, s | 2.11, s | 2.12, s | 2.08, s |
| 1' | 1.55, m | 1.53, m | 1.55, m | 1.47, m |
| 2' | 2.14, m | 2.10, m | 2.09, m | 2.04, m |
| 3' | 5.10, m | 5.09, m | 5.09, m | 5.02, m |
| 4'-CH$_3$ | 1.60, s | 1.59, s | 1.59, s | 1.53, s |
| 5' | 1.97, m | 1.97, m | 1.96, m | 1.91, m |
| 6' | 2.05, m | 2.05, m | 2.04, m | 1.97, m |
| 7' | 5.10, m | 5.09, m | 5.09, m | 5.02, m |
| 8'-CH$_3$ | 1.60, s | 1.59, s | 1.59, s | 1.53, s |
| 9' | 1.97, m | 1.97, m | 1.96, m | 1.91, m |
| 10' | 2.05, m | 2.05, m | 2.04, m | 1.97, m |
| 11' | 5.10, m | 5.09, m | 5.09, m | 5.02, m |
| 12'a-CH$_3$ | 1.58, s | 1.58, s | 1.58, s | 1.52, s |
| 12'b-CH$_3$ | 1.68, s | 1.67, s | 1.67, s | 1.60, s |
| 2" | 4.78, s | 4.78, s | 4.79, s | 4.69, s |
| 4" | 3.84, s | 3.87, s | 3.79, s | 3.95, s |
| 5" | 2.98, t, 7.7 | 3.00, t, 6.9 | 4.02, s | 3.73, d, 4.1 |
| 6" | 2.82, t, 7.7 | 2.83, t, 6.9 | | |
| 7" | | | 8.29, brs | 8.29, brs |
| 8" | 7.06, d, 8.4 | 7.04, d, 8.4 | | |
| 9" | 6.71, d, 8.4 | 6.72, d, 8.4 | 8.13, ddd, 1.1, 2.2, 8.4 | 8.08, d, 8.2 |
| 10" | | | 7.51, dd, 7.7, 8.1 | 7.44, dd, 8.2, 7.8 |
| 11" | 6.71, d, 8.4 | 6.72, d, 8.1 | 7.69, brd, 7.32 | 7.63, d, 7.32 |
| 12" | 7.06, d, 8.4 | 7.04, d, 8.1 | | |
| 13" | | | | |
| 14" | | | | |

$^a$ In CDCl$_3$, $J$ in Hz. 400 MHz for $^1$H- NMR.

Fig. 15

| | 1H-NMR Data of Compounds 30-33.[a] | $\delta_H$, mult., $J$ | | |
|---|---|---|---|---|
| | 30 | 31 | 32 | 33 |
| 2-CH₃ | 1.20, s | 1.21, s | 1.23, s | 1.23, s |
| 3 | 1.74, m | 1.74, m | 1.77, m | 1.74, m |
| 4 | 2.56, t, 6.9 | 2.57, t, 6.4 | 2.62, m | 2.60, m |
| 5 | | | | |
| 7 | | | | 6.51, s |
| 7-CH₃ | 2.13, s | 2.13, s | 2.15, s | |
| 8-CH₃ | 2.09, s | 2.09, s | 2.11, s | 2.10, s |
| 1' | 1.52, m | 1.52, m | 1.52, m | 1.52, m |
| 2' | 2.10, m | 2.11, m | 2.12, m | 2.10, m |
| 3' | 5.08, m | 5.08, m | 5.11, m | 5.10, m |
| 4'-CH₃ | 1.57, s | 1.57, s | 1.59, s | 1.58, s |
| 5' | 1.94, m | 1.96, m | 1.96, m | 1.98, m |
| 6' | 2.03, m | 2.04, m | 2.05, m | 2.05, m |
| 7' | 5.08, m | 5.08, m | 5.11, m | 5.10, m |
| 8'-CH₃ | 1.57, s | 1.57, s | 1.59, s | 1.58, s |
| 9' | 1.94, m | 1.96, m | 1.96, m | 1.98, m |
| 10' | 2.03, m | 2.04, m | 2.05, m | 2.05, m |
| 11' | 5.08, m | 5.08, m | 5.11, m | 5.10, m |
| 12'a-CH₃ | 1.56, s | 1.58, s | 1.58, s | 1.58, s |
| 12'b-CH₃ | 1.65, s | 1.66, s | 1.67, s | 1.67, s |
| 1" | 3.89, s | 3.89, s | 4.85, s | 4.79, s |
| 2" | | | | |
| 3" | 2.91, t, 7.3 | 2.88, t, 7.1 | | |
| 4" | 2.77, t, 6.4 | 2.74, t, 6.9 | | |
| 5" | | | | |
| 6" | 6.69, d, 1.8 | 7.01, d, 8.2 | | |
| 7" | | 6.74, d, 8.7 | | |
| 8" | | | | |
| 9" | 6.78, d, 7.8 | 6.74, d, 8.7 | | |
| 10" | 6.72, dd, 1.8, 8.2 | 7.01, d, 8.2 | | |
| 11" | 3.86, s or 3.84, s | | | |
| 12" | 3.86, s or 3.84, s | | | |

[a] In CDCl₃, $J$ in Hz. 400 MHz for ¹H-NMR.

Fig. 16

| $^1$H-NMR Data of Compounds 34-37.$^a$ | | | | $δ_H$, mult., $J$ |
|---|---|---|---|---|
| | 34 | 35 | 36 | 37 |
| 2-CH$_3$ | 1.24, s | 1.23, s | 1.23, s | 1.23, s |
| 3 | 1.74, m | 1.76, m | 1.76, m | 1.76, m |
| 4 | 2.68, m | 2.43, m | 2.44, m | 2.44, m |
| 5 | 6.44, s | | | |
| 7 | | | 6.47, s | |
| 7-CH$_3$ | | 2.08, s | | 2.09. s |
| 8-CH$_3$ | 2.10, s | 2.07, s | 2.10, s | 2.08, s |
| 1' | 1.53, m | 1.54, m | 1.54, s | 1.55, m |
| 2' | 2.09, m | 2.11, m | 2.06, m | 2.12, m |
| 3' | 5.08, m | 5.07, m | 5.07, m | 5.08, m |
| 4'-CH$_3$ | 1.58, s | 1.58, s | 1.58, s | 1.58, s |
| 5' | 1.96, m | 1.96, m | 1.95, m | 1.96, m |
| 6' | 2.04, m | 2.03, m | 2.04, m | 2.04, m |
| 7' | 5.08, m | 5.07, m | 5.07, m | 5.08, m |
| 8'-CH$_3$ | 1.58, s | 1.58, s | 1.58, s | 1.58, s |
| 9' | 1.96, m | 1.95, m | 1.95, m | 1.96, m |
| 10' | 2.04, m | 2.03, m | 2.04, m | 2.04, m |
| 11' | 5.08, m | 5.07, m | 5.07, m | 5.08, m |
| 12'a-CH$_3$ | 1.58, s | 1.57, s | 1.57, s | 1.57, s |
| 12'b-CH$_3$ | 1.67, s | 1.66, s | 1.66, s | 1.66, s |
| 1" | 4.87, s | | | |
| 2" | | 4.73, s | 4.71, s | 4.73, s |
| 3" | | | | |
| 4" | | 3.81, s | 3.81, s | 3.79, s |
| 5" | | 2.77, t, 5.9 | 2.79, t, 5.5 | 2.71, t, 7.3 |
| 6" | | 1.69, m | 1.68, m | 1.56, m |
| 7" | | 1.69, m | 1.68, m | 1.37, m |
| 8" | | 3.63, t, 5.4 | 3.62, t, 5 | 1.37, m |
| 9" | | | | 1.56, m |
| 10" | | | | 3.62, t, 6.4 |
| 11" | | | | |
| 12" | | | | |

$^a$ In CDCl$_3$, $J$ in Hz. 400 MHz for $^1$H-NMR.

Fig. 17

| $^1$H-NMR Data of Compounds 38-40.[a] | | | $\delta_H$, mult., $J$ |
|---|---|---|---|
| | 38 | 39 | 40 |
| 2-CH$_3$ | 1.24, s | 1.24, s | 1.24, s |
| 3 | 1.77, m | 1.76, m | 1.77, m |
| 4 | 2.45, m | 2.44, m | 2.45, m |
| 5 | | | |
| 7 | 6.47, s | | 6.47, s |
| 7-CH$_3$ | | 2.08. s | |
| 8-CH$_3$ | 2.19, s | 2.08, s | 2.11, s |
| 1' | 1.52, m | 1.55, m | 1.55, m |
| 2' | 2.15, m | 2.11, m | 2.15, m |
| 3' | 5.08, m | 5.08, m | 5.09, m |
| 4'-CH$_3$ | 1.59, s | 1.58, s | 1.59, s |
| 5' | 1.96, m | 1.96, m | 1.96, m |
| 6' | 2.04, m | 2.04, m | 2.05, m |
| 7' | 5.08, m | 5.08, m | 5.09, m |
| 8'-CH$_3$ | 1.59, s | 1.58, s | 1.59, s |
| 9' | 1.96, m | 1.96, m | 1.96, m |
| 10' | 2.04, m | 2.04, m | 2.05, m |
| 11' | 5.08, m | 5.08, m | 5.09, m |
| 12'a-CH$_3$ | 1.58, s | 1.57, s | 1.58, s |
| 12'b-CH$_3$ | 1.67, s | 1.66, s | 1.67, s |
| 1" | | | |
| 2" | 4.71, s | 4.73, s | 4.71, s |
| 3" | | | |
| 4" | 3.79, s | 3.79, s | 3.80, s |
| 5" | 2.72, t, 7.3 | 2.70, t, 8 | 2.71, t, 7.4 |
| 6" | 1.56, m | 1.55, m | 1.55, m |
| 7" | 1.37, m | 1.31, m | 1.32, m |
| 8" | 1.37, m | 1.31, m | 1.32, m |
| 9" | 1.56, m | 1.31, m | 1.32, m |
| 10" | 3.61, t, 6.4 | 1.31, m | 1.32, m |
| 11" | | 1.55, m | 1.55, m |
| 12" | | 3.61, t, 6.4 | 3.61, t, 6.8 |

[a] In CDCl$_3$, $J$ in Hz. 400 MHz for $^1$H-NMR.

Fig. 18

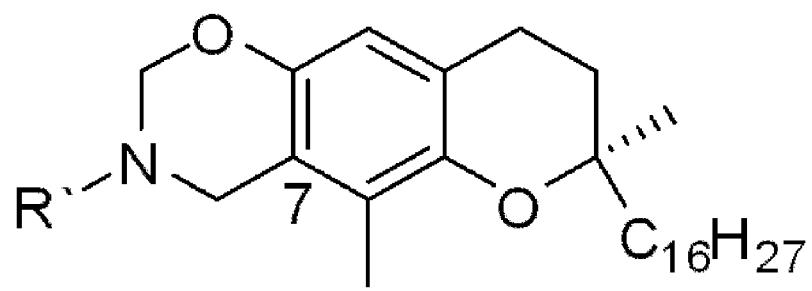
Compound 11: R` = CH₂CH₂OH
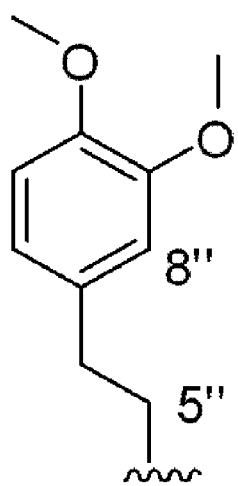
Compound 25: R` =
Fig. 20

|  | R | R` |
|---|---|---|
| Compound 3 | $CH_3$ | $CH_3$ |
| Compound 4 | H | $CH_3$ |
| Compound 5 | $CH_3$ | $CH_2CH=CH_2$ |
| Compound 6 | $CH_3$ | a |
| Compound 7 | $CH_3$ | b |
| Compound 8 | H | b |
| Compound 9 | $CH_3$ | $CH_2CH_2OH$ |
| Compound 10 | H | $CH_2CH_2OH$ |
| Compound 12 | $CH_3$ | $(CH_2)_3OH$ |
| Compound 13 | H | $(CH_2)_3OH$ |
| Compound 14 | $CH_3$ | c |
| Compound 15 | H | c |
| Compound 16 | $CH_3$ | d |
| Compound 17 | $CH_3$ | $(CH_2)_5OH$ |
| Compound 18 | H | $(CH_2)_5OH$ |
| Compound 19 | $CH_3$ | $(CH_2)_4COOH$ |
| Compound 20 | H | $(CH_2)_4COOH$ |
| Compound 21 | $CH_3$ | $(CH_2)_5COOH$ |
| Compound 22 | H | $(CH_2)_5COOH$ |
| Compound 23 | $CH_3$ | e |
| Compound 24 | H | e |
| Compound 26 | $CH_3$ | f |
| Compound 27 | H | f |
| Compound 28 | $CH_3$ | g |
| Compound 29 | H | g |
| Compound 35 | $CH_3$ | $(CH_2)_4OH$ |
| Compound 36 | H | $(CH_2)_4OH$ |
| Compound 37 | $CH_3$ | $(CH_2)_6OH$ |
| Compound 38 | H | $(CH_2)_6OH$ |
| Compound 39 | $CH_3$ | $(CH_2)_8OH$ |
| Compound 40 | H | $(CH_2)_8OH$ |
| Compound 41 | $CH_3$ | $(CH_2)_{10}OH$ |
| Compound 42 | H | $(CH_2)_{10}OH$ |
| Compound 43 | $CH_3$ | $(CH_2)_{12}OH$ |
| Compound 44 | H | $(CH_2)_{12}OH$ |

Fig. 22

Compound 34

Compound 32: R = CH₃;  Compound 33: R = H

Compound 30: R` = e;  Compound 31: R` = f

| Compound | Amine |
|---|---|
| 3 | methanamine |
| 4 | methanamine |
| 5 | prop-2-en-1-amine |
| 6 | phenylmethanamine |
| 7 | 1-benzylpiperidin-4-amine |
| 8 | 1-benzylpiperidin-4-amine |
| 9 | 2-aminoethanol |
| 10 | 2-aminoethanol |
| 11 | 2-aminoethanol |
| 12 | 3-aminopropan-1-ol |
| 13 | 3-aminopropan-1-ol |
| 14 | 3,3-diethoxypropan-1-amine |
| 15 | 3,3-diethoxypropan-1-amine |
| 16 | piperidin-4-ylmethanamine |
| 17 | 5-aminopentan-1-ol |
| 18 | 5-aminopentan-1-ol |
| 19 | 5-aminopentanoic acid |
| 20 | 5-aminopentanoic acid |
| 21 | 6-aminohexanoic acid |
| 22 | 6-aminohexanoic acid |
| 23 | 2-(3,4-dimethoxyphenyl)ethanamine |
| 24 | 2-(3,4-dimethoxyphenyl)ethanamine |
| 25 | 2-(3,4-dimethoxyphenyl)ethanamine |
| 26 | 4-(2-aminoethyl)phenol |
| 27 | 4-(2-aminoethyl)phenol |
| 28 | (3-nitrophenyl)methanamine |
| 29 | (3-nitrophenyl)methanamine |
| 30 | 2-(3,4-dimethoxyphenyl)ethanamine |
| 31 | 4-(2-aminoethyl)phenol |
| 35 | 4-aminobutan-1-ol |
| 36 | 4-aminobutan-1-ol |
| 37 | 6-aminohexan-1-ol |
| 38 | 6-aminohexan-1-ol |
| 39 | 8-aminooctan-1-ol |
| 40 | 8-aminooctan-1-ol |

Fig. 27

| Compound | IC$_{50}$ (μM) | Compound | IC$_{50}$ (μM) | Compound | IC$_{50}$ (μM) |
| --- | --- | --- | --- | --- | --- |
| 3 | 2.18 | 17 | 1.65 | 31 | 2.34 |
| 4 | 1.27 | 18 | 0.70 | 32 | 2.60 |
| 5 | 11.64 | 19 | 1.81 | 33 | >20 |
| 6 | 1.99 | 20 | 11.86 | 34 | 6.60 |
| 7 | 8.70 | 21 | 4.95 | 35 | 2.24 |
| 8 | 0.82 | 22 | 5.13 | 36 | 1.84 |
| 9 | 1.67 | 23 | 1.83 | 37 | 2.09 |
| 10 | 4.23 | 24 | 0.87 | 38 | 1.26 |
| 11 | 0.96 | 25 | 0.84 | 39 | 1.43 |
| 12 | 2.53 | 26 | 1.49 | 40 | 0.79 |
| 13 | 1.83 | 27 | 0.91 | 41 | 4.4 |
| 14 | 9.32 | 28 | 24.62 | 42 | 3.6 |
| 15 | 1.01 | 29 | 29.14 | 43 | >5.0 |
| 16 | 4.56 | 30 | 1.69 | 44 | 2.0 |

Mean antiproliferative activity of tocotrienol analogues against the highly metastatic +SA mammary epithelial cancer cell line. Experiments conducted in triplicate.

Fig. 28

| Panel/Cell Line | Growth % | | [Mean Growth Percent - Growth Percent] |
|---|---|---|---|
| Leukemia | | | |
| CCRF-CEM | 83.98 | 15.2 | |
| HL-60(TB) | 86.47 | 12.71 | |
| K-562 | 85.02 | 14.16 | |
| MOLT-4 | 84.35 | 14.83 | |
| RPMI-8226 | 77.95 | 21.23 | |
| SR | 85.5 | 13.68 | |
| Non-Small Cell Lung Cancer | | | |
| A549/ATCC | 104.64 | -5.46 | |
| EKVX | 110.37 | -11.19 | |
| HOP-62 | 107.97 | -8.79 | |
| HOP-92 | 92.04 | 7.14 | |
| NCI-H226 | 90.78 | 8.4 | |
| NCI-H23 | 92.82 | 6.36 | |
| NCI-H322M | 95.17 | 4.01 | |
| NCI-H460 | 105 | -5.82 | |
| NCI-H522 | 68.75 | 30.43 | |
| Colon Cancer | | | |
| COLO 205 | 94.39 | 4.79 | |
| HCC-2998 | 114.7 | -15.52 | |
| HCT-116 | 109.37 | -10.19 | |
| HCT-15 | 101.8 | -2.62 | |
| HT29 | 96.13 | 3.05 | |
| KM12 | 106.82 | -7.64 | |
| SW-620 | 109.84 | -10.66 | |
| CNS Cancer | | | |
| SF-268 | 107.72 | -8.54 | |
| SF-295 | 105.18 | -6 | |
| SF-539 | 100.67 | -1.49 | |
| SNB-19 | 113.81 | -14.63 | |
| SNB-75 | 84.3 | 14.88 | |
| U251 | 101.69 | -2.51 | |

Compound 1

Fig. 37

| Panel/Cell Line | Growth % | [Mean Growth Percent - Growth Percent] |
|---|---|---|
| Melanoma | | |
| LOX IMVI | 89.99 | 9.19 |
| MALME-3M | 92.45 | 6.73 |
| M14 | 108.68 | -9.5 |
| MDA-MB-435 | 102.25 | -3.07 |
| SK-MEL-2 | 91.27 | 7.91 |
| SK-MEL-28 | 97.29 | 1.89 |
| SK-MEL-5 | 99.06 | 0.12 |
| UACC-257 | 122.52 | -23.34 |
| UACC-62 | 107.91 | -8.73 |
| Ovarian Cancer | | |
| IGROV1 | 96.27 | 2.91 |
| OVCAR-3 | 110.11 | -10.93 |
| OVCAR-4 | 101.56 | -2.38 |
| OVCAR-5 | 113.76 | -14.58 |
| OVCAR-8 | 112.34 | -13.16 |
| NCI/ADR-RES | 96.88 | 2.3 |
| Renal Cancer | | |
| 786-0 | 114.48 | -15.3 |
| ACHN | 100.38 | -1.2 |
| CAKI-1 | 89.5 | 9.68 |
| RXF 393 | 84.11 | 15.07 |
| SN12C | 95.95 | 3.23 |
| TK-10 | 122.31 | -23.13 |
| UO-31 | 64.07 | 35.11 |
| Prostate Cancer | | |
| PC-3 | 96.6 | 2.58 |
| DU-145 | 99.66 | -0.48 |
| Breast Cancer | | |
| MCF7 | 64.14 | 35.04 |
| MDA-MB- | 108.35 | -9.17 |
| HS 578T | 101.91 | -2.73 |
| BT-549 | 140.98 | -41.8 |
| T-47D | 82.5 | 16.68 |
| MDA-MB-468 | 108.15 | -8.97 |

Compound 1

Fig. 38

Compound 8

| Panel/Cell Line | Growth % | [Mean Growth Percent - Growth Percent] |
|---|---|---|
| Melanoma | | |
| LOX IMVI | -47.37 | 75.81 |
| MALME-3M | 121.6 | -93.16 |
| M14 | 50.12 | -21.68 |
| MDA-MB-435 | 3.07 | 25.37 |
| SK-MEL-2 | 109.25 | -80.81 |
| SK-MEL-28 | 60.02 | -31.58 |
| SK-MEL-5 | 110.06 | -81.62 |
| UACC-257 | 93.03 | -64.59 |
| UACC-62 | 93.58 | -65.14 |
| Ovarian Cancer | | |
| IGROV1 | -48.51 | 76.95 |
| OVCAR-3 | -47.86 | 76.3 |
| OVCAR-4 | 59.04 | -30.6 |
| OVCAR-5 | 78.99 | -50.55 |
| OVCAR-8 | -85.77 | 114.21 |
| NCI/ADR-RES | 62.93 | -34.49 |
| SK-OV-3 | 108.64 | -80.2 |
| Renal Cancer | | |
| 786-0 | 24.14 | 4.3 |
| A498 | 63.21 | -34.77 |
| ACHN | 83.17 | -54.73 |
| CAKI-1 | 75.32 | -46.88 |
| SN12C | 1.77 | 26.67 |
| TK-10 | 82.47 | -54.03 |
| UO-31 | 57.77 | -29.33 |
| Prostate Cancer | | |
| PC-3 | 33.18 | -4.74 |
| DU-145 | 65.32 | -36.88 |
| Breast Cancer | | |
| MCF7 | -35.97 | 64.41 |
| MDA-MB- | 18.2 | 10.24 |
| HS 578T | -6.43 | 34.87 |
| BT-549 | 109.27 | -80.83 |
| T-47D | 89.3 | -60.86 |
| MDA-MB-468 | 0.33 | 28.11 |

Compound 8

Fig. 40

| Panel/Cell Line | Growth % | [Mean Growth Percent - Growth Percent] |
|---|---|---|
| Leukemia | | |
| CCRF-CEM | 28.62 | -29.72 |
| HL-60(TB) | 15.27 | -16.37 |
| K-562 | -33.41 | 32.31 |
| MOLT-4 | -20.33 | 19.23 |
| RPMI-8226 | 2.29 | -3.39 |
| SR | -32.12 | 31.02 |
| Non-Small Cell Lung Cancer | | |
| A549/ATCC | -35.92 | 34.82 |
| EKVX | 82.68 | -83.78 |
| HOP-62 | -76.27 | 75.17 |
| HOP-92 | 63.13 | -64.23 |
| NCI-H226 | 98.66 | -99.76 |
| NCI-H23 | 51.91 | -53.01 |
| NCI-H322M | -62.14 | 61.04 |
| NCI-H460 | -75.06 | 73.96 |
| NCI-H522 | -72.9 | 71.8 |
| Colon Cancer | | |
| COLO 205 | -92.53 | 91.43 |
| HCC-2998 | -82.94 | 81.84 |
| HCT-116 | -85.37 | 84.27 |
| HCT-15 | 0.85 | -1.95 |
| HT29 | -76.74 | 75.64 |
| KM12 | -77.42 | 76.32 |
| SW-620 | -92.13 | 91.03 |
| CNS Cancer | | |
| SF-268 | -78.48 | 77.38 |
| SF-295 | 74.05 | -75.15 |
| SF-539 | 74.44 | -75.54 |
| SNB-19 | 4.52 | -5.62 |
| SNB-75 | 33.91 | -35.01 |
| U251 | -83.38 | 82.28 |

Compound 13

Fig. 41

| Panel/Cell Line | Growth % | [Mean Growth Percent - Growth Percent] |
|---|---|---|
| Melanoma | | |
| LOX IMVI | -89.85 | 88.75 |
| MALME-3M | 110.12 | -111.2 |
| M14 | 15.14 | -16.24 |
| MDA-MB-435 | -23.99 | 22.89 |
| SK-MEL-2 | 107.36 | -108.5 |
| SK-MEL-28 | -50.66 | 49.56 |
| SK-MEL-5 | 57.47 | -58.57 |
| UACC-257 | 64.25 | -65.35 |
| UACC-62 | 93.03 | -94.13 |
| Ovarian Cancer | | |
| IGROV1 | -6.58 | 5.48 |
| OVCAR-3 | -38.37 | 37.27 |
| OVCAR-4 | -46.5 | 45.4 |
| OVCAR-5 | 40.37 | -41.47 |
| OVCAR-8 | -77.69 | 76.59 |
| NCI/ADR-RES | -26.43 | 25.33 |
| SK-OV-3 | 88.35 | -89.45 |
| Renal Cancer | | |
| 786-0 | 16.55 | -17.65 |
| A498 | 106.26 | -107.4 |
| ACHN | 42.55 | -43.65 |
| CAKI-1 | 60.41 | -61.51 |
| RXF 393 | -90.52 | 89.42 |
| SN12C | 11.67 | -12.77 |
| TK-10 | 75.92 | -77.02 |
| UO-31 | 59.39 | -60.49 |
| Prostate Cancer | | |
| PC-3 | 50.84 | -51.94 |
| DU-145 | -13.63 | 12.53 |
| Breast Cancer | | |
| MCF7 | -94.16 | 93.06 |
| MDA-MB- | 10.6 | -11.7 |
| HS 578T | -11.76 | 10.66 |
| BT-549 | 91.97 | -93.07 |
| T-47D | -22.13 | 21.03 |
| MDA-MB-468 | -28.98 | 27.88 |

Compound 13

Fig. 42

Compound 17  Fig. 43

| Panel/Cell Line | Growth % | [Mean Growth Percent - Growth Percent] |
|---|---|---|
| Melanoma | | |
| LOX IMVI | 40.23 | 29.1 |
| MALME-3M | 106.08 | -36.75 |
| M14 | 107.14 | -37.81 |
| MDA-MB-435 | 35.49 | 33.84 |
| SK-MEL-2 | 106.66 | -37.33 |
| SK-MEL-28 | 99.74 | -30.41 |
| SK-MEL-5 | 107.85 | -38.52 |
| UACC-257 | 110.29 | -40.96 |
| UACC-62 | 99.25 | -29.92 |
| Ovarian Cancer | | |
| IGROV1 | 63.7 | 5.63 |
| OVCAR-3 | 65.22 | 4.11 |
| OVCAR-4 | 93.07 | -23.74 |
| OVCAR-5 | 94.4 | -25.07 |
| OVCAR-8 | 69.05 | 0.28 |
| NCI/ADR-RES | 82.48 | -13.15 |
| SK-OV-3 | 101.29 | -31.96 |
| Renal Cancer | | |
| 786-0 | 90.16 | -20.83 |
| A498 | 97.37 | -28.04 |
| ACHN | 101.4 | -32.07 |
| CAKI-1 | 70 | -0.67 |
| SN12C | 78.45 | -9.12 |
| TK-10 | 97.54 | -28.21 |
| UO-31 | 64.59 | 4.74 |
| Prostate Cancer | | |
| PC-3 | 71.77 | -2.44 |
| DU-145 | 99.59 | -30.26 |
| Breast Cancer | | |
| MCF7 | 24.29 | 45.04 |
| MDA-MB- | 54.97 | 14.36 |
| HS 578T | 97.31 | -27.98 |
| BT-549 | 113.53 | -44.2 |
| T-47D | 94.41 | -25.08 |
| MDA-MB-468 | 87.41 | -18.08 |

Compound 17

Fig. 44

Compound 18

Compound 18

| Panel/Cell Line | Growth % | | [Mean Growth Percent - Growth Percent] |
|---|---|---|---|
| Leukemia | | | |
| CCRF-CEM | 78.05 | 18.12 | |
| HL-60(TB) | 79.44 | 16.73 | |
| K-562 | 78.26 | 17.91 | |
| MOLT-4 | 75.96 | 20.21 | |
| RPMI-8226 | 64.57 | 31.6 | |
| SR | 54.65 | 41.52 | |
| Non-Small Cell Lung Cancer | | | |
| A549/ATCC | 98.87 | -2.7 | |
| EKVX | 94.13 | 2.04 | |
| HOP-62 | 85.74 | 10.43 | |
| HOP-92 | 106.5 | -10.33 | |
| NCI-H226 | 97.03 | -0.86 | |
| NCI-H23 | 101.9 | -5.73 | |
| NCI-H322M | 100.95 | -4.78 | |
| NCI-H460 | 102.52 | -6.35 | |
| NCI-H522 | 98.63 | -2.46 | |
| Colon Cancer | | | |
| COLO 205 | 86.65 | 9.52 | |
| HCC-2998 | 70.47 | 25.7 | |
| HCT-116 | 91.86 | 4.31 | |
| HCT-15 | 101.88 | -5.71 | |
| HT29 | 91.69 | 4.48 | |
| KM12 | 96.39 | -0.22 | |
| SW-620 | 100.82 | -4.65 | |
| CNS Cancer | | | |
| SF-268 | 94.83 | 1.34 | |
| SF-295 | 108.28 | -12.11 | |
| SF-539 | 102.98 | -6.81 | |
| SNB-19 | 104.01 | -7.84 | |
| SNB-75 | 82.76 | 13.41 | |
| U251 | 88.39 | 7.78 | |

Compound 23

Fig. 47

| Panel/Cell Line | Growth % | [Mean Growth Percent - Growth Percent] |
|---|---|---|
| Melanoma | | |
| LOX IMVI | 98.57 | -2.4 |
| MALME-3M | 93.62 | 2.55 |
| M14 | 101.16 | -4.99 |
| MDA-MB-435 | 90.68 | 5.49 |
| SK-MEL-2 | 120.28 | -24.11 |
| SK-MEL-28 | 93.56 | 2.61 |
| SK-MEL-5 | 106.59 | -10.42 |
| UACC-257 | 105.34 | -9.17 |
| UACC-62 | 96.54 | -0.37 |
| Ovarian Cancer | | |
| IGROV1 | 87.37 | 8.8 |
| OVCAR-3 | 105.4 | -9.23 |
| OVCAR-4 | 98.44 | -2.27 |
| OVCAR-5 | 100.85 | -4.68 |
| OVCAR-8 | 100.94 | -4.77 |
| NCI/ADR-RES | 100.79 | -4.62 |
| SK-OV-3 | 95.27 | 0.9 |
| Renal Cancer | | |
| 786-0 | 94.86 | 1.31 |
| A498 | 108.17 | -12 |
| ACHN | 95.81 | 0.36 |
| CAKI-1 | 88.47 | 7.7 |
| SN12C | 87.27 | 8.9 |
| TK-10 | 105.12 | -8.95 |
| UO-31 | 76.18 | 19.99 |
| Prostate Cancer | | |
| PC-3 | 94.26 | 1.91 |
| DU-145 | 110.71 | -14.54 |
| Breast Cancer | | |
| MCF7 | 77.5 | 18.67 |
| MDA-MB- | 96.12 | 0.05 |
| HS 578T | 197.88 | -101.7 |
| BT-549 | 115 | -18.83 |
| T-47D | 97.97 | -1.8 |
| MDA-MB-468 | 95.11 | 1.06 |

Compound 23

Fig. 48

Compound 24

| Panel/Cell Line | Growth % | [Mean Growth Percent - Growth Percent] |
|---|---|---|
| Melanoma | | |
| LOX IMVI | -77.66 | 94 |
| MALME-3M | 72.89 | -56.55 |
| M14 | -19.47 | 35.81 |
| MDA-MB-435 | -51.13 | 67.47 |
| SK-MEL-2 | 86.42 | -70.08 |
| SK-MEL-28 | -55.56 | 71.9 |
| SK-MEL-5 | 89.98 | -73.64 |
| UACC-257 | 71.83 | -55.49 |
| UACC-62 | 91.69 | -75.35 |
| Ovarian Cancer | | |
| IGROV1 | 31.76 | -15.42 |
| OVCAR-3 | -22.95 | 39.29 |
| OVCAR-4 | 40.13 | -23.79 |
| OVCAR-5 | 42.67 | -26.33 |
| OVCAR-8 | -70.69 | 87.03 |
| NCI/ADR-RES | 49.12 | -32.78 |
| SK-OV-3 | 92.84 | -76.5 |
| Renal Cancer | | |
| 786-0 | 49.28 | -32.94 |
| A498 | 83.21 | -66.87 |
| ACHN | 75.66 | -59.32 |
| CAKI-1 | 79.75 | -63.41 |
| SN12C | 37.05 | -20.71 |
| TK-10 | 97.71 | -81.37 |
| UO-31 | 51.18 | -34.84 |
| Prostate Cancer | | |
| PC-3 | 62.06 | -45.72 |
| DU-145 | -4.93 | 21.27 |
| Breast Cancer | | |
| MCF7 | -65.73 | 82.07 |
| MDA-MB- | 13.21 | 3.13 |
| BT-549 | 105.22 | -88.88 |
| T-47D | 31.17 | -14.83 |
| MDA-MB-468 | -25.42 | 41.76 |

Compound 24

Fig. 50

| Panel/Cell Line | Growth % | [Mean Growth Percent - Growth Percent] |
|---|---|---|
| Leukemia | | |
| CCRF-CEM | 49.56 | 31.2 |
| HL-60(TB) | 72.33 | 8.43 |
| K-562 | 54.94 | 25.82 |
| MOLT-4 | 40.43 | 40.33 |
| SR | 16.33 | 64.43 |
| Non-Small Cell Lung Cancer | | |
| A549/ATCC | 92.85 | -12.09 |
| EKVX | 93.92 | -13.16 |
| HOP-62 | 111.59 | -30.83 |
| HOP-92 | 87.88 | -7.12 |
| NCI-H226 | 110.89 | -30.13 |
| NCI-H23 | 88.22 | -7.46 |
| NCI-H322M | 96.01 | -15.25 |
| NCI-H460 | 62.44 | 18.32 |
| NCI-H522 | 89.95 | -9.19 |
| Colon Cancer | | |
| COLO 205 | 52.12 | 28.64 |
| HCC-2998 | 23.28 | 57.48 |
| HCT-116 | 37.73 | 43.03 |
| HCT-15 | 102.28 | -21.52 |
| HT29 | 84.47 | -3.71 |
| KM12 | 65.6 | 15.16 |
| SW-620 | 48.39 | 32.37 |
| CNS Cancer | | |
| SF-268 | 83.74 | -2.98 |
| SF-295 | 100.08 | -19.32 |
| SF-539 | 104.42 | -23.66 |
| SNB-19 | 94.11 | -13.35 |
| SNB-75 | 69.22 | 11.54 |
| U251 | 81.79 | -1.03 |

Compound 26

Fig. 51

| Panel/Cell Line | Growth % | [Mean Growth Percent - Growth Percent] |
|---|---|---|
| Melanoma | | |
| LOX IMVI | 30.32 | 50.44 |
| MALME-3M | 114.22 | -33.46 |
| M14 | 97.58 | -16.82 |
| MDA-MB-435 | 54.53 | 26.23 |
| SK-MEL-2 | 120.99 | -40.23 |
| SK-MEL-28 | 76.63 | 4.13 |
| SK-MEL-5 | 114.85 | -34.09 |
| UACC-257 | 93.63 | -12.87 |
| UACC-62 | 104.2 | -23.44 |
| Ovarian Cancer | | |
| IGROV1 | 67.68 | 13.08 |
| OVCAR-3 | 98.17 | -17.41 |
| OVCAR-4 | 81.39 | -0.63 |
| OVCAR-5 | 111.46 | -30.7 |
| OVCAR-8 | 42.06 | 38.7 |
| NCI/ADR-RES | 83.56 | -2.8 |
| SK-OV-3 | 104.69 | -23.93 |
| Renal Cancer | | |
| 786-0 | 77.28 | 3.48 |
| A498 | 90.16 | -9.4 |
| ACHN | 99.78 | -19.02 |
| CAKI-1 | 84.17 | -3.41 |
| SN12C | 85.36 | -4.6 |
| TK-10 | 105.79 | -25.03 |
| UO-31 | 71.88 | 8.88 |
| Prostate Cancer | | |
| PC-3 | 79.86 | 0.9 |
| DU-145 | 106.7 | -25.94 |
| Breast Cancer | | |
| MCF7 | 16.9 | 63.86 |
| MDA-MB- | 68.53 | 12.23 |
| HS 578T | 91.84 | -11.08 |
| BT-549 | 112.81 | -32.05 |
| T-47D | 93.73 | -12.97 |
| MDA-MB-468 | 88.78 | -8.02 |

Compound 26

Fig. 52

| Panel/Cell Line | Growth % | [Mean Growth Percent - Growth Percent] |
|---|---|---|
| Leukemia | | |
| CCRF-CEM | 2.75 | 21.62 |
| HL-60(TB) | 31.22 | -6.85 |
| K-562 | 3.51 | 20.86 |
| MOLT-4 | -3.07 | 27.44 |
| SR | 1.96 | 22.41 |
| Non-Small Cell Lung Cancer | | |
| A549/ATCC | 76.61 | -52.24 |
| EKVX | 90.66 | -66.29 |
| HOP-62 | -31.32 | 55.69 |
| HOP-92 | 69.14 | -44.77 |
| NCI-H226 | 88.71 | -64.34 |
| NCI-H23 | 27.19 | -2.82 |
| NCI-H322M | 29.72 | -5.35 |
| NCI-H460 | -44.42 | 68.79 |
| NCI-H522 | -50.49 | 74.86 |
| Colon Cancer | | |
| COLO 205 | -69.92 | 94.29 |
| HCC-2998 | -84.69 | 109.06 |
| HCT-116 | -58.24 | 82.61 |
| HCT-15 | 80.42 | -56.05 |
| HT29 | 18.63 | 5.74 |
| KM12 | -19.35 | 43.72 |
| SW-620 | -95.24 | 119.61 |
| CNS Cancer | | |
| SF-268 | 18.23 | 6.14 |
| SF-295 | 102.2 | -77.83 |
| SF-539 | 94.12 | -69.75 |
| SNB-19 | 92.12 | -67.75 |
| SNB-75 | 44.37 | -20 |
| U251 | -31.96 | 56.33 |

Compound 27

Fig. 53

Compound 27  Fig. 54

| Panel/Cell Line | Growth % | [Mean Growth Percent - Growth Percent] |
|---|---|---|
| Leukemia | | |
| CCRF-CEM | 39.92 | 20.91 |
| HL-60(TB) | 72.17 | -11.34 |
| MOLT-4 | 35.78 | 25.05 |
| RPMI-8226 | 91.89 | -31.06 |
| SR | -11.05 | 71.88 |
| Non-Small Cell Lung Cancer | | |
| A549/ATCC | 70.02 | -9.19 |
| EKVX | 107.7 | -46.87 |
| HOP-62 | 74.99 | -14.16 |
| NCI-H226 | 100.5 | -39.67 |
| NCI-H23 | 93.48 | -32.65 |
| NCI-H322M | 84.75 | -23.92 |
| NCI-H460 | 4.31 | 56.52 |
| NCI-H522 | 86.73 | -25.9 |
| Colon Cancer | | |
| COLO 205 | -16.04 | 76.87 |
| HCC-2998 | -61.75 | 122.58 |
| HCT-116 | -72.26 | 133.09 |
| HT29 | 54.41 | 6.42 |
| KM12 | 27.3 | 33.53 |
| SW-620 | -16.11 | 76.94 |
| CNS Cancer | | |
| SF-268 | 75.21 | -14.38 |
| SF-295 | 97.15 | -36.32 |
| SF-539 | 69.56 | -8.73 |
| SNB-19 | 71.28 | -10.45 |
| SNB-75 | 74.2 | -13.37 |
| U251 | 14.85 | 45.98 |

Compound 35

Fig. 55

Compound 35　　Fig. 56

Compound 36

Compound 36

Compound 37  Fig. 59

Compound 37

| Panel/Cell Line | Growth % | [Mean Growth Percent - Growth Percent] |
|---|---|---|
| Leukemia | | |
| CCRF-CEM | -20.6 | -7.9 |
| HL-60(TB) | -24.53 | -3.97 |
| MOLT-4 | -42.85 | 14.35 |
| RPMI-8226 | 35.43 | -63.93 |
| SR | -37.98 | 9.48 |
| Non-Small Cell Lung Cancer | | |
| A549/ATCC | -34.67 | 6.17 |
| HOP-62 | -94.52 | 66.02 |
| NCI-H226 | 92.46 | -121 |
| NCI-H23 | -22.34 | -6.16 |
| NCI-H322M | -60.99 | 32.49 |
| NCI-H460 | -15.66 | -12.84 |
| NCI-H522 | -0.37 | -28.13 |
| Colon Cancer | | |
| COLO 205 | -79.56 | 51.06 |
| HCC-2998 | -89.09 | 60.59 |
| HCT-116 | -97.29 | 68.79 |
| HCT-15 | 5.75 | -34.25 |
| HT29 | -25.8 | -2.7 |
| KM12 | -79.08 | 50.58 |
| SW-620 | -66.31 | 37.81 |
| CNS Cancer | | |
| SF-268 | -80.22 | 51.72 |
| SF-295 | -74.65 | 46.15 |
| SF-539 | 28.29 | -56.79 |
| SNB-19 | -6.48 | -22.02 |
| SNB-75 | -1.37 | -27.13 |
| U251 | -91.91 | 63.41 |

Compound 38

Fig. 61

| Panel/Cell Line | Growth % | | [Mean Growth Percent - Growth Percent] |
|---|---|---|---|
| Melanoma | | | |
| LOX IMVI | -90.8 | 62.3 | |
| MALME-3M | -50.19 | 21.69 | |
| M14 | -90.85 | 62.35 | |
| MDA-MB-435 | -48.07 | 19.57 | |
| SK-MEL-2 | 62.41 | -90.91 | |
| SK-MEL-28 | -49.6 | 21.1 | |
| SK-MEL-5 | 20.91 | -49.41 | |
| UACC-257 | 90.51 | -119 | |
| UACC-62 | 75.76 | -104.3 | |
| Ovarian Cancer | | | |
| IGROV1 | -73.66 | 45.16 | |
| OVCAR-3 | -61.57 | 33.07 | |
| OVCAR-4 | -95.48 | 66.98 | |
| OVCAR-5 | 33.38 | -61.88 | |
| OVCAR-8 | -62.84 | 34.34 | |
| NCI/ADR-RES | -64.12 | 35.62 | |
| SK-OV-3 | -37.2 | 8.7 | |
| Renal Cancer | | | |
| 786-0 | -97.95 | 69.45 | |
| A498 | 120.87 | -149.4 | |
| ACHN | -39.66 | 11.16 | |
| CAKI-1 | -72.82 | 44.32 | |
| RXF 393 | -95.63 | 67.13 | |
| SN12C | 40.33 | -68.83 | |
| TK-10 | 88.37 | -116.9 | |
| UO-31 | -37.81 | 9.31 | |
| Prostate Cancer | | | |
| PC-3 | -31.45 | 2.95 | |
| DU-145 | 10.71 | -39.21 | |
| Breast Cancer | | | |
| MCF7 | -90.43 | 61.93 | |
| MDA-MB- | -28.43 | -0.07 | |
| HS 578T | 29.84 | -58.34 | |
| BT-549 | 41.65 | -70.15 | |
| T-47D | -51.62 | 23.12 | |
| MDA-MB-468 | -84.53 | 56.03 | |

Compound 38

Fig. 62

Compound 39      Fig. 63

| Panel/Cell Line | Growth % | [Mean Growth Percent - Growth Percent] |
|---|---|---|
| Melanoma | | |
| LOX IMVI | -80.1 | 120.11 |
| MALME-3M | 71.74 | -31.73 |
| M14 | -24.02 | 64.03 |
| MDA-MB-435 | -21.39 | 61.4 |
| SK-MEL-2 | 71.65 | -31.64 |
| SK-MEL-28 | 82.86 | -42.85 |
| SK-MEL-5 | 83.74 | -43.73 |
| UACC-257 | 118.52 | -78.51 |
| UACC-62 | 93.09 | -53.08 |
| Ovarian Cancer | | |
| IGROV1 | -53.14 | 93.15 |
| OVCAR-3 | 31.67 | 8.34 |
| OVCAR-4 | 57.86 | -17.85 |
| OVCAR-5 | 72.81 | -32.8 |
| OVCAR-8 | 72.06 | -32.05 |
| NCI/ADR-RES | 66.92 | -26.91 |
| SK-OV-3 | 52.93 | -12.92 |
| Renal Cancer | | |
| 786-0 | 59.77 | -19.76 |
| A498 | 117.43 | -77.42 |
| ACHN | 79.62 | -39.61 |
| CAKI-1 | 31.27 | 8.74 |
| RXF 393 | -10.65 | 50.66 |
| SN12C | 65.79 | -25.78 |
| TK-10 | 93.52 | -53.51 |
| UO-31 | 27.94 | 12.07 |
| Prostate Cancer | | |
| PC-3 | 26.75 | 13.26 |
| DU-145 | 73.08 | -33.07 |
| Breast Cancer | | |
| MCF7 | 4.37 | 35.64 |
| MDA-MB- | 40.7 | -0.69 |
| HS 578T | 81.72 | -41.71 |
| BT-549 | 109.39 | -69.38 |
| T-47D | 56.09 | -16.08 |
| MDA-MB-468 | -12.6 | 52.61 |

Compound 39

Fig. 64

| Panel/Cell Line | Growth % | | [Mean Growth Percent - Growth Percent] |
|---|---|---|---|
| Leukemia | | | |
| CCRF-CEM | -29.71 | -25.58 | |
| HL-60(TB) | -57.34 | 2.05 | |
| MOLT-4 | -58.59 | 3.3 | |
| RPMI-8226 | -23.23 | -32.06 | |
| SR | -53.33 | -1.96 | |
| Non-Small Cell Lung Cancer | | | |
| A549/ATCC | -85.26 | 29.97 | |
| EKVX | -53.35 | -1.94 | |
| HOP-62 | -98.95 | 43.66 | |
| NCI-H226 | 50.2 | -105.5 | |
| NCI-H23 | -20.71 | -34.58 | |
| NCI-H322M | -76.34 | 21.05 | |
| NCI-H460 | 0.55 | -55.84 | |
| NCI-H522 | -81.56 | 26.27 | |
| Colon Cancer | | | |
| COLO 205 | -94.52 | 39.23 | |
| HCC-2998 | -90.92 | 35.63 | |
| HCT-116 | -99.95 | 44.66 | |
| HCT-15 | -10.87 | -44.42 | |
| HT29 | -77.24 | 21.95 | |
| KM12 | -88.12 | 32.83 | |
| SW-620 | -46.01 | -9.28 | |
| CNS Cancer | | | |
| SF-268 | -83.09 | 27.8 | |
| SF-295 | -83.84 | 28.55 | |
| SF-539 | -94.37 | 39.08 | |
| SNB-19 | -74.64 | 19.35 | |
| SNB-75 | -61.37 | 6.08 | |
| U251 | -95.75 | 40.46 | |

Compound 40

Fig. 65

| Panel/Cell Line | Growth % | [Mean Growth Percent - Growth Percent] |
|---|---|---|
| Melanoma | | |
| LOX IMVI | -86.88 | 31.59 |
| MALME-3M | -56.48 | 1.19 |
| M14 | -94.71 | 39.42 |
| MDA-MB-435 | -76.23 | 20.94 |
| SK-MEL-2 | -51.97 | -3.32 |
| SK-MEL-28 | -89.15 | 33.86 |
| SK-MEL-5 | 19.09 | -74.38 |
| UACC-257 | 99 | -154.3 |
| UACC-62 | -15.33 | -39.96 |
| Ovarian Cancer | | |
| IGROV1 | -79.9 | 24.61 |
| OVCAR-3 | -85.37 | 30.08 |
| OVCAR-4 | -98.92 | 43.63 |
| OVCAR-5 | -70.82 | 15.53 |
| OVCAR-8 | -51.94 | -3.35 |
| NCI/ADR-RES | 18.66 | -73.95 |
| SK-OV-3 | -56.91 | 1.62 |
| Renal Cancer | | |
| 786-0 | -95.29 | 40 |
| A498 | 117.07 | -172.4 |
| ACHN | -97.58 | 42.29 |
| CAKI-1 | -79.72 | 24.43 |
| RXF 393 | -97.14 | 41.85 |
| SN12C | -70.72 | 15.43 |
| TK-10 | 51.22 | -106.5 |
| U0-31 | -91.5 | 36.21 |
| Prostate Cancer | | |
| DU-145 | -57.66 | 2.37 |
| Breast Cancer | | |
| MCF7 | -93.29 | 38 |
| MDA-MB- | -69.56 | 14.27 |
| HS 578T | 11.96 | -67.25 |
| T-47D | -66.96 | 11.67 |
| MDA-MB-468 | -90.74 | 35.45 |

Compound 40

Fig. 66

Compound 41 Fig. 67

| Panel/Cell Line | Growth % | | [Mean Growth Percent - Growth Percent] |
|---|---|---|---|
| Melanoma | | | |
| LOX IMVI | 93.58 | -1.58 | |
| MALME-3M | 105.4 | -13.4 | |
| M14 | 101.42 | -9.42 | |
| MDA-MB-435 | 98.27 | -6.27 | |
| SK-MEL-2 | 82.28 | 9.72 | |
| SK-MEL-28 | 98.24 | -6.24 | |
| SK-MEL-5 | 95.56 | -3.56 | |
| UACC-257 | 102.46 | -10.46 | |
| UACC-62 | 103.07 | -11.07 | |
| Ovarian Cancer | | | |
| IGROV1 | 102.27 | -10.27 | |
| OVCAR-3 | 94.78 | -2.78 | |
| OVCAR-4 | 105.32 | -13.32 | |
| OVCAR-5 | 106.08 | -14.08 | |
| OVCAR-8 | 89.67 | 2.33 | |
| NCI/ADR-RES | 99.23 | -7.23 | |
| Renal Cancer | | | |
| 786-0 | 99.17 | -7.17 | |
| ACHN | 92.64 | -0.64 | |
| CAKI-1 | 78.93 | 13.07 | |
| RXF 393 | 83.07 | 8.93 | |
| SN12C | 99.37 | -7.37 | |
| TK-10 | 99.41 | -7.41 | |
| UO-31 | 71.72 | 20.28 | |
| Prostate Cancer | | | |
| PC-3 | 84.32 | 7.68 | |
| DU-145 | 67.05 | 24.95 | |
| Breast Cancer | | | |
| MCF7 | 93.36 | -1.36 | |
| MDA-MB- | 111.94 | -19.94 | |
| HS 578T | 96.52 | -4.52 | |
| BT-549 | 108.17 | -16.17 | |
| T-47D | 85.15 | 6.85 | |
| MDA-MB-468 | 91.89 | 0.11 | |

Compound 41

Fig. 68

| Panel/Cell Line | Growth % | | [Mean Growth Percent - Growth Percent] |
|---|---|---|---|
| Leukemia | | | |
| CCRF-CEM | 49.47 | 35.56 | |
| HL-60(TB) | 62.69 | 22.34 | |
| K-562 | 45.42 | 39.61 | |
| MOLT-4 | 67.6 | 17.43 | |
| RPMI-8226 | 63.22 | 21.81 | |
| SR | 3.3 | 81.73 | |
| Non-Small Cell Lung Cancer | | | |
| A549/ATCC | 59.89 | 25.14 | |
| EKVX | 87.12 | -2.09 | |
| HOP-62 | 107.07 | -22.04 | |
| NCI-H226 | 89.76 | -4.73 | |
| NCI-H23 | 90.79 | -5.76 | |
| NCI-H322M | 104.32 | -19.29 | |
| NCI-H460 | 91.64 | -6.61 | |
| NCI-H522 | 86.01 | -0.98 | |
| Colon Cancer | | | |
| COLO 205 | 79.3 | 5.73 | |
| HCC-2998 | 98.55 | -13.52 | |
| HCT-116 | 65.56 | 19.47 | |
| HCT-15 | 96.9 | -11.87 | |
| HT29 | 48.33 | 36.7 | |
| KM12 | 87.19 | -2.16 | |
| SW-620 | 104.09 | -19.06 | |
| CNS Cancer | | | |
| SF-268 | 97.66 | -12.63 | |
| SF-295 | 114 | -28.97 | |
| SF-539 | 98.34 | -13.31 | |
| SNB-19 | 98.88 | -13.85 | |
| SNB-75 | 74.55 | 10.48 | |
| U251 | 74 | 11.03 | |

Compound 42

Fig. 69

| Panel/Cell Line | Growth % | [Mean Growth Percent - Growth Percent] |
|---|---|---|
| Melanoma | | |
| LOX IMVI | 87.32 | -2.29 |
| MALME-3M | 100.58 | -15.55 |
| M14 | 94.89 | -9.86 |
| MDA-MB-435 | 101.08 | -16.05 |
| SK-MEL-2 | 86.39 | -1.36 |
| SK-MEL-28 | 99.86 | -14.83 |
| SK-MEL-5 | 85.24 | -0.21 |
| UACC-257 | 81.43 | 3.6 |
| UACC-62 | 109.12 | -24.09 |
| Ovarian Cancer | | |
| IGROV1 | 80.06 | 4.97 |
| OVCAR-3 | 94.31 | -9.28 |
| OVCAR-4 | 92.12 | -7.09 |
| OVCAR-5 | 104.97 | -19.94 |
| OVCAR-8 | 74.59 | 10.44 |
| NCI/ADR-RES | 99.88 | -14.85 |
| Renal Cancer | | |
| 786-0 | 85.28 | -0.25 |
| ACHN | 99.13 | -14.1 |
| CAKI-1 | 77.91 | 7.12 |
| RXF 393 | 52.58 | 32.45 |
| SN12C | 92.74 | -7.71 |
| TK-10 | 101.19 | -16.16 |
| UO-31 | 61.87 | 23.16 |
| Prostate Cancer | | |
| PC-3 | 88.73 | -3.7 |
| DU-145 | 100.44 | -15.41 |
| Breast Cancer | | |
| MCF7 | 59.2 | 25.83 |
| MDA-MB- | 119.03 | -34 |
| HS 578T | 99.03 | -14 |
| BT-549 | 102.25 | -17.22 |
| T-47D | 86.07 | -1.04 |
| MDA-MB-468 | 83.85 | 1.18 |

Compound 42

Fig. 70

| Panel/Cell Line | Growth % | | [Mean Growth Percent - Growth Percent] |
|---|---|---|---|
| Leukemia | | | |
| CCRF-CEM | 95.17 | 3.4 | |
| HL-60(TB) | 95.05 | 3.52 | |
| K-562 | 80.52 | 18.05 | |
| MOLT-4 | 90.51 | 8.06 | |
| RPMI-8226 | 87.01 | 11.56 | |
| SR | 67.15 | 31.42 | |
| Non-Small Cell Lung Cancer | | | |
| A549/ATCC | 86.48 | 12.09 | |
| EKVX | 104.9 | -6.33 | |
| HOP-62 | 103.79 | -5.22 | |
| HOP-92 | 107.14 | -8.57 | |
| NCI-H226 | 93.26 | 5.31 | |
| NCI-H23 | 103.8 | -5.23 | |
| NCI-H322M | 90.73 | 7.84 | |
| NCI-H460 | 103.04 | -4.47 | |
| NCI-H522 | 69.49 | 29.08 | |
| Colon Cancer | | | |
| COLO 205 | 97.55 | 1.02 | |
| HCC-2998 | 101.79 | -3.22 | |
| HCT-116 | 102.04 | -3.47 | |
| HCT-15 | 100.29 | -1.72 | |
| HT29 | 84.38 | 14.19 | |
| KM12 | 90.4 | 8.17 | |
| SW-620 | 109.06 | -10.49 | |
| CNS Cancer | | | |
| SF-268 | 115.97 | -17.4 | |
| SF-295 | 93.5 | 5.07 | |
| SF-539 | 110.57 | -12 | |
| SNB-19 | 104.48 | -5.91 | |
| SNB-75 | 94.62 | 3.95 | |
| U251 | 90.33 | 8.24 | |

Compound 43

Fig. 71

| Panel/Cell Line | Growth % | | [Mean Growth Percent - Growth Percent] |
|---|---|---|---|
| Melanoma | | | |
| LOX IMVI | 100.04 | -1.47 | |
| MALME-3M | 100.8 | -2.23 | |
| M14 | 112.56 | -13.99 | |
| MDA-MB-435 | 100.36 | -1.79 | |
| SK-MEL-2 | 76.79 | 21.78 | |
| SK-MEL-28 | 109.88 | -11.31 | |
| SK-MEL-5 | 92.84 | 5.73 | |
| UACC-257 | 104.02 | -5.45 | |
| UACC-62 | 89.51 | 9.06 | |
| Ovarian Cancer | | | |
| IGROV1 | 101.91 | -3.34 | |
| OVCAR-3 | 108.53 | -9.96 | |
| OVCAR-4 | 106.65 | -8.08 | |
| OVCAR-5 | 114.32 | -15.75 | |
| OVCAR-8 | 100.2 | -1.63 | |
| NCI/ADR-RES | 97.92 | 0.65 | |
| Renal Cancer | | | |
| 786-0 | 110.11 | -11.54 | |
| ACHN | 104.6 | -6.03 | |
| CAKI-1 | 96.25 | 2.32 | |
| RXF 393 | 92.54 | 6.03 | |
| SN12C | 97.36 | 1.21 | |
| TK-10 | 107.5 | -8.93 | |
| UO-31 | 77.66 | 20.91 | |
| Prostate Cancer | | | |
| PC-3 | 81.27 | 17.3 | |
| DU-145 | 109.33 | -10.76 | |
| Breast Cancer | | | |
| MCF7 | 100.26 | -1.69 | |
| MDA-MB- | 118.88 | -20.31 | |
| HS 578T | 103.41 | -4.84 | |
| BT-549 | 126.66 | -28.09 | |
| T-47D | 95.82 | 2.75 | |
| MDA-MB-468 | 105.86 | -7.29 | |

Compound 43

Fig. 72

| Panel/Cell Line | Growth % | | [Mean Growth Percent - Growth Percent] |
|---|---|---|---|
| Leukemia | | | |
| CCRF-CEM | 13.59 | 54.18 | |
| HL-60(TB) | 27.6 | 40.17 | |
| K-562 | 47.38 | 20.39 | |
| MOLT-4 | 48.51 | 19.26 | |
| RPMI-8226 | 15.79 | 51.98 | |
| SR | -19.57 | 87.34 | |
| Non-Small Cell Lung Cancer | | | |
| A549/ATCC | 47.63 | 20.14 | |
| EKVX | 77.59 | -9.82 | |
| HOP-62 | 86.87 | -19.1 | |
| NCI-H226 | 80.64 | -12.87 | |
| NCI-H23 | 77.26 | -9.49 | |
| NCI-H322M | 85.99 | -18.22 | |
| NCI-H460 | 48.24 | 19.53 | |
| NCI-H522 | 36.67 | 31.1 | |
| Colon Cancer | | | |
| COLO 205 | 71.17 | -3.4 | |
| HCC-2998 | 68.72 | -0.95 | |
| HCT-116 | 51.63 | 16.14 | |
| HCT-15 | 82.89 | -15.12 | |
| HT29 | 49.49 | 18.28 | |
| KM12 | 61.07 | 6.7 | |
| SW-620 | 95.23 | -27.46 | |
| CNS Cancer | | | |
| SF-268 | 98.67 | -30.9 | |
| SF-295 | 93.27 | -25.5 | |
| SF-539 | 101.87 | -34.1 | |
| SNB-19 | 92.68 | -24.91 | |
| SNB-75 | 97.74 | -29.97 | |
| U251 | 59.12 | 8.65 | |

Compound 44

Fig. 73

| Panel/Cell Line | Growth % | | [Mean Growth Percent - Growth Percent] |
|---|---|---|---|
| Melanoma | | | |
| LOX IMVI | 67.09 | 0.68 | |
| MALME-3M | 106.37 | -38.6 | |
| M14 | 90.87 | -23.1 | |
| MDA-MB-435 | 71.52 | -3.75 | |
| SK-MEL-2 | 15.34 | 52.43 | |
| SK-MEL-28 | 75.32 | -7.55 | |
| SK-MEL-5 | 58.08 | 9.69 | |
| UACC-257 | 64.26 | 3.51 | |
| UACC-62 | 67.23 | 0.54 | |
| Ovarian Cancer | | | |
| IGROV1 | 72.51 | -4.74 | |
| OVCAR-3 | 89.47 | -21.7 | |
| OVCAR-4 | 77.5 | -9.73 | |
| OVCAR-5 | 101.96 | -34.19 | |
| OVCAR-8 | 11.65 | 56.12 | |
| NCI/ADR-RES | 79.88 | -12.11 | |
| Renal Cancer | | | |
| 786-0 | 97.05 | -29.28 | |
| ACHN | 91.31 | -23.54 | |
| CAKI-1 | 78.3 | -10.53 | |
| RXF 393 | 34.39 | 33.38 | |
| SN12C | 71.85 | -4.08 | |
| TK-10 | 58.38 | 9.39 | |
| UO-31 | 51.72 | 16.05 | |
| Prostate Cancer | | | |
| PC-3 | 58.5 | 9.27 | |
| DU-145 | 85.43 | -17.66 | |
| Breast Cancer | | | |
| MCF7 | 26.27 | 41.5 | |
| MDA-MB- | 99.79 | -32.02 | |
| HS 578T | 93.19 | -25.42 | |
| BT-549 | 113.88 | -46.11 | |
| T-47D | 78.54 | -10.77 | |
| MDA-MB-468 | 77.36 | -9.59 | |

Compound 44

Fig. 74

|  | GI50 | TGI | LC50 |
|---|---|---|---|
| Leukemia | | | |
| CCRF-CEM | 3.08E-7 | 9.57E-7 | > 1.00E-4 |
| HL-60(TB) | 3.49E-7 | 1.18E-6 | 6.05E-6 |
| MOLT-4 | 2.37E-7 | 6.02E-7 | 5.66E-6 |
| RPMI-8226 | 3.24E-7 | 1.26E-6 | > 1.00E-4 |
| SR | 2.17E-7 | 6.67E-7 | > 1.00E-4 |
| Non-Small Cell Lung Cancer | | | |
| A549/ATCC | 1.57E-6 | 3.13E-6 | 6.22E-6 |
| EKVX | 1.69E-6 | 3.25E-6 | 6.23E-6 |
| HOP-62 | 1.82E-6 | 3.41E-6 | 6.38E-6 |
| HOP-92 | 2.69E-7 | 1.73E-6 | 4.65E-6 |
| NCI-H226 | 2.21E-6 | 5.56E-6 | > 1.00E-4 |
| NCI-H23 | 1.51E-6 | 3.08E-6 | 6.30E-6 |
| NCI-H322M | 1.85E-6 | 3.51E-6 | 6.67E-6 |
| NCI-H460 | 6.18E-7 | 2.30E-6 | 6.96E-6 |
| NCI-H522 | 1.81E-6 | 3.62E-6 | 7.23E-6 |
| Colon Cancer | | | |
| COLO 205 | 2.00E-6 | 3.60E-6 | 6.49E-6 |
| HCC-2998 | 6.26E-7 | 2.08E-6 | 5.30E-6 |
| HCT-116 | 5.76E-7 | 1.82E-6 | 4.54E-6 |
| HCT-15 | 4.03E-6 | 4.77E-5 | > 1.00E-4 |
| HT29 | 1.84E-6 | 3.51E-6 | 6.67E-6 |
| KM12 | 6.99E-7 | 2.43E-6 | 7.37E-6 |
| SW-620 | 4.80E-7 | 1.99E-6 | 6.18E-6 |
| CNS Cancer | | | |
| SF-268 | 1.67E-6 | 3.57E-6 | 7.67E-6 |
| SF-295 | 1.88E-6 | 3.71E-6 | 7.35E-6 |
| SF-539 | 1.83E-6 | 3.40E-6 | 6.32E-6 |
| SNB-19 | 1.61E-6 | 3.05E-6 | 5.79E-6 |
| SNB-75 | 1.67E-6 | 6.13E-6 | > 1.00E-4 |
| U251 | 1.51E-6 | 2.94E-6 | 5.72E-6 |

Compound 8  Fig. 75

|  | GI50 | TGI | LC50 |
|---|---|---|---|
| Melanoma | | | |
| LOX IMVI | 3.37E-7 | 1.34E-6 | 4.49E-6 |
| MALME-3M | 2.13E-6 | 3.94E-6 | 7.31E-6 |
| M14 | 1.89E-6 | 3.53E-6 | 6.61E-6 |
| MDA-MB-435 | 1.20E-6 | 2.50E-6 | 5.18E-6 |
| SK-MEL-2 | 2.30E-6 | 4.30E-6 | 8.03E-6 |
| SK-MEL-28 | 2.01E-6 | 4.30E-6 | 9.16E-6 |
| UACC-257 | 2.24E-6 | 6.12E-6 | > 1.00E-4 |
| UACC-62 | 1.48E-6 | 2.91E-6 | 5.74E-6 |
| Ovarian Cancer | | | |
| IGROV1 | 1.56E-6 | 3.06E-6 | 6.01E-6 |
| OVCAR-3 | 1.39E-6 | 2.81E-6 | 5.68E-6 |
| OVCAR-4 | 1.54E-6 | 2.95E-6 | 5.65E-6 |
| OVCAR-5 | 2.17E-6 | 4.50E-6 | 9.30E-6 |
| OVCAR-8 | 1.40E-6 | 3.22E-6 | 7.40E-6 |
| NCI/ADR-RES | 2.56E-6 | 1.28E-5 | > 1.00E-4 |
| SK-OV-3 | 1.93E-6 | 3.55E-6 | 6.54E-6 |
| Renal Cancer | | | |
| 786-0 | 1.52E-6 | 2.92E-6 | 5.61E-6 |
| A498 | 1.31E-6 | 2.61E-6 | 5.20E-6 |
| ACHN | 1.88E-6 | 3.48E-6 | 6.44E-6 |
| CAKI-1 | 1.60E-6 | 3.53E-6 | 7.78E-6 |
| RXF 393 | 1.22E-6 | 2.55E-6 | 5.33E-6 |
| SN12C | 1.46E-6 | 2.89E-6 | 5.70E-6 |
| TK-10 | 1.71E-6 | 3.32E-6 | 6.45E-6 |
| UO-31 | 1.51E-6 | 2.93E-6 | 5.68E-6 |
| Prostate Cancer | | | |
| PC-3 | 5.81E-7 | 2.06E-6 | 5.16E-6 |
| DU-145 | 1.89E-6 | 3.34E-6 | 5.89E-6 |
| Breast Cancer | | | |
| MCF7 | 1.59E-6 | 3.01E-6 | 5.71E-6 |
| MDA-MB-231/ATCC | 1.63E-6 | 3.07E-6 | 5.78E-6 |
| HS 578T | 1.51E-6 | 3.87E-6 | |
| BT-549 | 1.89E-6 | 3.52E-6 | 6.55E-6 |
| T-47D | 2.18E-6 | 5.23E-6 | 2.67E-5 |
| MDA-MB-468 | 1.41E-6 | 2.82E-6 | 5.64E-6 |

Compound 8      Fig. 76

|  | GI50 | TGI | LC50 |
|---|---|---|---|
| Leukemia | | | |
| CCRF-CEM | 2.59E-6 | . | > 1.00E-4 |
| HL-60(TB) | 2.19E-6 | 5.88E-6 | > 1.00E-4 |
| MOLT-4 | 1.92E-6 | . | > 1.00E-4 |
| RPMI-8226 | 2.16E-6 | . | > 1.00E-4 |
| SR | 1.04E-6 | . | > 1.00E-4 |
| Non-Small Cell Lung Cancer | | | |
| A549/ATCC | 1.89E-6 | 3.63E-6 | . |
| EKVX | 5.11E-6 | 2.55E-5 | > 1.00E-4 |
| HOP-62 | 1.78E-6 | 3.30E-6 | 6.11E-6 |
| HOP-92 | 1.46E-6 | 3.19E-6 | . |
| NCI-H226 | 2.31E-6 | 7.51E-6 | 9.51E-5 |
| NCI-H23 | 1.88E-6 | 3.83E-6 | . |
| NCI-H322M | 1.87E-6 | . | . |
| NCI-H460 | 1.93E-6 | . | . |
| NCI-H522 | 1.79E-6 | 3.70E-6 | . |
| Colon Cancer | | | |
| COLO 205 | 1.98E-6 | 3.48E-6 | 6.12E-6 |
| HCC-2998 | 1.74E-6 | 3.47E-6 | . |
| HCT-116 | 1.79E-6 | 3.33E-6 | . |
| HCT-15 | 1.97E-6 | 3.84E-6 | . |
| HT29 | 1.78E-6 | 3.29E-6 | . |
| KM12 | 2.10E-6 | . | . |
| SW-620 | 1.83E-6 | 3.69E-6 | . |
| CNS Cancer | | | |
| SF-268 | 2.04E-6 | . | . |
| SF-295 | 1.76E-6 | 3.73E-6 | 7.87E-6 |
| SF-539 | 1.93E-6 | 3.60E-6 | 6.73E-6 |
| SNB-19 | 1.64E-6 | 3.17E-6 | . |
| SNB-75 | 1.29E-6 | 4.16E-6 | 2.27E-5 |
| U251 | 1.72E-6 | 3.26E-6 | . |

Compound 13        Fig. 77

|  | GI50 | TGI | LC50 |
|---|---|---|---|
| Melanoma | | | |
| LOX IMVI | 1.69E-6 | 3.34E-6 | |
| MALME-3M | 2.10E-6 | 4.09E-6 | |
| M14 | 1.92E-6 | 3.63E-6 | |
| MDA-MB-435 | 1.65E-6 | 3.12E-6 | |
| SK-MEL-2 | 2.27E-6 | 4.25E-6 | |
| SK-MEL-28 | 1.78E-6 | 3.33E-6 | 6.23E-6 |
| UACC-257 | 1.79E-6 | 3.84E-6 | 8.23E-6 |
| UACC-62 | 1.81E-6 | 4.03E-6 | 8.99E-6 |
| Ovarian Cancer | | | |
| IGROV1 | 1.81E-6 | | |
| OVCAR-3 | 2.11E-6 | | |
| OVCAR-4 | 1.64E-6 | 3.09E-6 | 5.82E-6 |
| OVCAR-5 | 1.77E-6 | 3.63E-6 | 7.44E-6 |
| OVCAR-8 | 1.95E-6 | 4.06E-6 | |
| NCI/ADR-RES | 1.96E-6 | 4.23E-6 | |
| SK-OV-3 | 1.98E-6 | 3.61E-6 | 6.59E-6 |
| Renal Cancer | | | |
| 786-0 | 1.86E-6 | 3.64E-6 | |
| A498 | 1.46E-6 | 3.15E-6 | |
| ACHN | 1.75E-6 | 3.19E-6 | 5.79E-6 |
| CAKI-1 | 2.33E-6 | 7.02E-6 | 4.49E-5 |
| RXF 393 | 1.20E-6 | 2.53E-6 | 5.35E-6 |
| SN12C | 1.67E-6 | 3.25E-6 | 6.34E-6 |
| TK-10 | 2.06E-6 | 4.36E-6 | |
| UO-31 | 1.47E-6 | 3.01E-6 | |
| Prostate Cancer | | | |
| PC-3 | 1.63E-6 | | |
| DU-145 | 1.90E-6 | 3.41E-6 | |
| Breast Cancer | | | |
| MCF7 | 1.66E-6 | 3.21E-6 | 6.24E-6 |
| MDA-MB-231/A | 1.63E-6 | 3.23E-6 | 6.41E-6 |
| HS 578T | 2.03E-6 | | > 1.00E-4 |
| BT-549 | 2.00E-6 | 3.74E-6 | |
| T-47D | 2.01E-6 | 4.18E-6 | 8.69E-6 |
| MDA-MB-468 | 1.56E-6 | 3.11E-6 | 6.19E-6 |

Compound 13          Fig. 78

| Panel/Cell Line | GI50 | TGI | LC50 |
|---|---|---|---|
| Leukemia | | | |
| CCRF-CEM | 6.25E-6 | 1.53E-5 | > 2.50E-5 |
| HL-60(TB) | 3.08E-6 | 7.61E-6 | 1.88E-5 |
| MOLT-4 | 3.31E-6 | 8.49E-6 | 2.18E-5 |
| RPMI-8226 | 6.29E-6 | 1.74E-5 | > 2.50E-5 |
| SR | 8.93E-7 | 4.60E-6 | > 2.50E-5 |
| Non-Small Cell Lung Cancer | | | |
| A549/ATCC | 4.53E-6 | 8.61E-6 | 1.64E-5 |
| EKVX | 8.61E-6 | > 2.50E-5 | > 2.50E-5 |
| HOP-62 | 4.50E-6 | 8.24E-6 | 1.51E-5 |
| HOP-92 | 3.90E-6 | 9.49E-6 | 2.31E-5 |
| NCI-H226 | 5.91E-6 | 1.62E-5 | > 2.50E-5 |
| NCI-H23 | 5.07E-6 | 1.05E-5 | 2.17E-5 |
| NCI-H322M | 4.77E-6 | 9.73E-6 | 1.98E-5 |
| NCI-H460 | 3.79E-6 | 8.13E-6 | 1.75E-5 |
| NCI-H522 | 5.34E-6 | 1.06E-5 | 2.11E-5 |
| Colon Cancer | | | |
| COLO 205 | 4.81E-6 | 8.61E-6 | 1.54E-5 |
| HCC-2998 | 4.07E-6 | 7.99E-6 | 1.57E-5 |
| HCT-116 | 3.92E-6 | 7.65E-6 | 1.49E-5 |
| HCT-15 | 4.73E-6 | 8.87E-6 | 1.66E-5 |
| HT29 | 4.51E-6 | 8.40E-6 | 1.57E-5 |
| KM12 | 5.12E-6 | 9.74E-6 | 1.86E-5 |
| SW-620 | 4.68E-6 | 9.33E-6 | 1.86E-5 |
| CNS Cancer | | | |
| SF-268 | 4.62E-6 | 9.57E-6 | 1.98E-5 |
| SF-295 | 4.48E-6 | 8.98E-6 | 1.80E-5 |
| SF-539 | 6.29E-6 | 1.38E-5 | > 2.50E-5 |
| SNB-19 | 4.34E-6 | 8.26E-6 | 1.57E-5 |
| SNB-75 | 6.47E-6 | > 2.50E-5 | > 2.50E-5 |
| U251 | 4.56E-6 | 8.70E-6 | 1.66E-5 |

Compound 17

Fig. 79

| Panel/Cell Line | GI50 | TGI | LC50 |
|---|---|---|---|
| Melanoma | | | |
| LOX IMVI | 3.99E-6 | 7.77E-6 | 1.51E-5 |
| MALME-3M | 5.01E-6 | 1.06E-5 | 2.25E-5 |
| M14 | 4.84E-6 | 8.95E-6 | 1.66E-5 |
| MDA-MB-435 | 3.90E-6 | 7.36E-6 | 1.39E-5 |
| SK-MEL-2 | 5.32E-6 | 1.00E-5 | 1.89E-5 |
| SK-MEL-28 | 4.74E-6 | 8.87E-6 | 1.66E-5 |
| UACC-257 | 7.56E-6 | 2.48E-5 | > 2.50E-5 |
| UACC-62 | 4.43E-6 | 8.61E-6 | 1.67E-5 |
| | | | |
| Ovarian Cancer | | | |
| IGROV1 | 4.32E-6 | 8.46E-6 | 1.66E-5 |
| OVCAR-3 | 4.58E-6 | 8.45E-6 | 1.56E-5 |
| OVCAR-4 | 4.51E-6 | 8.16E-6 | 1.48E-5 |
| OVCAR-5 | 4.48E-6 | 9.11E-6 | 1.85E-5 |
| OVCAR-8 | 5.34E-6 | 1.17E-5 | > 2.50E-5 |
| NCI/ADR-RES | 4.88E-6 | 9.96E-6 | 2.03E-5 |
| SK-OV-3 | 5.02E-6 | 8.91E-6 | 1.58E-5 |
| | | | |
| Renal Cancer | | | |
| 786-0 | 4.50E-6 | 8.49E-6 | 1.60E-5 |
| A498 | 3.96E-6 | 8.36E-6 | 1.77E-5 |
| ACHN | 4.76E-6 | 8.91E-6 | 1.67E-5 |
| CAKI-1 | 4.51E-6 | 1.03E-5 | 2.35E-5 |
| RXF 393 | 3.60E-6 | 7.13E-6 | 1.41E-5 |
| SN12C | 4.46E-6 | 8.64E-6 | 1.67E-5 |
| TK-10 | 9.12E-6 | > 2.50E-5 | > 2.50E-5 |
| UO-31 | 3.82E-6 | 7.85E-6 | 1.61E-5 |
| | | | |
| Prostate Cancer | | | |
| PC-3 | 3.86E-6 | 8.06E-6 | 1.68E-5 |
| DU-145 | 4.77E-6 | 8.57E-6 | 1.54E-5 |
| Breast Cancer | | | |
| MCF7 | 4.50E-6 | 8.29E-6 | 1.53E-5 |
| MDA-MB-231/ATCC | 3.96E-6 | 8.36E-6 | 1.77E-5 |
| HS 578T | 5.13E-6 | 1.18E-5 | > 2.50E-5 |
| BT-549 | 7.75E-6 | > 2.50E-5 | > 2.50E-5 |
| T-47D | 4.85E-6 | 9.23E-6 | 1.75E-5 |
| MDA-MB-468 | 4.20E-6 | 8.60E-6 | 1.76E-5 |

Compound 17          Fig. 80

|  | GI50 | TGI | LC50 |
|---|---|---|---|
| Leukemia | | | |
| CCRF-CEM | 7.83E-6 | 1.94E-5 | > 3.33E-5 |
| HL-60(TB) | 6.26E-6 | 1.42E-5 | 3.21E-5 |
| MOLT-4 | 5.87E-6 | 1.38E-5 | 3.23E-5 |
| RPMI-8226 | 9.91E-6 | 3.20E-5 | > 3.33E-5 |
| SR | 4.00E-6 | 1.47E-5 | > 3.33E-5 |
| Non-Small Cell Lung Cancer | | | |
| A549/ATCC | 6.19E-6 | 1.27E-5 | 2.59E-5 |
| EKVX | 6.08E-6 | 1.20E-5 | 2.35E-5 |
| HOP-62 | 5.90E-6 | 1.19E-5 | 2.42E-5 |
| HOP-92 | 5.42E-6 | 1.12E-5 | 2.33E-5 |
| NCI-H226 | 6.19E-6 | 1.28E-5 | 2.65E-5 |
| NCI-H23 | 6.67E-6 | 1.35E-5 | 2.71E-5 |
| NCI-H322M | 6.35E-6 | 1.18E-5 | 2.20E-5 |
| NCI-H460 | 5.18E-6 | 1.14E-5 | 2.51E-5 |
| NCI-H522 | 7.08E-6 | 1.37E-5 | 2.66E-5 |
| Colon Cancer | | | |
| COLO 205 | 3.39E-6 | 8.23E-6 | 2.00E-5 |
| HCC-2998 | 2.53E-6 | 9.02E-6 | 2.75E-5 |
| HCT-116 | 5.25E-6 | 1.22E-5 | 2.81E-5 |
| HCT-15 | 6.24E-6 | 1.21E-5 | 2.33E-5 |
| HT29 | 3.74E-6 | 9.35E-6 | 2.34E-5 |
| KM12 | 7.41E-6 | 1.43E-5 | 2.78E-5 |
| SW-620 | 6.05E-6 | 1.23E-5 | 2.50E-5 |
| CNS Cancer | | | |
| SF-268 | 7.13E-6 | 1.42E-5 | 2.84E-5 |
| SF-295 | 6.12E-6 | 1.19E-5 | 2.30E-5 |
| SF-539 | 6.26E-6 | 1.12E-5 | 2.00E-5 |
| SNB-19 | 5.99E-6 | 1.24E-5 | 2.58E-5 |
| SNB-75 | 4.03E-6 | 8.94E-6 | 1.98E-5 |
| U251 | 5.71E-6 | 1.24E-5 | 2.68E-5 |

Compound 18      Fig. 81

|  | GI50 | TGI | LC50 |
|---|---|---|---|
| Melanoma | | | |
| LOX IMVI | 6.07E-6 | 2.11E-5 | > 3.33E-5 |
| MALME-3M | 6.90E-6 | 1.31E-5 | 2.49E-5 |
| M14 | 6.63E-6 | 1.31E-5 | 2.57E-5 |
| MDA-MB-435 | 5.80E-6 | 1.14E-5 | 2.26E-5 |
| SK-MEL-2 | 7.47E-6 | 1.43E-5 | 2.73E-5 |
| SK-MEL-28 | 5.89E-6 | 1.09E-5 | 2.03E-5 |
| UACC-257 | 6.97E-6 | 1.50E-5 | 3.22E-5 |
| UACC-62 | 5.87E-6 | 1.11E-5 | 2.10E-5 |
| Ovarian Cancer | | | |
| IGROV1 | 6.18E-6 | 1.23E-5 | 2.47E-5 |
| OVCAR-3 | 6.71E-6 | 1.26E-5 | 2.38E-5 |
| OVCAR-4 | 5.68E-6 | 1.22E-5 | 2.63E-5 |
| OVCAR-5 | 5.93E-6 | 1.10E-5 | 2.04E-5 |
| OVCAR-8 | 6.39E-6 | 1.44E-5 | 3.25E-5 |
| NCI/ADR-RES | 5.89E-6 | 1.26E-5 | 2.71E-5 |
| SK-OV-3 | 6.85E-6 | 1.25E-5 | 2.30E-5 |
| Renal Cancer | | | |
| 786-0 | 6.47E-6 | 1.36E-5 | 2.84E-5 |
| A498 | 5.76E-6 | 1.08E-5 | 2.02E-5 |
| ACHN | 5.74E-6 | 1.06E-5 | 1.96E-5 |
| CAKI-1 | 5.33E-6 | 1.07E-5 | 2.17E-5 |
| RXF 393 | 1.94E-6 | 7.83E-6 | 2.09E-5 |
| SN12C | 5.56E-6 | 1.08E-5 | 2.12E-5 |
| TK-10 | 5.98E-6 | 1.20E-5 | 2.39E-5 |
| UO-31 | 4.64E-6 | 9.93E-6 | 2.12E-5 |
| Prostate Cancer | | | |
| PC-3 | 5.71E-6 | 1.16E-5 | 2.35E-5 |
| DU-145 | 6.28E-6 | 1.14E-5 | 2.07E-5 |
| Breast Cancer | | | |
| MCF7 | 3.74E-6 | 9.54E-6 | 2.44E-5 |
| MDA-MB-231/ATCC | 5.87E-6 | 1.10E-5 | 2.08E-5 |
| HS 578T | 7.26E-6 | 1.64E-5 | > 3.33E-5 |
| BT-549 | 7.34E-6 | 1.47E-5 | 2.93E-5 |
| T-47D | 6.17E-6 | 1.27E-5 | 2.61E-5 |
| MDA-MB-468 | 4.14E-6 | 9.13E-6 | 2.01E-5 |

Compound 18      Fig. 82

| Panel/Cell Line | GI50 | TGI | LC50 |
|---|---|---|---|
| Leukemia | | | |
| CCRF-CEM | 3.32E-6 | 1.01E-5 | > 1.00E-4 |
| HL-60(TB) | 1.90E-6 | 3.91E-6 | 8.04E-6 |
| MOLT-4 | 2.32E-6 | 5.75E-6 | > 1.00E-4 |
| RPMI-8226 | 3.07E-6 | 1.84E-5 | > 1.00E-4 |
| SR | 2.30E-6 | 6.17E-6 | > 1.00E-4 |
| Non-Small Cell Lung Cancer | | | |
| A549/ATCC | 1.90E-6 | 3.78E-6 | 7.52E-6 |
| EKVX | 2.69E-6 | 8.27E-6 | 3.53E-5 |
| HOP-62 | 1.76E-6 | 3.35E-6 | 6.37E-6 |
| HOP-92 | 1.55E-6 | 3.34E-6 | 7.19E-6 |
| NCI-H226 | 2.00E-6 | 4.46E-6 | 9.94E-6 |
| NCI-H23 | 1.85E-6 | 3.59E-6 | 6.95E-6 |
| NCI-H322M | 2.71E-6 | 7.64E-6 | 3.26E-5 |
| NCI-H460 | 2.18E-6 | 4.54E-6 | |
| NCI-H522 | 2.08E-6 | 4.24E-6 | 8.64E-6 |
| Colon Cancer | | | |
| COLO 205 | 1.79E-6 | 3.29E-6 | 6.04E-6 |
| HCC-2998 | 1.48E-6 | 2.96E-6 | 5.91E-6 |
| HCT-116 | 1.76E-6 | 3.17E-6 | 5.73E-6 |
| HCT-15 | 1.93E-6 | 3.86E-6 | 7.70E-6 |
| HT29 | 1.85E-6 | 3.53E-6 | 6.72E-6 |
| KM12 | 2.07E-6 | 3.84E-6 | 7.13E-6 |
| SW-620 | 2.00E-6 | 4.04E-6 | 8.19E-6 |
| CNS Cancer | | | |
| SF-268 | 2.13E-6 | 4.00E-6 | |
| SF-295 | 2.01E-6 | 4.13E-6 | 8.47E-6 |
| SF-539 | 1.96E-6 | 3.63E-6 | 6.71E-6 |
| SNB-19 | 1.66E-6 | 3.26E-6 | 6.39E-6 |
| SNB-75 | 1.20E-6 | 2.87E-6 | 6.88E-6 |
| U251 | 1.67E-6 | 3.22E-6 | 6.19E-6 |

Compound 24                    Fig. 83

| Panel/Cell Line | GI50 | TGI | LC50 |
|---|---|---|---|
| Melanoma | | | |
| LOX IMVI | 1.77E-6 | 3.51E-6 | 6.95E-6 |
| MALME-3M | 2.03E-6 | 4.14E-6 | 8.43E-6 |
| M14 | 1.79E-6 | 3.37E-6 | 6.35E-6 |
| MDA-MB-435 | 1.66E-6 | 3.14E-6 | 5.95E-6 |
| SK-MEL-2 | 2.63E-6 | 4.97E-6 | |
| SK-MEL-28 | 1.75E-6 | 3.16E-6 | 5.72E-6 |
| UACC-257 | 5.58E-6 | 2.20E-5 | 6.75E-5 |
| UACC-62 | 1.64E-6 | 3.11E-6 | 5.90E-6 |
| | | | |
| Ovarian Cancer | | | |
| IGROV1 | 2.08E-6 | 4.31E-6 | 8.97E-6 |
| OVCAR-3 | 2.00E-6 | 3.53E-6 | 6.22E-6 |
| OVCAR-4 | 1.63E-6 | 3.03E-6 | 5.63E-6 |
| OVCAR-5 | 1.86E-6 | 3.52E-6 | 6.65E-6 |
| OVCAR-8 | 2.20E-6 | 5.69E-6 | > 1.00E-4 |
| NCI/ADR-RES | 2.02E-6 | 4.51E-6 | 1.17E-5 |
| SK-OV-3 | 1.90E-6 | 3.33E-6 | 5.85E-6 |
| | | | |
| Renal Cancer | | | |
| 786-0 | 1.78E-6 | 3.20E-6 | 5.76E-6 |
| A498 | 1.80E-6 | 3.77E-6 | 7.91E-6 |
| ACHN | 1.75E-6 | 3.15E-6 | 5.64E-6 |
| CAKI-1 | 3.95E-6 | 1.64E-5 | 5.41E-5 |
| RXF 393 | 1.36E-6 | 2.79E-6 | 5.71E-6 |
| SN12C | 1.63E-6 | 3.27E-6 | 6.56E-6 |
| TK-10 | 3.08E-6 | 1.02E-5 | 4.26E-5 |
| UO-31 | 1.63E-6 | 3.42E-6 | 7.17E-6 |
| | | | |
| Prostate Cancer | | | |
| PC-3 | 1.87E-6 | 4.30E-6 | 9.88E-6 |
| DU-145 | 1.94E-6 | 3.43E-6 | 6.07E-6 |
| Breast Cancer | | | |
| MCF7 | 1.54E-6 | 2.98E-6 | 5.76E-6 |
| MDA-MB-231/ATCC | 1.94E-6 | 3.49E-6 | 6.29E-6 |
| HS 578T | 2.30E-6 | 5.77E-6 | > 1.00E-4 |
| BT-549 | 1.97E-6 | 3.75E-6 | 7.13E-6 |
| T-47D | 1.94E-6 | 3.87E-6 | 7.72E-6 |
| MDA-MB-468 | 1.46E-6 | 2.88E-6 | 5.68E-6 |

Compound 24                                     Fig. 84

| Panel/Cell Line | GI50 | TGI | LC50 |
|---|---|---|---|
| Leukemia | | | |
| CCRF-CEM | 1.75E-6 | 8.50E-6 | > 3.33E-5 |
| HL-60(TB) | 3.34E-6 | 9.08E-6 | 2.47E-5 |
| MOLT-4 | 2.42E-6 | 9.84E-6 | > 3.33E-5 |
| RPMI-8226 | 4.03E-6 | 1.24E-5 | > 3.33E-5 |
| SR | 1.37E-6 | 1.70E-5 | > 3.33E-5 |
| Non-Small Cell Lung Cancer | | | |
| A549/ATCC | 6.09E-6 | 1.16E-5 | 2.23E-5 |
| EKVX | 6.13E-6 | 1.20E-5 | 2.35E-5 |
| HOP-62 | 5.66E-6 | 1.10E-5 | 2.15E-5 |
| HOP-92 | 4.00E-6 | 9.79E-6 | 2.40E-5 |
| NCI-H226 | 5.40E-6 | 1.09E-5 | 2.19E-5 |
| NCI-H23 | 6.82E-6 | 1.27E-5 | 2.37E-5 |
| NCI-H322M | 6.20E-6 | 1.15E-5 | 2.15E-5 |
| NCI-H460 | 1.12E-6 | 4.36E-6 | 2.20E-5 |
| NCI-H522 | 5.32E-6 | 1.16E-5 | 2.52E-5 |
| Colon Cancer | | | |
| COLO 205 | 9.58E-7 | 2.41E-6 | 8.99E-6 |
| HCC-2998 | 1.71E-6 | 6.53E-6 | 1.79E-5 |
| HCT-116 | 3.88E-6 | 8.56E-6 | 1.89E-5 |
| HCT-15 | 5.87E-6 | 1.22E-5 | 2.52E-5 |
| HT29 | 3.53E-6 | 8.43E-6 | 2.01E-5 |
| KM12 | 1.60E-6 | 5.65E-6 | 1.59E-5 |
| SW-620 | 1.59E-6 | 6.56E-6 | 2.07E-5 |
| CNS Cancer | | | |
| SF-268 | 6.17E-6 | 1.25E-5 | 2.52E-5 |
| SF-295 | 6.22E-6 | 1.27E-5 | 2.58E-5 |
| SF-539 | 6.41E-6 | 1.23E-5 | 2.35E-5 |
| SNB-19 | 5.89E-6 | 1.26E-5 | 2.70E-5 |
| SNB-75 | 4.74E-6 | 1.18E-5 | 2.95E-5 |
| U251 | 4.32E-6 | 9.64E-6 | 2.15E-5 |

Compound 27

Fig. 85

| Panel/Cell Line | GI50 | TGI | LC50 |
|---|---|---|---|
| Melanoma | | | |
| LOX IMVI | 2.09E-6 | 7.35E-6 | 1.97E-5 |
| MALME-3M | 7.06E-6 | 1.44E-5 | 2.95E-5 |
| M14 | 6.66E-6 | 1.21E-5 | 2.21E-5 |
| MDA-MB-435 | 4.54E-6 | 9.66E-6 | 2.06E-5 |
| SK-MEL-2 | 7.02E-6 | 1.44E-5 | 2.94E-5 |
| SK-MEL-28 | 5.59E-6 | 1.06E-5 | 2.02E-5 |
| SK-MEL-5 | 5.42E-6 | 1.04E-5 | 2.01E-5 |
| UACC-257 | 7.33E-6 | 1.39E-5 | 2.65E-5 |
| UACC-62 | 6.01E-6 | 1.15E-5 | 2.21E-5 |
| Ovarian Cancer | | | |
| IGROV1 | 4.34E-6 | 9.60E-6 | 2.12E-5 |
| OVCAR-3 | 3.56E-6 | 7.88E-6 | 1.75E-5 |
| OVCAR-4 | 5.36E-6 | 1.09E-5 | 2.21E-5 |
| OVCAR-5 | 6.11E-6 | 1.16E-5 | 2.19E-5 |
| OVCAR-8 | 5.84E-6 | 1.37E-5 | 3.23E-5 |
| NCI/ADR-RES | 5.93E-6 | 1.28E-5 | 2.75E-5 |
| SK-OV-3 | 6.20E-6 | 1.11E-5 | 1.98E-5 |
| Renal Cancer | | | |
| 786-0 | 6.61E-6 | 1.25E-5 | 2.35E-5 |
| A498 | 6.21E-6 | 1.12E-5 | 2.03E-5 |
| ACHN | 5.94E-6 | 1.13E-5 | 2.15E-5 |
| CAKI-1 | 5.31E-6 | 1.11E-5 | 2.33E-5 |
| RXF 393 | 3.34E-6 | 7.73E-6 | 1.79E-5 |
| SN12C | 4.90E-6 | 1.03E-5 | 2.18E-5 |
| TK-10 | 5.56E-6 | 1.15E-5 | 2.36E-5 |
| UO-31 | 4.42E-6 | 9.38E-6 | 1.99E-5 |
| Prostate Cancer | | | |
| PC-3 | 5.07E-6 | 1.06E-5 | 2.21E-5 |
| DU-145 | 5.75E-6 | 1.06E-5 | 1.94E-5 |
| Breast Cancer | | | |
| MCF7 | 1.28E-6 | 5.50E-6 | 1.63E-5 |
| MDA-MB-231/ATCC | 4.65E-6 | 1.02E-5 | 2.23E-5 |
| HS 578T | 6.29E-6 | 1.54E-5 | > 3.33E-5 |
| BT-549 | 7.06E-6 | 1.35E-5 | 2.57E-5 |
| T-47D | 6.06E-6 | 1.22E-5 | 2.47E-5 |
| MDA-MB-468 | 1.55E-6 | 7.03E-6 | 1.84E-5 |

Compound 27     Fig. 86

| Panel/Cell Line | GI50 | TGI | LC50 |
|---|---|---|---|
| Leukemia | | | |
| CCRF-CEM | 3.45E-6 | > 1.00E-5 | > 1.00E-5 |
| HL-60(TB) | 3.86E-6 | > 1.00E-5 | > 1.00E-5 |
| K-562 | 2.46E-6 | 7.40E-6 | > 1.00E-5 |
| MOLT-4 | 3.46E-6 | > 1.00E-5 | > 1.00E-5 |
| RPMI-8226 | 5.15E-6 | > 1.00E-5 | > 1.00E-5 |
| SR | 2.47E-6 | 8.45E-6 | > 1.00E-5 |
| Non-Small Cell Lung Cancer | | | |
| A549/ATCC | 3.30E-6 | > 1.00E-5 | > 1.00E-5 |
| EKVX | > 1.00E-5 | > 1.00E-5 | > 1.00E-5 |
| HOP-62 | 5.95E-6 | > 1.00E-5 | > 1.00E-5 |
| HOP-92 | 2.90E-6 | > 1.00E-5 | > 1.00E-5 |
| NCI-H226 | > 1.00E-5 | > 1.00E-5 | > 1.00E-5 |
| NCI-H23 | > 1.00E-5 | > 1.00E-5 | > 1.00E-5 |
| NCI-H322M | > 1.00E-5 | > 1.00E-5 | > 1.00E-5 |
| NCI-H460 | 1.94E-6 | 3.79E-6 | 7.41E-6 |
| NCI-H522 | > 1.00E-5 | > 1.00E-5 | > 1.00E-5 |
| Colon Cancer | | | |
| COLO 205 | 2.09E-6 | 4.43E-6 | 9.39E-6 |
| HCC-2998 | 1.84E-6 | 3.74E-6 | 7.62E-6 |
| HCT-116 | 2.00E-6 | 4.16E-6 | 8.63E-6 |
| HCT-15 | 4.80E-6 | > 1.00E-5 | > 1.00E-5 |
| HT29 | 2.87E-6 | 6.52E-6 | > 1.00E-5 |
| KM12 | 1.94E-6 | 4.45E-6 | > 1.00E-5 |
| CNS Cancer | | | |
| SF-268 | > 1.00E-5 | > 1.00E-5 | > 1.00E-5 |
| SF-295 | 2.08E-6 | 6.19E-6 | > 1.00E-5 |
| SF-539 | > 1.00E-5 | > 1.00E-5 | > 1.00E-5 |
| SNB-19 | 3.03E-6 | > 1.00E-5 | > 1.00E-5 |
| SNB-75 | 9.35E-6 | > 1.00E-5 | > 1.00E-5 |
| U251 | 1.55E-6 | 2.95E-6 | 5.60E-6 |

Compound 35    Fig. 87

| Panel/Cell Line | GI50 | TGI | LC50 |
|---|---|---|---|
| Melanoma | | | |
| LOX IMVI | 2.22E-6 | 4.93E-6 | > 1.00E-5 |
| MALME-3M | > 1.00E-5 | > 1.00E-5 | > 1.00E-5 |
| M14 | 5.99E-6 | > 1.00E-5 | > 1.00E-5 |
| MDA MB-435 | 4.68E-6 | > 1.00E-5 | > 1.00E-5 |
| SK-MEL-2 | > 1.00E-5 | > 1.00E-5 | > 1.00E-5 |
| SK-MEL-28 | > 1.00E-5 | > 1.00E-5 | > 1.00E-5 |
| SK-MEL-5 | > 1.00E-5 | > 1.00E-5 | > 1.00E-5 |
| UACC-257 | 1.73E-6 | 3.46E-6 | 6.91E-6 |
| UACC-62 | > 1.00E-5 | > 1.00E-5 | > 1.00E-5 |
| Ovarian Cancer | | | |
| IGROV1 | 6.53E-6 | > 1.00E-5 | > 1.00E-5 |
| OVCAR-3 | 3.85E-6 | > 1.00E-5 | > 1.00E-5 |
| OVCAR-4 | 3.11E-6 | > 1.00E-5 | > 1.00E-5 |
| OVCAR-5 | > 1.00E-5 | > 1.00E-5 | > 1.00E-5 |
| OVCAR-8 | > 1.00E-5 | > 1.00E-5 | > 1.00E-5 |
| NCI/ADR-RES | > 1.00E-5 | > 1.00E-5 | > 1.00E-5 |
| SK-OV-3 | 5.41E-6 | > 1.00E-5 | > 1.00E-5 |
| Renal Cancer | | | |
| 786-0 | > 1.00E-5 | > 1.00E-5 | > 1.00E-5 |
| A498 | > 1.00E-5 | > 1.00E-5 | > 1.00E-5 |
| ACHN | > 1.00E-5 | > 1.00E-5 | > 1.00E-5 |
| CAKI-1 | > 1.00E-5 | > 1.00E-5 | > 1.00E-5 |
| RXF 393 | 5.63E-6 | > 1.00E-5 | > 1.00E-5 |
| SN12C | 7.98E-6 | > 1.00E-5 | > 1.00E-5 |
| TK-10 | > 1.00E-5 | > 1.00E-5 | > 1.00E-5 |
| UO-31 | 8.83E-6 | > 1.00E-5 | > 1.00E-5 |
| Prostate Cancer | | | |
| PC-3 | 8.37E-6 | > 1.00E-5 | > 1.00E-5 |
| DU-145 | 6.55E-6 | > 1.00E-5 | > 1.00E-5 |
| Breast Cancer | | | |
| MCF7 | 1.78E-6 | 3.27E-6 | 6.03E-6 |
| MDA MB-231/ATCC | 2.34E-6 | 5.93E-6 | > 1.00E-5 |
| HS 578T | > 1.00E-5 | > 1.00E-5 | > 1.00E-5 |
| BT-549 | > 1.00E-5 | > 1.00E-5 | > 1.00E-5 |
| T-47D | > 1.00E-5 | > 1.00E-5 | > 1.00E-5 |
| MDA MB-468 | 2.53E-6 | > 1.00E-5 | > 1.00E-5 |

Compound 35    Fig. 88

| Panel/Cell Line | GI50 | TGI | LC50 |
|---|---|---|---|
| Leukemia | | | |
| CCRF-CEM | 1.45E-5 | 3.98E-5 | > 1.00E-4 |
| HL-60(TB) | 1.88E-5 | 4.18E-5 | 9.33E-5 |
| K-562 | 7.42E-6 | 3.11E-5 | > 1.00E-4 |
| MOLT-4 | 1.82E-5 | 4.12E-5 | > 1.00E-4 |
| RPMI-8226 | 2.04E-5 | 4.88E-5 | > 1.00E-4 |
| SR | 7.26E-6 | 3.05E-5 | > 1.00E-4 |
| Non-Small Cell Lung Cancer | | | |
| A549/ATCC | 1.55E-5 | 3.28E-5 | 6.95E-5 |
| EKVX | 1.96E-5 | 4.33E-5 | 9.58E-5 |
| HOP-62 | 1.82E-5 | 3.31E-5 | 6.74E-5 |
| HOP-92 | 1.01E-5 | 2.53E-5 | 6.38E-5 |
| NCI-H226 | 1.53E-5 | 3.22E-5 | 6.76E-5 |
| NCI-H23 | 1.75E-5 | 3.52E-5 | 7.08E-5 |
| NCI-H322M | 1.72E-5 | 3.33E-5 | 6.44E-5 |
| NCI-H460 | 6.18E-6 | 2.11E-5 | 6.22E-5 |
| NCI-H522 | 2.19E-5 | 4.18E-5 | 7.97E-5 |
| Colon Cancer | | | |
| COLO 205 | 3.05E-6 | 1.12E-5 | 3.52E-5 |
| HCC-2998 | 9.78E-6 | 2.79E-5 | 7.83E-5 |
| HCT-116 | 1.80E-5 | 4.19E-5 | > 1.00E-4 |
| HCT-15 | 1.77E-5 | 3.44E-5 | 6.68E-5 |
| HT29 | 8.33E-6 | 2.44E-5 | 6.56E-5 |
| KM12 | 1.19E-5 | 3.13E-5 | 8.22E-5 |
| CNS Cancer | | | |
| SF-268 | 1.77E-5 | 3.74E-5 | 7.93E-5 |
| SF-295 | 1.82E-5 | 3.74E-5 | 7.69E-5 |
| SF-539 | 1.91E-5 | 3.66E-5 | 7.03E-5 |
| SNB-19 | 1.80E-5 | 3.74E-5 | 8.71E-5 |
| U251 | 6.84E-6 | 2.20E-5 | 6.10E-5 |

Compound 36      Fig. 89

| Panel/Cell Line | GI50 | TGI | LC50 |
|---|---|---|---|
| Melanoma | | | |
| LOX IMVI | 1.13E-5 | 2.84E-5 | 6.18E-5 |
| MALME-3M | 2.24E-5 | 4.37E-5 | 8.52E-5 |
| M14 | 2.10E-5 | 4.38E-5 | 9.16E-5 |
| MDA-MB-435 | 1.70E-5 | 3.74E-5 | 8.25E-5 |
| SK-MEL-2 | 1.89E-5 | 3.52E-5 | 6.55E-5 |
| SK-MEL-5 | 1.45E-5 | 2.77E-5 | 5.31E-5 |
| UACC-257 | 1.14E-5 | 3.03E-5 | 8.05E-5 |
| UACC-62 | 1.75E-5 | 3.29E-5 | 6.17E-5 |
| Ovarian Cancer | | | |
| IGROV1 | 1.48E-5 | 3.54E-5 | 8.48E-5 |
| OVCAR-3 | 1.72E-5 | 3.51E-5 | 7.20E-5 |
| OVCAR-5 | 1.64E-5 | 3.19E-5 | 6.21E-5 |
| OVCAR-8 | 1.73E-5 | 3.36E-5 | 6.52E-5 |
| NCI/ADR-RES | 1.68E-5 | 3.44E-5 | 7.05E-5 |
| SK-OV-3 | 1.64E-5 | 3.27E-5 | 6.51E-5 |
| Renal Cancer | | | |
| 786-0 | 1.55E-5 | 3.82E-5 | 9.42E-5 |
| A498 | 1.48E-5 | 2.88E-5 | 5.60E-5 |
| ACHN | 1.63E-5 | 3.10E-5 | 5.91E-5 |
| CAKI-1 | 1.52E-5 | 3.35E-5 | 7.39E-5 |
| RXF 393 | 4.88E-6 | 1.95E-5 | 5.82E-5 |
| SN12C | 1.63E-5 | 3.27E-5 | 6.55E-5 |
| TK-10 | 1.54E-5 | 3.06E-5 | 6.05E-5 |
| UO-31 | 1.22E-5 | 2.70E-5 | 5.98E-5 |
| Prostate Cancer | | | |
| PC-3 | 1.62E-5 | 3.22E-5 | 6.37E-5 |
| DU-145 | 1.67E-5 | 3.17E-5 | 6.05E-5 |
| Breast Cancer | | | |
| MDA-MB-231/ATCC | 1.79E-5 | 3.45E-5 | 6.68E-5 |
| HS 578T | 1.85E-5 | 4.12E-5 | 9.19E-5 |
| BT-549 | 2.02E-5 | 3.85E-5 | 7.72E-5 |
| T-47D | 1.64E-5 | 3.44E-5 | 7.23E-5 |
| MDA-MB-468 | 1.51E-5 | 3.04E-5 | 6.13E-5 |

Compound 36                    Fig. 90

| Panel/Cell Line | GI50 | TGI | LC50 |
|---|---|---|---|
| Leukemia | | | |
| CCRF-CEM | 2.73E-6 | 7.06E-6 | > 1.88E-5 |
| HL-60(TB) | 3.58E-6 | 7.54E-6 | 1.59E-5 |
| K-562 | 2.96E-6 | 7.32E-6 | > 1.88E-5 |
| MOLT-4 | 2.92E-6 | 7.34E-6 | > 1.88E-5 |
| RPMI-8226 | 3.36E-6 | 7.98E-6 | > 1.88E-5 |
| SR | 2.70E-6 | 6.75E-6 | > 1.88E-5 |
| Non-Small Cell Lung Cancer | | | |
| A549/ATCC | 3.09E-6 | 6.12E-6 | 1.21E-5 |
| EKVX | 2.66E-6 | 5.44E-6 | 1.11E-5 |
| HOP-62 | 2.70E-6 | 5.02E-6 | 9.33E-6 |
| HOP-92 | 1.89E-6 | 4.20E-6 | 9.37E-6 |
| NCI-H226 | 2.81E-6 | 5.67E-6 | 1.15E-5 |
| NCI-H23 | 2.84E-6 | 5.93E-6 | 1.24E-5 |
| NCI-H322M | 2.71E-6 | 5.55E-6 | 1.14E-5 |
| NCI-H460 | 3.15E-6 | 6.06E-6 | 1.17E-5 |
| NCI-H522 | 3.45E-6 | 6.55E-6 | 1.24E-5 |
| Colon Cancer | | | |
| COLO 205 | 2.83E-6 | 5.28E-6 | 9.86E-6 |
| HCC-2998 | 2.62E-6 | 5.15E-6 | 1.01E-5 |
| HCT-116 | 2.87E-6 | 5.41E-6 | 1.02E-5 |
| HCT-15 | 2.89E-6 | 5.36E-6 | 1.07E-5 |
| HT29 | 3.04E-6 | 6.22E-6 | 1.27E-5 |
| KM12 | 2.84E-6 | 5.53E-6 | 1.08E-5 |
| CNS Cancer | | | |
| SF-268 | 2.81E-6 | 5.83E-6 | 1.21E-5 |
| SF-295 | 2.97E-6 | 5.82E-6 | 1.14E-5 |
| SF-539 | 3.15E-6 | 5.76E-6 | 1.06E-5 |
| SNB-19 | 2.48E-6 | 5.12E-6 | 1.06E-5 |
| SNB-75 | 2.46E-6 | 4.90E-6 | 9.73E-6 |
| U251 | 2.73E-6 | 5.72E-6 | 1.19E-5 |

Compound 37

Fig. 91

| Panel/Cell Line | GI50 | TGI | LC50 |
| --- | --- | --- | --- |
| Melanoma | | | |
| LOX IMVI | 2.83E-6 | 5.48E-6 | 1.08E-5 |
| MALME-3M | 2.78E-6 | 5.84E-6 | 1.15E-5 |
| M14 | 3.11E-6 | 6.08E-6 | 1.19E-5 |
| MDA-MB-435 | 2.95E-6 | 6.07E-6 | 1.25E-5 |
| SK-MEL-2 | 3.27E-6 | 6.54E-6 | 1.30E-5 |
| SK-MEL-28 | 2.76E-6 | 5.12E-6 | 9.50E-6 |
| SK-MEL-5 | 2.88E-6 | 5.30E-6 | 9.75E-6 |
| UACC-257 | 3.45E-6 | 7.12E-6 | 1.47E-5 |
| UACC-62 | 2.67E-6 | 5.05E-6 | 9.56E-6 |
| Ovarian Cancer | | | |
| IGROV1 | 2.69E-6 | 5.66E-6 | 1.19E-5 |
| OVCAR-3 | 2.82E-6 | 5.27E-6 | 9.83E-6 |
| OVCAR-4 | 2.49E-6 | 4.80E-6 | 9.25E-6 |
| OVCAR-5 | 2.76E-6 | 5.23E-6 | 9.92E-6 |
| OVCAR-8 | 3.06E-6 | 6.44E-6 | 1.35E-5 |
| NCI/ADR-RES | 2.87E-6 | 5.58E-6 | 1.09E-5 |
| SK-OV-3 | 2.57E-6 | 4.84E-6 | 9.10E-6 |
| Renal Cancer | | | |
| 786-0 | 2.79E-6 | 5.97E-6 | 1.28E-5 |
| A498 | 2.59E-6 | 5.27E-6 | 1.07E-5 |
| ACHN | 2.75E-6 | 5.12E-6 | 9.55E-6 |
| CAKI-1 | 2.82E-6 | 6.11E-6 | 1.32E-5 |
| RXF 393 | 2.30E-6 | 4.55E-6 | 9.00E-6 |
| SN12C | 2.50E-6 | 5.03E-6 | 1.01E-5 |
| TK-10 | 3.01E-6 | 5.59E-6 | 1.04E-5 |
| UO-31 | 2.27E-6 | 4.70E-6 | 9.70E-6 |
| Prostate Cancer | | | |
| PC-3 | 2.52E-6 | 5.02E-6 | 1.00E-5 |
| DU-145 | 2.96E-6 | 5.41E-6 | 9.90E-6 |
| Breast Cancer | | | |
| MCF7 | 2.73E-6 | 5.48E-6 | 1.10E-5 |
| MDA-MB-231/ATCC | 2.75E-6 | 5.17E-6 | 9.72E-6 |
| HS 578T | 3.04E-6 | 6.45E-6 | 1.37E-5 |
| BT-549 | 4.18E-6 | 9.36E-6 | > 1.68E-5 |
| T-47D | 2.84E-6 | 5.80E-6 | 1.10E-5 |
| MDA-MB-468 | 2.61E-6 | 5.05E-6 | 9.78E-6 |

Compound 37

Fig. 92

| Panel/Cell Line | GI50 | TGI | LC50 |
|---|---|---|---|
| Leukemia | | | |
| CCRF-CEM | 8.66E-7 | 2.80E-6 | 2.61E-5 |
| HL-60(TB) | 1.37E-6 | 4.16E-6 | 2.81E-5 |
| K-562 | 8.10E-7 | 2.04E-6 | 2.36E-5 |
| MOLT-4 | 8.35E-7 | 2.52E-6 | 2.18E-5 |
| RPMI-8226 | 1.11E-6 | 5.01E-6 | > 3.32E-5 |
| SR | 6.70E-7 | 1.81E-6 | 2.33E-5 |
| Non-Small Cell Lung Cancer | | | |
| A549/ATCC | 6.07E-7 | 1.18E-6 | 2.31E-6 |
| EKVX | 5.31E-6 | 1.24E-5 | 2.88E-5 |
| HOP-62 | 8.77E-7 | 1.97E-6 | 6.21E-6 |
| HOP-92 | 1.05E-6 | 4.49E-6 | 1.46E-5 |
| NCI-H226 | 5.27E-6 | 1.10E-5 | 2.30E-5 |
| NCI-H23 | 4.57E-6 | 1.07E-5 | 2.51E-5 |
| NCI-H322M | 3.75E-6 | 8.25E-6 | 1.82E-5 |
| NCI-H460 | 6.92E-7 | 1.40E-6 | 2.82E-6 |
| NCI-H522 | 4.37E-6 | 9.81E-6 | 2.20E-5 |
| Colon Cancer | | | |
| COLO 205 | 7.17E-7 | 1.31E-6 | 2.40E-6 |
| HCC-2998 | 6.83E-7 | 1.20E-6 | 2.18E-6 |
| HCT-116 | 6.59E-7 | 1.24E-6 | 2.35E-6 |
| HCT-15 | 1.10E-6 | 3.79E-6 | 1.54E-5 |
| HT29 | 7.20E-7 | 1.44E-6 | 2.89E-6 |
| KM12 | 6.09E-7 | 1.19E-6 | 2.33E-6 |
| CNS Cancer | | | |
| SF-268 | 1.18E-6 | 5.03E-6 | 1.71E-5 |
| SF-295 | 6.02E-7 | 1.35E-6 | 3.02E-6 |
| SF-539 | 2.37E-6 | 6.73E-6 | 1.82E-5 |
| SNB-19 | 6.32E-7 | 1.44E-6 | 3.30E-6 |
| SNB-75 | 3.14E-6 | 7.23E-6 | 1.59E-5 |
| U251 | 5.36E-7 | 9.98E-7 | 1.86E-6 |

Compound 38  Fig. 93

| Panel/Cell Line | GI50 | TGI | LC50 |
| --- | --- | --- | --- |
| Melanoma | | | |
| LOX IMVI | 6.36E-7 | 1.15E-6 | 2.07E-6 |
| MALME-3M | 6.25E-6 | 1.21E-5 | 2.36E-5 |
| M14 | 9.79E-7 | 2.63E-6 | 1.23E-5 |
| MDA MB-435 | 9.67E-7 | 3.36E-6 | 1.60E-5 |
| SK-MEL-2 | 5.66E-6 | 1.19E-5 | 2.50E-5 |
| SK-MEL-28 | 2.01E-6 | 6.10E-6 | 1.44E-5 |
| SK-MEL-5 | 2.50E-6 | 6.61E-6 | 1.48E-5 |
| UACC-257 | 6.20E-7 | 1.21E-6 | 2.35E-6 |
| UACC-62 | 4.85E-6 | 9.34E-6 | 1.80E-5 |
| Ovarian Cancer | | | |
| IGROV1 | 1.28E-6 | 4.80E-6 | 1.79E-5 |
| OVCAR-3 | 7.02E-7 | 1.52E-6 | 3.29E-6 |
| OVCAR-4 | 5.18E-7 | 9.70E-7 | 1.82E-6 |
| OVCAR-5 | 2.55E-6 | 7.08E-6 | 1.71E-5 |
| OVCAR-8 | 4.46E-6 | 1.04E-5 | 2.45E-5 |
| NCI/ADR-RES | 1.13E-6 | 4.02E-6 | 1.35E-5 |
| SK-OV-3 | 2.82E-6 | 6.75E-6 | 1.52E-5 |
| Renal Cancer | | | |
| 786-0 | 1.74E-6 | 6.90E-6 | 2.11E-5 |
| A498 | 4.88E-6 | 1.00E-5 | 2.06E-5 |
| ACHN | 2.29E-6 | 6.40E-6 | 1.55E-5 |
| CAKI-1 | 3.79E-6 | 8.99E-6 | 2.13E-5 |
| RXF 393 | 5.46E-7 | 1.03E-6 | 1.94E-6 |
| SN12C | 2.06E-6 | 6.56E-6 | 1.65E-5 |
| TK-10 | 2.54E-6 | 7.02E-6 | 1.86E-5 |
| UO-31 | 1.52E-6 | 6.10E-6 | 1.61E-5 |
| Prostate Cancer | | | |
| PC-3 | 1.24E-6 | 5.13E-6 | 1.49E-5 |
| DU-145 | 1.00E-6 | 3.26E-6 | 1.07E-5 |
| Breast Cancer | | | |
| MCF7 | 5.79E-7 | 1.07E-6 | 1.99E-6 |
| MDA-MB-231/ATCC | 7.82E-7 | 1.82E-6 | 5.84E-6 |
| HS 578T | 8.14E-7 | 1.70E-6 | 6.50E-6 |
| BT-549 | 6.15E-6 | 1.22E-5 | 2.40E-5 |
| T-47D | 1.76E-6 | 5.95E-6 | 1.66E-5 |
| MDA-MB-468 | 6.29E-7 | 1.44E-6 | 3.30E-6 |

Compound 38

Fig. 94

| Panel/Cell Line | GI50 | TGI | LC50 |
|---|---|---|---|
| Leukemia | | | |
| CCRF-CEM | 3.34E-6 | 9.55E-6 | > 1.68E-5 |
| HL-60(TB) | 3.44E-6 | 6.72E-6 | 1.31E-5 |
| K-562 | 3.50E-6 | 7.82E-6 | > 1.68E-5 |
| MOLT-4 | 3.26E-6 | 7.70E-6 | > 1.68E-5 |
| RPMI-8226 | 3.13E-6 | 7.64E-6 | > 1.68E-5 |
| SR | 2.85E-6 | 6.80E-6 | > 1.68E-5 |
| Non-Small Cell Lung Cancer | | | |
| A549/ATCC | 2.50E-6 | 4.95E-6 | 9.78E-6 |
| EKVX | 3.04E-6 | 6.22E-6 | 1.27E-5 |
| HOP-62 | 2.81E-6 | 5.14E-6 | 9.42E-6 |
| HOP-92 | 2.17E-6 | 4.49E-6 | 9.27E-6 |
| NCI-H226 | 2.79E-6 | 5.84E-6 | 1.22E-5 |
| NCI-H23 | 3.16E-6 | 6.89E-6 | 1.50E-5 |
| NCI-H322M | 2.70E-6 | 5.73E-6 | 1.21E-5 |
| NCI-H460 | 3.25E-6 | 6.37E-6 | 1.25E-5 |
| NCI-H522 | 2.91E-6 | 5.83E-6 | 1.17E-5 |
| Colon Cancer | | | |
| COLO 205 | 2.78E-6 | 5.19E-6 | 9.70E-6 |
| HCC-2998 | 2.73E-6 | 5.28E-6 | 1.02E-5 |
| HCT-116 | 2.95E-6 | 5.69E-6 | 1.10E-5 |
| HCT-15 | 3.32E-6 | 7.12E-6 | 1.53E-5 |
| HT29 | 3.26E-6 | 6.81E-6 | 1.42E-5 |
| KM12 | 2.93E-6 | 6.28E-6 | 1.35E-5 |
| CNS Cancer | | | |
| SF-268 | 2.78E-6 | 5.44E-6 | 1.06E-5 |
| SF-295 | 3.16E-6 | 6.45E-6 | 1.32E-5 |
| SF-539 | 3.29E-6 | 6.89E-6 | 1.36E-5 |
| SNB-19 | 2.47E-6 | 4.81E-6 | 9.36E-6 |
| SNB-75 | 2.38E-6 | 4.61E-6 | 8.91E-6 |
| U251 | 2.61E-6 | 4.98E-6 | 9.50E-6 |

Compound 39

Fig. 95

| Panel/Cell Line | GI50 | TGI | LC50 |
|---|---|---|---|
| Melanoma | | | |
| LOX IMVI | 3.29E-6 | 5.96E-6 | 1.08E-5 |
| MALME-3M | 3.14E-6 | 6.26E-6 | 1.25E-5 |
| M14 | 3.02E-6 | 5.83E-6 | 1.13E-5 |
| MDA MB-435 | 3.20E-6 | 6.76E-6 | 1.43E-5 |
| SK-MEL-2 | 3.01E-6 | 5.77E-6 | 1.11E-5 |
| SK-MEL-28 | 2.62E-6 | 4.89E-6 | 9.12E-6 |
| SK-MEL-5 | 2.90E-6 | 5.23E-6 | 9.43E-6 |
| UACC-257 | 2.96E-6 | 5.74E-6 | 1.11E-5 |
| UACC-62 | 2.51E-6 | 4.83E-6 | 9.32E-6 |
| Ovarian Cancer | | | |
| IGROV1 | 2.88E-6 | 5.97E-6 | 1.23E-5 |
| OVCAR-3 | 2.79E-6 | 5.21E-6 | 9.72E-6 |
| OVCAR-4 | 2.81E-6 | 5.11E-6 | 9.31E-6 |
| OVCAR-5 | 2.83E-6 | 5.33E-6 | 1.00E-5 |
| OVCAR-8 | 2.87E-6 | 5.58E-6 | 1.17E-5 |
| NCI/ADR-RES | 5.50E-6 | > 1.68E-5 | > 1.68E-5 |
| SK-OV-3 | 2.83E-6 | 4.91E-6 | 9.17E-6 |
| Renal Cancer | | | |
| 786-0 | 2.72E-6 | 5.39E-6 | 1.07E-5 |
| A498 | 2.32E-6 | 4.70E-6 | 9.50E-6 |
| ACHN | 2.62E-6 | 4.93E-6 | 9.28E-6 |
| CAKI-1 | 4.38E-6 | 1.36E-5 | > 1.68E-5 |
| RXF 393 | 2.45E-6 | 4.70E-6 | 9.05E-6 |
| SN12C | 2.55E-6 | 4.98E-6 | 9.70E-6 |
| TK-10 | 3.41E-6 | 6.72E-6 | 1.32E-5 |
| UO-31 | 2.37E-6 | 4.70E-6 | 9.31E-6 |
| Prostate Cancer | | | |
| PC-3 | 2.37E-6 | 4.69E-6 | 9.26E-6 |
| DU-145 | 2.98E-6 | 5.42E-6 | 9.85E-6 |
| Breast Cancer | | | |
| MCF7 | 2.59E-6 | 5.10E-6 | 1.00E-5 |
| MDA-MB-231/ATCC | 2.89E-6 | 5.27E-6 | 9.82E-6 |
| HS 578T | 2.61E-6 | 6.01E-6 | 1.38E-5 |
| BT-549 | 3.39E-6 | 6.53E-6 | 1.26E-5 |
| T-47D | 3.03E-6 | 5.77E-6 | 1.10E-5 |
| MDA-MB-468 | 2.57E-6 | 4.89E-6 | 9.30E-6 |

Compound 39

Fig. 96

| Panel/Cell Line | GI50 | TGI | LC50 |
|---|---|---|---|
| Leukemia | | | |
| CCRF-CEM | 8.85E-7 | 2.30E-6 | 3.22E-5 |
| HL-60(TB) | 1.03E-6 | 3.93E-6 | 2.18E-5 |
| K-562 | 7.72E-7 | 2.05E-6 | 1.56E-5 |
| MOLT-4 | 9.96E-7 | 3.52E-6 | 3.24E-5 |
| RPMI-8226 | 1.22E-6 | 5.90E-6 | > 3.32E-5 |
| SR | 7.85E-7 | 2.32E-6 | > 3.32E-5 |
| Non-Small Cell Lung Cancer | | | |
| A549/ATCC | 6.16E-7 | 1.30E-6 | 2.76E-6 |
| EKVX | 2.98E-6 | 9.04E-6 | 2.55E-5 |
| HOP-62 | 2.70E-6 | 9.42E-6 | 3.05E-5 |
| HOP-92 | 1.84E-6 | 7.87E-6 | 2.21E-5 |
| NCI-H226 | 5.17E-6 | 1.02E-5 | 2.01E-5 |
| NCI-H23 | 4.40E-6 | 1.02E-5 | 2.37E-5 |
| NCI-H322M | 5.13E-6 | 1.02E-5 | 2.02E-5 |
| NCI-H460 | 7.10E-7 | 1.34E-6 | 2.54E-6 |
| NCI-H522 | 3.75E-6 | 8.91E-6 | 2.11E-5 |
| Colon Cancer | | | |
| COLO 205 | 8.86E-7 | 2.05E-6 | 8.10E-6 |
| HCC-2998 | 5.83E-7 | 1.14E-6 | 2.22E-6 |
| HCT-116 | 5.97E-7 | 1.08E-6 | 1.95E-6 |
| HCT-15 | 3.00E-6 | 8.10E-6 | 2.07E-5 |
| HT29 | 7.03E-7 | 1.43E-6 | 2.90E-6 |
| KM12 | 7.84E-7 | 1.94E-6 | 2.40E-5 |
| CNS Cancer | | | |
| SF-268 | 4.14E-6 | 1.07E-5 | 2.75E-5 |
| SF-295 | 1.02E-6 | 3.60E-6 | 1.85E-5 |
| SF-539 | 1.28E-6 | 3.50E-6 | 1.59E-5 |
| SNB-19 | 1.36E-6 | 6.57E-6 | 3.00E-5 |
| SNB-75 | 4.11E-6 | 8.59E-6 | 1.80E-5 |
| U251 | 5.44E-7 | 1.06E-6 | 2.06E-6 |

Compound 40  Fig. 97

| Panel/Cell Line | GI50 | TGI | LC50 |
|---|---|---|---|
| Melanoma | | | |
| LOX IMVI | 6.22E-7 | 1.12E-6 | 2.00E-6 |
| MALME-3M | 7.15E-6 | 1.36E-5 | 2.80E-5 |
| M14 | 1.14E-6 | 3.95E-6 | 1.78E-5 |
| MDA-MB-435 | 1.16E-6 | 5.14E-6 | 2.42E-5 |
| SK-MEL-2 | 5.59E-6 | 1.12E-5 | 2.24E-5 |
| SK-MEL-28 | 3.43E-6 | 7.75E-6 | 1.75E-5 |
| SK-MEL-5 | 2.76E-6 | 7.00E-6 | 1.57E-5 |
| UACC-257 | 6.56E-7 | 1.29E-6 | 2.55E-6 |
| UACC-62 | 4.79E-6 | 1.00E-5 | 2.10E-5 |
| Ovarian Cancer | | | |
| IGROV1 | 1.34E-6 | 5.02E-6 | 2.23E-5 |
| OVCAR-3 | 8.11E-7 | 1.87E-6 | 9.45E-6 |
| OVCAR-4 | 5.85E-7 | 1.07E-6 | 1.96E-6 |
| OVCAR-5 | 2.73E-6 | 7.40E-6 | 1.79E-5 |
| OVCAR-8 | 4.46E-6 | 1.00E-5 | 2.25E-5 |
| NCI/ADR-RES | 3.37E-6 | 8.59E-6 | 2.19E-5 |
| SK-OV-3 | 2.24E-6 | 7.20E-6 | 1.96E-5 |
| Renal Cancer | | | |
| 786-0 | 2.71E-6 | 9.13E-6 | 2.76E-5 |
| A498 | 4.71E-6 | 9.35E-6 | 1.85E-5 |
| ACHN | 2.16E-6 | 6.63E-6 | 1.89E-5 |
| CAKI-1 | 4.07E-6 | 9.10E-6 | 2.03E-5 |
| RXF 393 | 5.51E-7 | 1.11E-6 | 2.23E-6 |
| SN12C | 1.54E-6 | 6.28E-6 | 1.82E-5 |
| TK-10 | 4.84E-6 | 9.79E-6 | 2.08E-5 |
| UO-31 | 3.46E-6 | 7.87E-6 | 1.79E-5 |
| Prostate Cancer | | | |
| PC-3 | 1.51E-6 | 6.15E-6 | 1.85E-5 |
| DU-145 | 1.08E-6 | 3.44E-6 | 1.44E-5 |
| Breast Cancer | | | |
| MCF7 | 5.15E-7 | 9.90E-7 | 1.90E-6 |
| MDA-MB-231/ATCC | 1.10E-6 | 3.40E-6 | 1.48E-5 |
| HS 578T | 9.38E-7 | 2.41E-6 | 3.02E-5 |
| BT-549 | 5.69E-6 | 1.09E-5 | 2.08E-5 |
| T-47D | 3.94E-6 | 1.04E-5 | 2.73E-5 |
| MDA-MB-468 | | | |

Compound 40

Fig. 98

| Panel/Cell Line | GI50 | TGI | LC50 |
|---|---|---|---|
| Leukemia | | | |
| CCRF-CEM | 3.83E-6 | > 1.00E-5 | > 1.00E-5 |
| HL-60(TB) | 3.57E-6 | > 1.00E-5 | > 1.00E-5 |
| K-562 | 4.48E-6 | > 1.00E-5 | > 1.00E-5 |
| MOLT-4 | 4.21E-6 | > 1.00E-5 | > 1.00E-5 |
| RPMI-8226 | 5.74E-6 | > 1.00E-5 | > 1.00E-5 |
| SR | 2.48E-6 | 5.81E-6 | > 1.00E-5 |
| Non-Small Cell Lung Cancer | | | |
| A549/ATCC | > 1.00E-5 | > 1.00E-5 | > 1.00E-5 |
| HOP-62 | > 1.00E-5 | > 1.00E-5 | > 1.00E-5 |
| HOP-92 | 8.02E-6 | > 1.00E-5 | > 1.00E-5 |
| NCI-H226 | > 1.00E-5 | > 1.00E-5 | > 1.00E-5 |
| NCI-H23 | > 1.00E-5 | > 1.00E-5 | > 1.00E-5 |
| NCI-H322M | > 1.00E-5 | > 1.00E-5 | > 1.00E-5 |
| NCI-H460 | 5.21E-6 | > 1.00E-5 | > 1.00E-5 |
| NCI-H522 | > 1.00E-5 | > 1.00E-5 | > 1.00E-5 |
| Colon Cancer | | | |
| COLO 205 | > 1.00E-5 | > 1.00E-5 | > 1.00E-5 |
| HCC-2998 | > 1.00E-5 | > 1.00E-5 | > 1.00E-5 |
| HCT-116 | 5.19E-6 | > 1.00E-5 | > 1.00E-5 |
| HCT-15 | > 1.00E-5 | > 1.00E-5 | > 1.00E-5 |
| HT29 | > 1.00E-5 | > 1.00E-5 | > 1.00E-5 |
| KM12 | > 1.00E-5 | > 1.00E-5 | > 1.00E-5 |
| SW-620 | > 1.00E-5 | > 1.00E-5 | > 1.00E-5 |
| CNS Cancer | | | |
| SF-268 | > 1.00E-5 | > 1.00E-5 | > 1.00E-5 |
| SF-295 | > 1.00E-5 | > 1.00E-5 | > 1.00E-5 |
| SF-539 | > 1.00E-5 | > 1.00E-5 | > 1.00E-5 |
| SNB-19 | > 1.00E-5 | > 1.00E-5 | > 1.00E-5 |
| U251 | > 1.00E-5 | > 1.00E-5 | > 1.00E-5 |

Compound 44

Fig. 99

| Panel/Cell Line | GI50 | TGI | LC50 |
|---|---|---|---|
| Melanoma | | | |
| LOX IMVI | > 1.00E-5 | > 1.00E-5 | > 1.00E-5 |
| MALME-3M | > 1.00E-5 | > 1.00E-5 | > 1.00E-5 |
| M14 | > 1.00E-5 | > 1.00E-5 | > 1.00E-5 |
| MDA-MB-435 | > 1.00E-5 | > 1.00E-5 | > 1.00E-5 |
| SK-MEL-2 | > 1.00E-5 | > 1.00E-5 | > 1.00E-5 |
| SK-MEL-28 | > 1.00E-5 | > 1.00E-5 | > 1.00E-5 |
| SK-MEL-5 | > 1.00E-5 | > 1.00E-5 | > 1.00E-5 |
| UACC-257 | > 1.00E-5 | > 1.00E-5 | > 1.00E-5 |
| UACC-62 | 3.80E-6 | > 1.00E-5 | > 1.00E-5 |
| Ovarian Cancer | | | |
| IGROV1 | > 1.00E-5 | > 1.00E-5 | > 1.00E-5 |
| OVCAR-3 | > 1.00E-5 | > 1.00E-5 | > 1.00E-5 |
| OVCAR-4 | > 1.00E-5 | > 1.00E-5 | > 1.00E-5 |
| OVCAR-5 | > 1.00E-5 | > 1.00E-5 | > 1.00E-5 |
| OVCAR-8 | > 1.00E-5 | > 1.00E-5 | > 1.00E-5 |
| NCI/ADR-RES | > 1.00E-5 | > 1.00E-5 | > 1.00E-5 |
| SK-OV-3 | > 1.00E-5 | > 1.00E-5 | > 1.00E-5 |
| Renal Cancer | | | |
| 786-0 | > 1.00E-5 | > 1.00E-5 | > 1.00E-5 |
| A498 | > 1.00E-5 | > 1.00E-5 | > 1.00E-5 |
| ACHN | > 1.00E-5 | > 1.00E-5 | > 1.00E-5 |
| CAKI-1 | > 1.00E-5 | > 1.00E-5 | > 1.00E-5 |
| RXF 393 | 4.88E-6 | > 1.00E-5 | > 1.00E-5 |
| SN12C | > 1.00E-5 | > 1.00E-5 | > 1.00E-5 |
| TK-10 | > 1.00E-5 | > 1.00E-5 | > 1.00E-5 |
| UO-31 | > 1.00E-5 | > 1.00E-5 | > 1.00E-5 |
| Prostate Cancer | | | |
| PC-3 | > 1.00E-5 | > 1.00E-5 | > 1.00E-5 |
| DU-145 | > 1.00E-5 | > 1.00E-5 | > 1.00E-5 |
| Breast Cancer | | | |
| MCF7 | > 1.00E-5 | > 1.00E-5 | > 1.00E-5 |
| MDA-MB-231/ATCC | > 1.00E-5 | > 1.00E-5 | > 1.00E-5 |
| HS 578T | > 1.00E-5 | > 1.00E-5 | > 1.00E-5 |
| BT-549 | > 1.00E-5 | > 1.00E-5 | > 1.00E-5 |
| T-47D | > 1.00E-5 | > 1.00E-5 | > 1.00E-5 |
| MDA-MB-468 | > 1.00E-5 | > 1.00E-5 | > 1.00E-5 |

Compound 44      Fig. 100

TOCOTRIENOL DERIVATIVES AND ASSOCIATED METHODS

This application is a divisional application of application Ser. No. 13/690,910 filed Nov. 30, 2012 which claims the benefit of U.S. Provisional Application No. 61/566,286, filed Dec. 2, 2011.

This invention was made with government support from the United States Public Health Service. The government may have certain rights to this invention.

Both γ-tocotrienol, referred to herein as Compound 1, and δ-tocotrienol, referred to herein as Compound 2, were isolated from a tocotrienol-rich fraction of palm oil using normal phase vacuum liquid chromatography. Compounds 3-29 and 35-44 which are 3,4-dihydro-1,3-oxazines, Compounds 30-31 which are Mannich bases, and Compounds 32-34 which are hydroxymethyl tocotrienol analogs were prepared as semi synthetic derivatives of Compounds 1 and 2.

(R)-2,5,6,8-tetramethyl-8-((3E,7E)-4,8,12-trimethyl-trideca-3,7,11-trienyl)-1,2,3,8,9,10-hexahydrochromeno[5,6-e][1,3]oxazine, referred to herein as Compound 3, has the following properties: yellow viscous oil; $[\alpha]_D^{25}$ +1.7 (c 0.016, $CH_2Cl_2$); IR ($CH_2Cl_2$) $\nu_{max}$ 3599, 2975, 2926, 1605 cm$^{-1}$; $^1$H- and $^{13}$C-NMR characteristics found in FIGS. 1A, 1B, and 10; and HREIMS m/z 466.3664, [M+H]$^+$ (calcd for $C_{31}H_{48}NO_2$, 466.3680).

(R)-2,6,8-trimethyl-8-((3E,7E)-4,8,12-trimethyltrideca-3,7,11-trienyl)-1,2,3,8,9,10-hexahydrochromeno[5,6-e][1,3]oxazine, referred to herein as Compound 4, has the following properties: yellow viscous oil; $[\alpha]_D^{25}$ +4.72 (c 0.024, $CH_2Cl_2$); IR ($CH_2Cl_2$) $\nu_{max}$ 3660, 22858, 1618, 1476, 1345, 1099, 942 cm$^{-1}$; $^1$H- and $^{13}$C-NMR characteristics found in FIGS. 1A, 1B, and 10; and HREIMS m/z 452.6907, [M+H]$^+$ (calcd for $C_{30}H_{46}NO_2$, 452.6917).

(R)-2-allyl-5,6,8-trimethyl-8-((3E,7E)-4,8,12-trimethyl-trideca-3,7,11-trienyl)-1,2,3,8,9,10-hexahydrochromeno[5,6-e][1,3]oxazine, referred to herein as Compound 5, has the following properties: yellow viscous oil; $[\alpha]_D^{25}$ +0.1 (c 0.03, $CH_2Cl_2$); IR ($CH_2Cl_2$) $\nu_{max}$ 3676, 2923, 1606 cm$^{-1}$; $^1$H- and $^{13}$C-NMR characteristics found in FIGS. 1A, 1B, and 10; and HREIMS m/z 492.3843, [M+H]$^+$ (calcd for $C_{33}H_{50}NO_2$, 492.3836).

(R)-2-benzyl-5,6,8-trimethyl-8-((3E,7E)-4,8,12-trimethyltrideca-3,7,11-trienyl)-1,2,3,8,9,10-hexahydrochromeno[5,6-e][1,3]oxazine, referred to herein as Compound 6, has the following properties: yellow viscous oil; $[\alpha]_D^{25}$ +0.625 (c 0.04, $CH_2Cl_2$); IR ($CH_2Cl_2$) $\nu_{max}$ 3600, 2927, 2850, 1605 cm$^{-1}$; $^1$H- and $^{13}$C-NMR characteristics found in FIGS. 1A, 1B, and 10; and HREIMS m/z 542.3980, [M+H]$^+$ (calcd for $C_{37}H_{52}NO_2$, 542.3993).

(R)-2-(1-benzylpiperidin-4-yl)-5,6,8-trimethyl-8-((3E,7E)-4,8,12-trimethyltrideca-3,7,11-trienyl)-1,2,3,8,9,10-hexahydrochromeno[5,6-e][1,3]oxazine, referred to herein as Compound 7, has the following properties: yellow viscous oil; $[\alpha]_D^{25}$ +0.017 (c 0.047, $CH_2Cl_2$); IR ($CH_2Cl_2$) $\nu_{max}$ 3599, 2928, 1605, 1378 cm$^{-1}$; $^1$H- and $^{13}$C-NMR characteristics found in FIGS. 2A, 2B, and 10; and HREIMS m/z 625.4733, [M+H]$^+$ (calcd for $C_{42}H_{61}N_2O_2$, 625.4728).

(R)-2-(1-benzylpiperidin-4-yl)-6,8-dimethyl-8-((3E,7E)-4,8,12-trimethyltrideca-3,7,11-trienyl)-1,2,3,8,9,10-hexahydrochromeno[5,6-e][1,3]oxazine, referred to herein as Compound 8, has the following properties: yellow viscous oil; $[\alpha]_D^{25}$ +0.21 (c 0.083, $CH_2Cl_2$); IR ($CH_2C_{12}$) $\nu_{max}$ 3684, 2927, 1605, 1474 cm$^{-1}$; $^1$H- and $^{13}$C-NMR characteristics found in FIGS. 2A, 2B, and 11 in; and HREIMS m/z 611.4581, [M+H]$^+$ (calcd for $C_{41}H_{59}N_2O_2$, 611.4571).

2-((R)-5,6,8-trimethyl-8-((3E,7E)-4,8,12-trimethyl-trideca-3,7,11-trienyl)-9,10-dihydrochromeno[5,6-e][1,3]oxazin-2(1H,3H,8H)-yl)ethanol, referred to herein as Compound 9, has the following properties: yellow viscous oil; $[\alpha]_D^{25}$ +66 (c 0.0008, $CH_2Cl_2$); IR ($CH_2Cl_2$) $\nu_{max}$ 3602, 2850, 1605, 1091 cm$^{-1}$; $^1$H- and $^{13}$C-NMR characteristics found in FIGS. 2A, 2B, and 11; and HREIMS m/z 496.3769, [M+H]$^+$ (calcd for $C_{32}H_{50}NO_3$, 496.3785).

2-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)ethanol, referred to herein as Compound 10, has the following properties: yellow viscous oil; $[\alpha]_D^{25}$ +0.017 (c 0.06, $CH_2Cl_2$); IR ($CH_2Cl_2$) $\nu_{max}$ 3599, 2928, 2855, 1606, 1473 cm$^{-1}$; $^1$H- and $^{13}$C-NMR characteristics found in FIGS. 2A, 2B, and 11; and HREIMS m/z 482.3632, [M+H]$^+$ (calcd for $C_{31}H_{48}NO_3$, 482.3629).

2-((R)-5,7-dimethyl-7-((3E,7E)-4,8,12-trimethyltrideca-3,7,11-trienyl)-8,9-dihydrochromeno[7,6-e][1,3]oxazin-3(2H,4H,7H)-yl)ethanol, referred to herein as Compound 11, has the following properties: yellow viscous oil; $[\alpha]_D^{25}$ +24 (c 0.018, $CH_2Cl_2$); IR ($CH_2Cl_2$) $\nu_{max}$ 3599, 2996, 1606, 1292, 1241 cm$^{-1}$; $^1$H- and $^{13}$C-NMR characteristics found in FIGS. 3A, 3B, and 11; and HREIMS m/z 482.3620, [M+H]$^+$ (calcd for $C_{31}H_{48}NO_3$, 482.3629).

3-((R)-5,6,8-trimethyl-8-((3E,7E)-4,8,12-trimethyl-trideca-3,7,11-trienyl)-9,10-dihydrochromeno[5,6-e][1,3]oxazin-2(1H,3H,8H)-yl)propan-1-ol, referred to herein as Compound 12, has the following properties: yellow viscous oil, $[\alpha]_D^{25}$ +1.67 (c 0.03, $CH_2Cl_2$); IR ($CH_2Cl_2$) $\nu_{max}$ 3599, 1647, 1289, 1242 cm$^{-1}$; $^1$H- and $^{13}$C-NMR characteristics found in FIGS. 3A, 3B, and 11; and HREIMS m/z 510.3949, [M+H]$^+$ (calcd for $C_{33}H_{52}NO_3$, 510.3942).

3-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)propan-1-ol, referred to herein as Compound 13, has the following properties: yellow viscous oil; $[\alpha]_D^{25}$ +0.14 (c 0.05, $CH_2Cl_2$); IR ($CH_2Cl_2$) $\nu_{max}$ 3599, 2929, 1606 cm$^{-1}$; $^1$H- and $^{13}$C-NMR characteristics found in FIGS. 3 and 12; and HREIMS m/z 496.3783, [M+H]$^+$ (calcd for $C_{32}H_{50}NO_3$, 496.3785).

(R)-2-(3,3-diethoxypropyl)-5,6,8-trimethyl-8-((3E,7E)-4,8,12-trimethyltrideca-3,7,11-trienyl)-1,2,3,8,9,10-hexahydrochromeno[5,6-e][1,3]oxazine, referred to herein as Compound 14, has the following properties: yellow viscous oil; $[\alpha]_D^{25}$ +21.5 (c 0.0011, $CH_2Cl_2$); IR ($CH_2Cl_2$) $\nu_{max}$ 3599, 2922, 2853, 1606, 1374, 1067 cm$^{-1}$; $^1$H- and $^{13}$C-NMR characteristics found in FIGS. 3 and 12; and HREIMS m/z 582.4539, [M+H]$^+$ (calcd for $C_{37}H_{60}NO_4$, 582.4517).

(R)-2-(3,3-diethoxypropyl)-6,8-dimethyl-8-((3E,7E)-4,8,12-trimethyltrideca-3,7,11-trienyl)-1,2,3,8,9,10-hexahydrochromeno[5,6-e][1,3]oxazine, referred to herein as Compound 15, has the following properties: yellow viscous oil; $[\alpha]_D^{25}$ +67.3 (c 0.0012, $CH_2Cl_2$); IR ($CH_2Cl_2$) $\nu_{max}$ 3599, 2922, 2854, 1606, 1374, 1055 cm$^{-1}$; $^1$H- and $^{13}$C-NMR characteristics found in FIGS. 4 and 12; and HREIMS m/z 568.4353, [M+H]$^+$ (calcd for $C_{36}H_{58}NO_4$, 568.4360).

(R)-5,6,8-trimethyl-2-(piperidin-4-ylmethyl)-8-((3E,7E)-4,8,12-trimethyltrideca-3,7,11-trienyl)-1,2,3,8,9,10-hexahydrochromeno[5,6-e][1,3]oxazine, referred to herein as Compound 16, has the following properties: yellow viscous oil; $[\alpha]_D^{25}$ +0.55 (c 0.02, $CH_2Cl_2$); IR ($CH_2Cl_2$) $\nu_{max}$ 3666, 2922, 2854, 1606, 1521 cm$^{-1}$; $^1$H- and $^{13}$C-NMR characteristics found in FIGS. 4 and 12; and HREIMS m/z 549.4392, [M+H]$^+$ (calcd for $C_{36}H_{57}N_2O_2$, 549.4420).

5-((R)-5,6,8-trimethyl-8-((3E,7E)-4,8,12-trimethyl-trideca-3,7,11-trienyl)-9,10-dihydrochromeno[5,6-e][1,3]oxazin-2(1H,3H,8H)-yl)pentan-1-ol, referred to herein as Compound 17, has the following properties: yellow viscous oil; $[\alpha]_D^{25}$ +18.4 (c 0.0012, $CH_2Cl_2$); IR ($CH_2Cl_2$) $v_{max}$ 3682, 3600, 2929, 2855, 1606, 1378, 1236, 1096 $cm^{-1}$; $^1H$- and $^{13}C$-NMR characteristics found in FIGS. 4 and 13; and HREIMS m/z 538.4253, $[M+H]^+$ (calcd for $C_{35}H_{56}NO_3$, 538.4255).

5-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)pentan-1-ol, referred to herein as Compound 18, has the following properties: yellow viscous oil; $[\alpha]_D^{25}$ +0.21 (c 0.046, $CH_2Cl_2$); IR ($CH_2Cl_2$) $v_{max}$ 3679, 3600, 2929, 2855, 1606, 1473, $cm^{-1}$; $^1H$- and $^{13}C$-NMR characteristics found in FIGS. 4 and 13; and HREIMS m/z 524.4109, $[M+H]^+$ (calcd for $C_{34}H_{54}NO_3$, 524.4098).

5-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)pentanoic acid, referred to herein as Compound 19, has the following properties: yellow viscous oil; $[\alpha]_D^{25}$ +0.2 (c 0.04, $CH_2Cl_2$); IR ($CH_2Cl_2$) $v_{max}$ 3683, 3601, 2927, 2854, 1750, 1606, 1465, $cm^{-1}$; $^1H$- and $^{13}C$-NMR characteristics found in FIGS. 5A, 5B, and 13; and HREIMS m/z 552.4033, $[M+H]^+$ (calcd for $C_{35}H_{54}NO_4$, 552.4047).

5-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)pentanoic acid, referred to herein as Compound 20, has the following properties: yellow viscous oil; $[\alpha]_D^{25}$ +0.14 (c 0.05, $CH_2Cl_2$); IR ($CH_2Cl_2$) $v_{max}$ 3676, 3599, 2927, 2855, 1748, 1606, 1473, $cm^{-1}$; $^1H$- and $^{13}C$-NMR characteristics found in FIGS. 5A, 5B, and 13; and HREIMS m/z 538.3873, $[M+H]^+$ (calcd for $C_{34}H_{52}NO_4$, 538.3891).

6-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)hexanoic acid, referred to herein as Compound 21, has the following properties: yellow viscous oil; $[\alpha]_D^{25}$ +0.47 (c 0.063, $CH_2Cl_2$); IR ($CH_2Cl_2$) $v_{max}$ 3684, 3600, 2930, 2856, 1748, 1606, 1458, 1093 $cm^{-1}$; $^1H$- and $^{13}C$-NMR characteristics found in FIGS. 5A, 5B, and 14; and HREIMS m/z 566.4198, $[M+H]^+$ (calcd for $C_{36}H_{56}NO_4$, 566.4204).

6-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)hexanoic acid, referred to herein as Compound 22, has the following properties: yellow viscous oil; $[\alpha]_D^{25}$ +0.18 (c 0.05, $CH_2Cl_2$); IR ($CH_2Cl_2$) $v_{max}$ 3676, 3598, 2922, 2855, 1748, 1606, 1473, 1096 $cm^{-1}$; $^1H$- and $^{13}C$-NMR characteristics found in FIGS. 5A, 5B, and 14; and HREIMS m/z 552.4043, $[M+H]^+$ (calcd for $C_{35}H_{54}NO_4$, 552.4047).

(R)-2-(3,4-dimethoxyphenethyl)-5,6,8-trimethyl-8-((3E,7E)-4,8,12-trimethyltrideca-3,7,11-trienyl)-1,2,3,8,9,10-hexahydrochromeno[5,6-e][1,3]oxazine, referred to herein as Compound 23, has the following properties: yellow viscous oil; $[\alpha]_D^{25}$ +0.027 (c 0.036, $CH_2Cl_2$); IR ($CH_2Cl_2$) $v_{max}$ 3683, 3600, 2921, 2855, 1606, 1516, 1085 $cm^{-1}$; 4I- and $^{13}C$-NMR characteristics found in FIGS. 6A, 6B, and 14; and HREIMS m/z 616.4366, $[M+H]^+$ (calcd for $C_{40}H_{58}NO_4$, 616.4360).

(R)-2-(3,4-dimethoxyphenethyl)-6,8-dimethyl-8-((3E,7E)-4,8,12-trimethyltrideca-3,7,11-trienyl)-1,2,3,8,9,10-hexahydrochromeno[5,6-e][1,3]oxazine, referred to herein as Compound 24, has the following properties: yellow viscous oil; $[\alpha]_D^{25}$ +0.26 (c 0.083, $CH_2Cl_2$); IR ($CH_2Cl_2$) $v_{max}$ 3682, 3600, 2917, 2854, 1606, 1516, 1029 $cm^{-1}$; $^1H$- and $^{13}C$-NMR characteristics found in FIGS. 6A, 6B, and 14; and HREIMS m/z 602.4192, $[M+H]^+$ (calcd for $C_{39}H_{56}NO_4$, 602.4204).

(R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine, referred to herein as Compound 25, has the following properties: yellow viscous oil, $[\alpha]_D^{25}$ +0.255 (c 0.013, $CH_2Cl_2$); IR ($CH_2Cl_2$) $v_{max}$ 3676, 2922, 2854, 1606, 1521, 1068, 953 $cm^{-1}$; $^1H$- and $^{13}C$-NMR characteristics found in FIGS. 6A, 6B, and 14; and HREIMS m/z 602.4204, $[M+H]^+$ (calcd for $C_{39}H_{56}NO_4$, 602.4204).

4-(2-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)ethyl)phenol, referred to herein as Compound 26, has the following properties: yellow viscous oil, $[\alpha]_D^{25}$ +0.6 (c 0.026, $H_2Cl_2$); IR ($CH_2Cl_2$) $v_{max}$ 3676, 3656, 2922, 2855, 1606, 1516, 1083 $cm^{-1}$; $^1H$- and $^{13}C$-MR characteristics found in FIGS. 6A, 6B, and 15; and HREIMS m/z 572.4090, $[M+H]^+$ (calcd for $C_{38}H_{54}NO_3$, 572.4098).

4-(2-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)ethyl)phenol, referred to herein as Compound 27, has the following properties: yellow viscous oil; $[\alpha]_D^{25}$ +1.98 (c 0.033, $CH_2Cl_2$); IR ($CH_2Cl_2$) $v_{max}$ 3688, 3599, 2932, 2850, 1606, 1516, 1172 $cm^{-1}$; $^1H$- and $^{13}C$-NMR characteristics found in FIGS. 7A, 7B, and 15; and HREIMS m/z 558.3925, $[M+H]^+$ (calcd for $C_{37}H_{52}NO_3$, 558.3942).

(R)-5,6,8-trimethyl-2-(3-nitrobenzyl)-8-((3E,7E)-4,8,12-trimethyltrideca-3,7,11-trienyl)-1,2,3,8,9,10-hexahydrochromeno[5,6-e][1,3]oxazine, referred to herein as Compound 28, has the following properties: yellow viscous oil; $[\alpha]_D^{25}$ +22.5 (c 0.00067, $CH_2Cl_2$); IR ($CH_2Cl_2$) $v_{max}$ 3656, 2922, 2854, 1606, 1531, 1083 $cm^{-1}$; $^1H$- and $^{13}C$-NMR characteristics found in FIGS. 7A, 7B, and 15; and HREIMS m/z 587.3826, $[M+H]^+$ (calcd for $C_{37}H_{51}N_2O_4$, 587.3843).

(R)-6,8-dimethyl-2-(3-nitrobenzyl)-8-((3E,7E)-4,8,12-trimethyltrideca-3,7,11-trienyl)-1,2,3,8,9,10-hexahydrochromeno[5,6-e][1,3]oxazine, referred to herein as Compound 29, has the following properties: yellow viscous oil; $[\alpha]_D^{25}$ +2.77 (c 0.013, $CH_2Cl_2$); IR ($CH_2Cl_2$) $v_{max}$ 3676, 3599, 2922, 2854, 1606, 1540, 1374, 1084 $cm^{-1}$; $^1H$- and $^{13}C$-NMR characteristics found in FIGS. 7A, 7B, and 15; and HREIMS m/z 573.3669, $[M+H]^+$ (calcd for $C_{36}H_{49}N_2O_4$, 573.3687).

(R)-5-((3,4-dimethoxyphenethylamino)methyl)-2,7,8-trimethyl-2-((3E,7E)-4,8,12-trimethyltrideca-3,7,11-trienyl)chroman-6-ol, referred to as Compound 30, has the following properties: yellow viscous oil; $[\alpha]_D^{25}$ +6.0 (c 0.0013, $CH_2Cl_2$); IR ($CH_2Cl_2$) $v_{max}$ 3623, 3158, 2923, 1591, 1514, 1381, 1094, 855 $cm^{-1}$; $^1H$- and $^{13}C$-NMR characteristics found in FIGS. 7A, 7B, and 16; and HREIMS m/z 604.4371, $[M+H]^+$ (calcd for $C_{39}H_{58}NO_4$, 604.4360).

(R)-5-((4-hydroxyphenethylamino)methyl)-2,7,8-trimethyl-2-((3E,7E)-4,8,12-trimethyltrideca-3,7,11-trienyl)chroman-6-ol, referred to herein as Compound 31, has the following properties: yellow viscous oil; $[\alpha]_D^{25}$ +6.7 (c 0.0127, $CH_2Cl_2$); IR ($CH_2Cl_2$) $v_{max}$ 3582, 3322, 2917, 1612, 1513, 1379, 1173, 1095, 913 $cm^{-1}$; $^1H$- and $^{13}C$-NMR characteristics found in FIGS. 8A, 8B, and 16; and HREIMS m/z 560.4108, $[M+H]^+$ (calcd for $C_{37}H_{54}NO_3$, 560.4098).

(R)-5-(hydroxymethyl)-2,7,8-trimethyl-2-((3E,7E)-4,8,12-trimethyltrideca-3,7,11-trienyl)chroman-6-ol, referred to herein as Compound 32, has the following properties: yellow viscous oil; $[\alpha]_D^{25}$ +3 (c 0.05, $CH_2Cl_2$); IR ($CH_2Cl_2$) $v_{max}$ 3590, 3385, 2927, 1620, 1470, 890 $cm^{-1}$; $^1H$- and $^{13}C$-NMR characteristics found in FIGS. 8A, 8B, and 16; HREIMS m/z=423.1.

(R)-5-(hydroxymethyl)-2,8-dimethyl-2-((3E,7E)-4,8,12-trimethyltrideca-3,7,11-trienyl)chroman-6-ol, referred to herein as Compound 33, has the following properties: yellow viscous oil; $[\alpha]_D^{25}$ +2.6 (c 0.048, $CH_2Cl_2$); IR ($CH_2Cl_2$) $v_{max}$ 3595, 3393, 2922, 1607, 1469, 1378, 860 $cm^{-1}$; $^1$H- and $^{13}$C-NMR characteristics found in FIGS. 8A, 8B, and 16; and HREIMS m/z 425.3055, [M−H]+ (calcd for $C_{24}H_{41}O_3$, 425.3061).

(R)-7-(hydroxymethyl)-2,8-dimethyl-2-((3E,7E)-4,8,12-trimethyltrideca-3,7,11-trienyl)chroman-6-ol, Referred to herein as Compound 34, has the following properties: yellow viscous oil; $[\alpha]_D^{25}$ +0.9 (c 0.0066, $CH_2Cl_2$); IR ($CH_2Cl_2$) $v_{max}$ 3588, 3393, 2924, 1467, 1100, 985 $cm^{-1}$; $^1$H- and $^{13}$C-NMR characteristics found in FIGS. 8A, 8B, and 17; and HREIMS m/z 425.3074, [M−H]+ (calcd for $C_{24}H_{41}O_3$, 425.3061).

4-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)butan-1-ol, referred to herein as Compound 35, has the following properties: yellow viscous oil, $[\alpha]_D^{25}$ +8.4 (c 0.00166, $CH_2Cl_2$); IR ($CH_2Cl_2$) $v_{max}$ 3434, 2926, 1641, 1464, 1377, 1094, 954 $cm^{-1}$; $^1$H- and $^{13}$C-NMR characteristics found in FIGS. 9A, 9B, and 17; and HREIMS m/z 524.4095, [M+H]$^+$ (calcd for $C_{34}H_{54}NO_3$, 524.4098).

4-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)butan-1-ol, referred to herein as Compound 36, has the following properties: yellow viscous oil; $[\alpha]_D^{25}$ +10.6 (c 0.01133, $CH_2Cl_2$); IR ($CH_2Cl_2$) $v_{max}$ 3210, 2923, 1473, 1379, 1058, 859 $cm^{-1}$; $^1$H- and $^{13}$C-NMR characteristics found in FIGS. 9A, 9B, and 17; and HREIMS m/z 510.3936, [M+H]$^+$ (calcd for $C_{33}H_{52}NO_3$, 510.3941).

6-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)hexan-1-ol, referred to herein as Compound 37, has the following properties: yellow viscous oil; $[\alpha]_D^{25}$ +7.98 (c 0.0114, $CH_2Cl_2$); IR ($CH_2Cl_2$) $v_{max}$ 3617, 2924, 1465, 1378, 1095, 950 $cm^{-1}$; $^1$H- and $^{13}$C-NMR characteristics found in FIGS. 9A, 9B, and 17; HREIMS m/z 552.4410, [M+H]$^+$ (calcd for $C_{36}H_{58}NO_3$, 552.4411).

6-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)hexan-1-ol, referred to herein as Compound 38, has the following properties: yellow viscous oil; $[\alpha]_D^{25}$ +12.6 (c 0.019, $CH_2Cl_2$); IR ($CH_2Cl_2$) $v_{max}$ 3616, 2916, 1473, 1379, 1070, 1046, 939, 859 $cm^{-1}$; $^1$H- and $^{13}$C-NMR characteristics found in FIGS. 9A, 9B, and 18; and HREIMS m/z 538.4252, [M+H]$^+$ (calcd for $C_{35}H_{56}NO_3$, 538.4254).

8-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)octan-1-ol, referred to herein as Compound 39, has the following properties: yellow viscous oil; $[\alpha]_D^{25}$ +7.53 (c 0.013, $CH_2Cl_2$); IR ($CH_2Cl_2$) $v_{max}$ 3617, 2922, 1465, 1378, 1096, 950, 845 $cm^{-1}$; $^1$H- and $^{13}$C-NMR characteristics found in FIGS. 9A, 9B, and 18; and HREIMS m/z 580.4718, [M+H]$^+$ (calcd for $C_{38}H_{62}NO_3$, 580.4724).

8-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)octan-1-ol, Referred to herein as Compound 40, has the following properties: yellow viscous oil; $[\alpha]_D^{25}$ +7.69 (c 0.03223, $CH_2Cl_2$); IR ($CH_2Cl_2$) $v_{max}$ 3616, 2909, 1473, 1379, 1073, 1043, 940, 859 $cm^{-1}$; $^1$H- and $^{13}$C-NMR characteristics found in FIGS. 9A, 9B, and 18; and HREIMS m/z 566.4561, [M+H]$^+$ (calcd for $C_{37}H_{60}NO_3$, 566.4567).

10-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)decan-1-ol, referred to herein as Compound 41, has the following properties: yellow viscous oil, $[\alpha]_D^{25}$ +10.0 (c 0.0008, $CH_2Cl_2$); IR ($CH_2Cl_2$) $v_{max}$ 3615, 2928, 1463, 1378, 1098, 950, 846 $cm^{-1}$; and HREIMS m/z 608.5064, [M+H]$^{-1}$ (calcd for $C_{40}H_{66}NO_3$, 608.5037).

10-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)decan-1-ol, referred to herein as Compound 42, has the following properties: yellow viscous oil, $[\alpha]_D^{25}$ +7.7 (c 0.0056, $CH_2Cl_2$); IR ($CH_2Cl_2$) $v_{max}$ 3613, 2927, 1683, 1472, 1378, 1046, 860 $cm^{-1}$; and HREIMS m/z 594.4893, [M+H]$^{-1}$ (calcd for $C_{39}H_{64}NO_3$, 594.4881).

12-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)dodecan-1-ol, referred to herein as Compound 43, has the following properties: yellow viscous oil, $[\alpha]_D^{25}$ +0.5 (c 0.00213, $CH_2Cl_2$); IR ($CH_2Cl_2$) $v_{max}$ 3614, 3427, 2928, 1463, 1379, 1098, 950, $cm^{-1}$; HREIMS m/z 636.5361, [M+H]$^{-1}$ (calcd for $C_{42}H_{70}NO_3$, 636.5350).

12-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)dodecan-1-ol, referred to herein as Compound 44, has the following properties: yellow viscous oil, $[\alpha]_D^{25}$ +7.7 (c 0.00246, $CH_2Cl_2$); IR ($CH_2Cl_2$) $v_{max}$ 3616, 2909, 1473, 1379, 1073, 1043, 940, 859 $cm^{-1}$; HREIMS m/z 622.5181, [M+H]$^{-1}$ (calcd for $C_{41}H_{68}NO_3$, 622.5194).

FIG. 19 of the drawings represents a structure drawing of Compounds 1 and 2.

FIG. 20 of the drawings represents a structure generic to Compounds 11 and 25 with separate representations of substituent group R' that are particular to Compounds 11 and 25. As it appears in this and other figures, the substituent group $C_{16}H_{27}$ represents an unsaturated chain in the same form as the parent compound.

Now referring to FIGS. 21-23, FIG. 21 represents a structure generic to Compounds 3-10, 12-24, 26-29, and 35-44 having substituent groups R and R' listed in FIG. 22. Substituent groups indicated as "a," "b," "c," "d," "e," "f," and "g" in FIG. 22 have the structures indicated in FIG. 23.

FIG. 24 shows the structure of Compound 34.

FIG. 25 shows the structure that is generic to Compounds 32 and 33 and indicates the substituent groups of Compounds 32 and 33.

FIG. 26 shows the structure that is generic to Compounds 30 and 31 and indicates the substituent groups of Compounds 30 and 31 by reference to substituent groups "e" and "f" as shown in FIG. 23.

Compositions of matter described herein may, for example, comprise any one of Compounds 3-40 either individually or as a group. In a related embodiment, compositions of matter described herein may, for example, comprise a pharmaceutically acceptable salt of any one of Compounds 3-40.

Compositions of matter described herein may, for example, comprise a compound having the general formula:

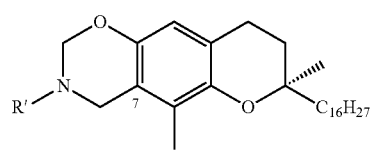

wherein R' is selected from

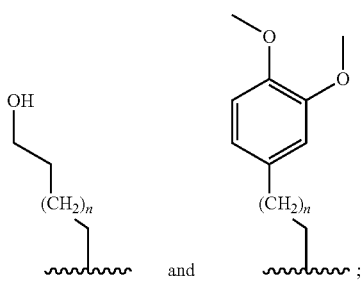

and
wherein "n" is an integer selected from 1, 2, 3, 4, 5, 6, and 7.

Compositions of matter described herein may, for example, comprise a compound having the general formula:

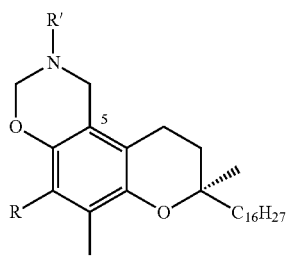

wherein R' is selected from

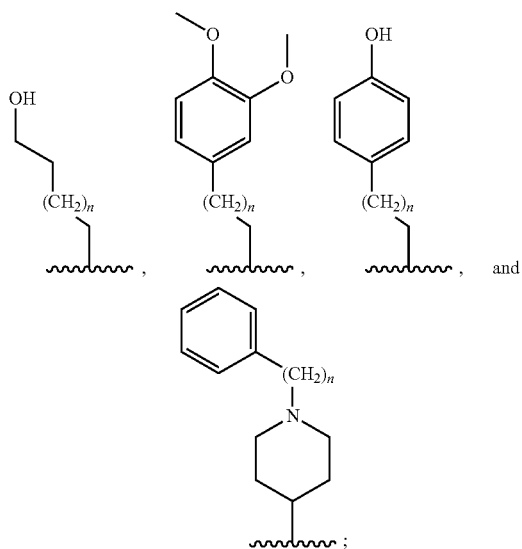

wherein "n" is an integer selected from 1, 2, 3, 4, 5, 6, and 7; and wherein R is selected from H and CH$_3$.

A method of treating or preventing a form of cancer may, for example, comprise administering to a mammalian patient in need of said treatment or prevention either a first therapeutic amount of a compound or a second therapeutic amount of a pharmaceutically acceptable salt of said compound, wherein said compound is selected from Compounds 3-44.

A method of treating or preventing a form of cancer may, for example, comprise exposing a mammalian cell to either a first therapeutic amount of a compound or a second therapeutic amount of a pharmaceutically acceptable salt of said compound, wherein said compound is selected from Compounds 3-44.

Compositions of matter described herein may, for example, comprise an in vivo product having anti-cancerous pharmacological effects produced by the administration of one of Compounds 3-44 to a mammalian patient.

Compositions of matter described herein may, for example, comprise a compound having the general formula:

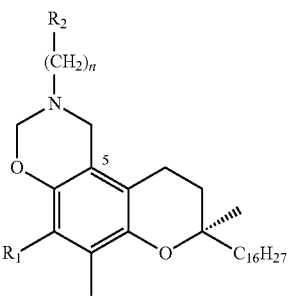

wherein R$_1$ is selected from H and CH$_3$; wherein n is selected from 1, 2, 3, 4, 5, 6, 7, 8, 9, 10, 11, and 12; wherein R$_2$ is selected from OH,

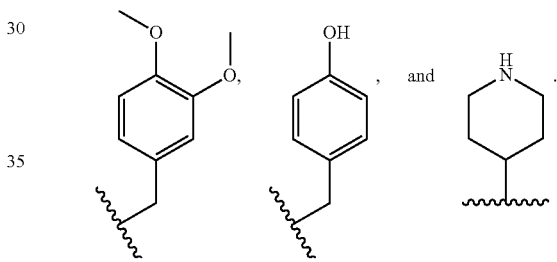

In a distinct but related embodiment, R$_2$ is selected from

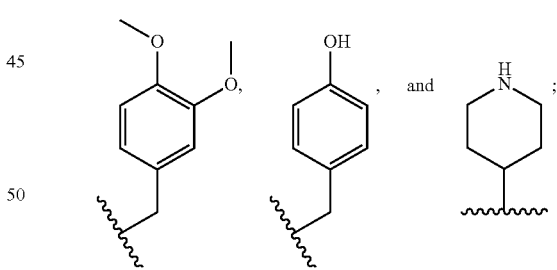

and n is selected from 1, 2, 3, and 4. In four additional distinct but related embodiments each relating back to the above general formula, R$_2$ is OH; "n" is selected from 4, 5, 6, 7, 8, 9, 10, 11, and 12; "n" is selected from 6, 7, 8, 9, and 10; and R$_1$ is H.

Compositions of matter described herein may, for example, comprise a composition of matter selected from: 10-((R)-5,6,8-trimethyl-8-((3E,7E)-4,8,12-trimethyltrideca-3,7,11-trienyl)-9,10-dihydrochromeno[5,6-e][1,3]oxazin-2(1H,3H,8H)-yl)decan-1-ol; 10-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)decan-1-ol; 12-((R)-5,6,8-trimethyl-8-((3E,7E)-4,8,12- trimethyltrideca-3,7,11-trienyl)-9,10-dihydrochromeno[5,6-e][1,3]oxazin-2(1H,3H,8H)-yl)dodecan-1-ol; and 12-((R)-6,8-dimethyl-8-((3E,7E)-4,8,12-trimethyltrideca-3,7,11-trienyl)-9,10-dihydrochromeno[5,6-e][1,3]oxazin-2(1H,3H,8H)-yl)dodecan-1-ol.

BRIEF DESCRIPTION OF THE DRAWINGS

FIGS. 1A, 1B, 2A, 2B, 3, 4, 5A, 5B, 6A, 6B, 7A, 7B, 8A, 8B 9A, 9B, 10, 11, 12, 13, 14, 15, 16, 17, and 18 show $^1$H- and $^{13}$C-NMR characteristics of Compounds 3-44.

FIG. 20 shows the structure of Compounds 11 and 25.
FIGS. 21, 22, and 23 show the structure of Compounds 3-10, 12-24, 26-29, and 35-44.
FIG. 27 identifies amines used in the synthesis of various compounds.
FIG. 28 shows $IC_{50}$ data for Compounds 3-44.
FIGS. 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74 indicate the growth inhibition effects of Compounds 8, 13, 18, 24, 27, 35, 36, 37, 38, 39, 40, 41, 42, 43, and 44 against a variety of cell lines.
FIGS. 75, 76, 77, 78, 79, 80, 81, 82, 83, 84, 85, 86, 87, 88, 89, 90, 91, 92, 93, 94, 95, 96, 97, 98, 99, and 100 indicate the calculated $GI_{50}$, TGI, and $LC_{50}$ values for Compounds 8, 13, 17, 18, 23, 24, 27, 35-40, and 44 in molar concentrations against a variety of cell lines.

EXAMPLES

Example 1

Figure 19:
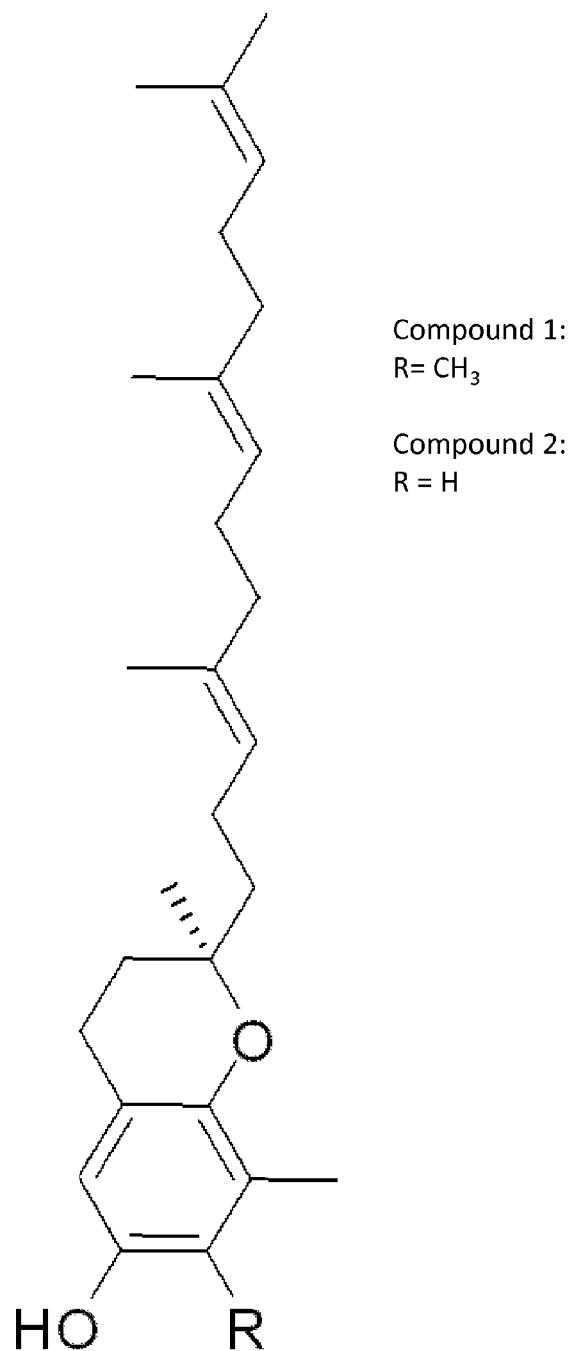
FIG. 19 shows the structure of Compounds 1 and 2.

Semisynthesis of Tocotrienol
3,4-dihydro-1,3-oxazine Analogs

Compounds 3-29 and 35-44 were prepared in a Mannich-type reaction sequence. Equimolar amounts of tocotrienol, primary amine, and formaldehyde were condensed to produce Compounds 3-29 and 35-44 rather than the corresponding Mannich bases. FIG. 27 describes which amines were used in the synthesis of various compounds described herein. Synthesis of Compounds 41-44 is carried out using amines comparable to the amines used in the preparation of Compounds 37-40 but with longer amine lengths appropriate for the desired final product. In FIG. 27 the left column indicates the compound number of the compound that was synthesized and the right column describes the amine that was used in the synthesis. Some literature indicates that the Mannich bases would have been the expected product of such a reaction. Not wishing to be bound by theory, this discrepancy may be attributed, in part, to the use of primary amines, which have two formaldehyde reactive sites and subsequently one hydrogen can be substituted to give the aminomethyl analogue, or the two hydrogen atoms are substituted to give either the dihydro-1,3-oxazine or bis-substituted tertiary amine Both Compound 1 and Compound 2 were employed and they underwent the reaction successfully. Because Compound 2 has two unsubstituted o-positions (C-5 and C-7), it was expected to get positional isomers in the reaction products. The C-5 substituted product was the predominant species because of the higher reactivity of C-5 than C-7. The reaction proceeded toward the 1,3-oxazine formation regardless the molar ratio of the reactants or the order of mixing, indicating that the reactants can all be mixed together with the primary amine Either dioxane or ethanol was used and occasionally the reaction was allowed to proceed under solventless conditions. Synthesis was successful with both aqueous formaldehyde and paraformaldehyde. Either of Examples 1A or 1B described below may be used to prepare Compounds 3-29 and 35-44.

Example 1A

To a dioxane solution (5 mL) of tocotrienol (4 mmoles), the amine (20 mmoles) was added. Mixture was cooled in an ice bath and 37% formaldehyde (21 mmoles) was added drop wise while stirring. It was then stirred at room temperature for 1 hour and then refluxed overnight. The reaction mixture was concentrated under vacuum and the yellow residue obtained was dissolved in ethyl acetate (20 mL), washed several times with saturated NaCl solution, dried over anhydrous $MgSO_4$, and concentrated in vacuum. The residue obtained was subjected to column chromatography using normal phase silica gel as stationary phase and gradient ethyl acetate/n-hexane system as mobile phase. Reaction products were identified by spectrometric analysis experiments.

Example 1B

A mixture of tocotrienol (5.0 mmoles), paraformaldehyde (5.0 mmoles) and amines (5.0 mmoles) was stirred and left overnight at room temperature. The reaction was either carried out under solventless conditions or a few drops of an organic solvent were added (dioxane, ethanol). The residue was purified by flash chromatography directly from the reaction mixture without any work-up. The products were characterized using different spectrometric analysis experiments.

In the syntheses described above as Examples 1A and 1B, allylamine and 2-aminoethanol were used as primary amines with medium chain length and different terminal functionalities. Equimolar amounts of Compound 2 were refluxed with allylamine or 2-aminoethanol with HCHO in dioxane. The reactions produced Compound 5 and Compound 9 respectively.

Further, in the syntheses described above as Example 1A and 1B, δ-Tocotrienol, Compound 2, reacted with 2-aminoethanol and HCHO to give the positional isomers Compound 10 (major) and Compound 11 (minor). Still further, in the syntheses described above as Examples 1A and 1B, Aminopropanol, 3,3-diethoxypropylamine, aminopentanol, 3,4-dimethoxyphenethylamine, and tyramine were also condensed with either Compounds 1 or 2 to produce Compounds 12 or 13, 14 or 15, 17 or 18, 23 or 24 and 25, and 26 or 27, respectively.

Example 2

Preparation of Mannich Base Analogs of Tocotrienol 3,4-Dihydro-1,3-oxazine analogs, namely Compounds 23 and 26, were hydrolyzed in a methanol solution to give the corresponding Mannich bases, Compounds 30 and 31 respectively, with the concomitant loss of one molecule of formaldehyde. The later were produced at a yield of 15-20%. Specifically, the starting compound was dissolved in 75% methanol and left for 48 hours at room temperature under shaking conditions (125 rpm). The solution was concentrated in vacuum and then extracted with dichloromethane (3×100 mL) The organic solvent was evaporated under vacuum and the residue purified using column chromatography.

Example 3

Semisynthesis of Hydroxymethyl Tocotrienol Analogs

In a Lederer-Manasse reaction, a toluene solution of tocotrienol was refluxed with paraformaldehyde in presence of boric and acetic acids to produce the hydroxylmethyl tocotrienol analogs, Compounds 32-34. δ-Tocotrienol, Compound 2, produced two positional isomers, Compounds 33 and 34, because of the availability of two reactive sites, C-5 and C-7. γ-tocotrienol, Compound 1, reacted to produce Compound 32 under similar conditions.

Preparation of the hydroxymethyl analogs involved the following: To a toluene solution of tocotrienol (25 mmoles, 5 mL), acetic acid (0.5 mL), boric acid (40 mmoles), and paraformaldehyde (2.4 g) were added. The mixture was refluxed overnight. The reaction was stopped by cooling and washing with cold water, followed by vigorous shaking with a $Na_2CO_3$ aqueous solution (5% W/V) for 0.5 hours, to decompose the boric acid complex. Finally, the mixture was washed with water and dried over anhydrous $Na_2SO_4$ and concentrated under vacuum. The residue was subjected to column chromatography using normal phase silica gel as stationary phase and gradient n-hexane/ethyl acetate system as mobile phase. Reaction products were identified by spectrometric analysis.

Example 4A

MTT Assay of +SA Cells

The antiproliferative activities of Compounds 3-44 against the highly metastatic malignant +SA mammary epithelial cells were evaluated by MTT assay. Materials for the assay were purchased from Sigma Chemical Company (St. Louis, Mo.) unless otherwise stated. The highly malignant +SA mouse mammary epithelial cell line was serially passaged at subconfluent cell density. The +SA mammary tumor cell line was derived from an adenocarcinoma that developed spontaneously in a BALB/c female mouse. +SA cells were maintained in serum-free defined medium consisting of Dulbecco's modified Eagle's medium (DMEM)/F12 containing 5 mg/mL bovine serum albumin (BSA), 10 mg/mL transferrin, 100 U/mL soybean trypsin inhibitor, 100 U/mL penicillin G, 0.1 mg/mL streptomycin, 10 mg/mL insulin, and 10 ng/mL epidermal growth factor. For subculturing, cells were rinsed twice with sterile Ca2+ and Mg2+-free phosphate buffered saline (PBS) and incubated in 0.05% trypsin containing 0.025% EDTA in PBS for 5 min at 37° C. The released cells were centrifuged, resuspended in fresh media and counted using hemocytometer. A stock solution of the compounds was prepared in DMSO. Once dissolved, this solution was added to a small volume of sterile 10% BSA in water and incubated overnight at 37° C. This solution conjugated to BSA was used to prepare various concentrations (0-40 μM) of tocotrienol analogs. DMSO was added to all treatment media such that the final DMSO concentration was the same in all treatment groups within a given experiment and was always less than 0.1%. For cytotoxic studies, cells were seeded at a density of $5\times10^4$ cells/well (+SA cells) or $1\times10^5$ cells/well (CL-S1 cells) (6 wells/group) in 24-well culture plates and allowed to grow in their respective control media. After 3 days incubation period (approximately 70% confluency), cells were divided equally into various treatment groups and exposed to their respective treatments for a 24 hours incubation period. Following the 24 hours treatment period, cell viability was measured using the MTT assay.

+SA Mammary epithelial cell viable number was determined by a 3-(4,5-dimethylthiazol-2yl)-2,5-diphenyl tetrazolium bromide (MTT) colorimetric assay. On the assay day, treatment medium was replaced with fresh control medium containing 0.42 mg/mL MTT, and the cells in 24-well plates were incubated at 37° C. for 4 hours. Afterward, the medium was removed, and the MTT crystals were dissolved in isopropyl alcohol (1 mL/well). The optical density of each sample was read at 570 nm on a microplate reader (Spectra-Count, Packard BioScience Company), against a blank prepared from cell-free cultures. The number of cells/well was calculated against a standard curve prepared by plating various concentrations of cells, as determined by hemocytometer, at the start of each experiment.

Differences among the various treatment groups in +SA cell cytotoxic studies were determined by analysis of variance (ANOVA) followed by Dunnett's t-test. The difference of $P<0.05$ was considered to be statistically significant as compared with vehicle-treated controls unless separately described. Linear regression analysis of treatment effects on viable cell number in growth and cytotoxicity studies was used to determine the 50% growth inhibition concentration ($IC_{50}$) for individual treatments.

FIG. 28 shows $IC_{50}$ data for Compounds 3-44 against the +SA mammary epithelial cells.

Figure 29:
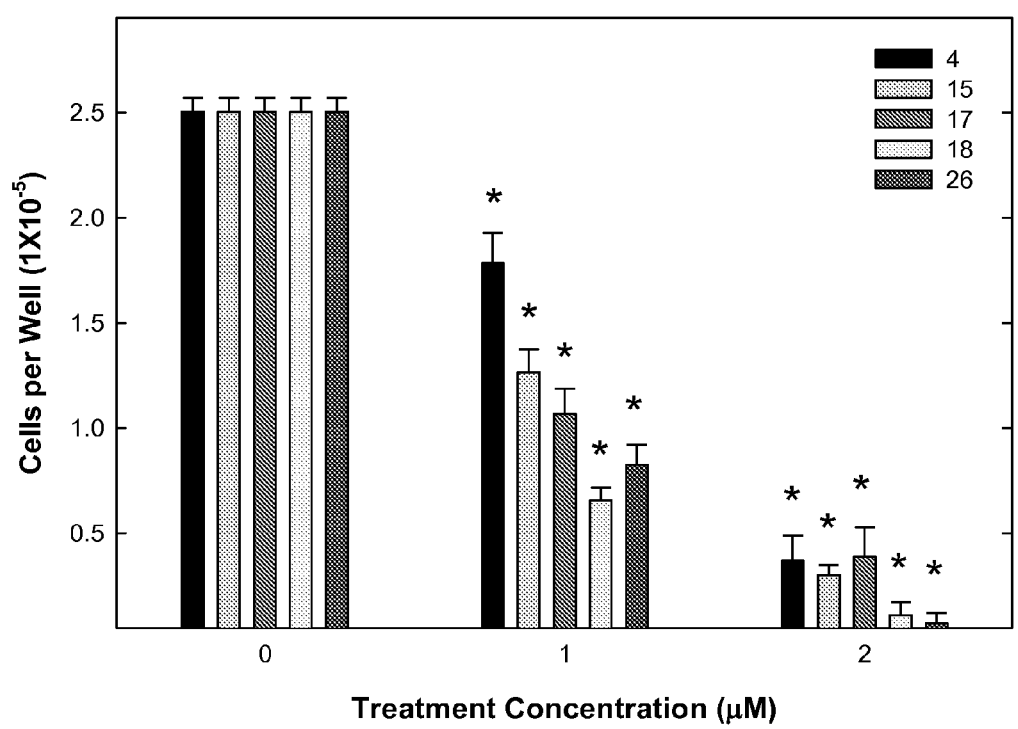
FIG. 29 shows anti-proliferative treatment data for Compounds 4, 15, 17, 18, and 26.

FIG. 29 shows the effects of Compounds 4, 15, 17, 18, and 28 on the viability of +SA mammary tumor cells. Reading FIG. 29 from left to right cell counts are given for Compound 4, Compound 15, Compound 17, Compound 18, and Compound 26 for treatment concentrations of 0 μM (control), then for 1 μM, and then for 2 μM.

Figure 30:
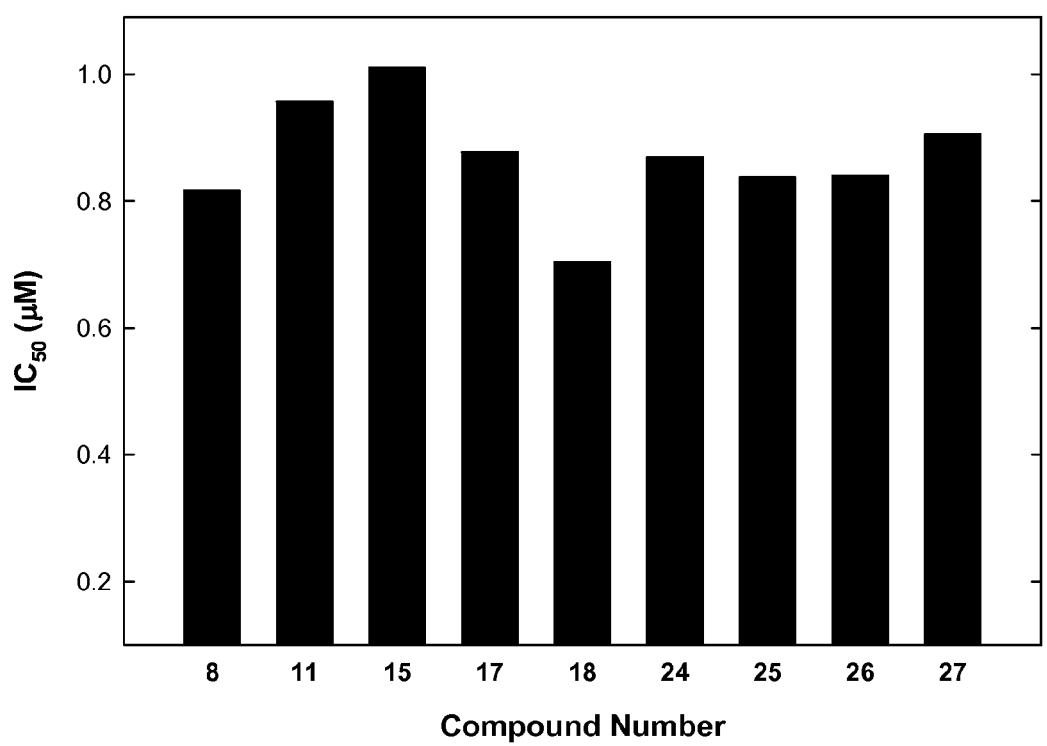
FIGS. 30, 31, 32, 33, and 34 show $IC_{50}$ data for disclosed compounds.

FIG. 30 shows antiproliferative activity for several tested compounds as $IC_{50}$ values. FIG. 30 shows the antiproliferative activities of Compounds 8, 11, 15, 17, 18, 24, 25, 26, and 27 against +SA mammary tumor cells.

Figure 31:
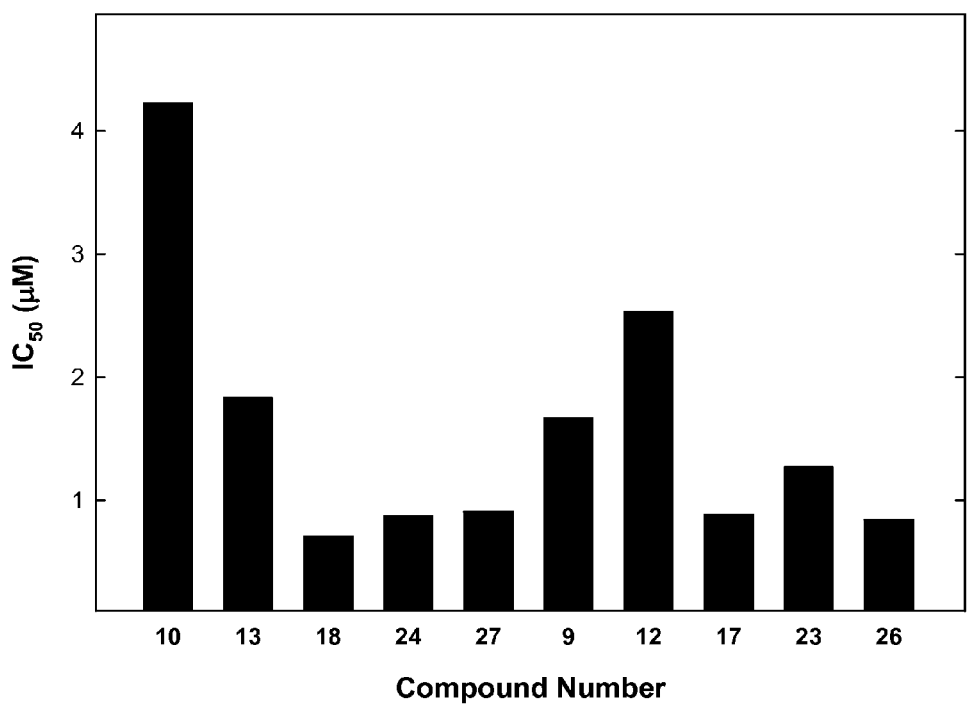

FIG. 31 shows antiproliferative activity for several tested compounds as $IC_{50}$ values. FIG. 31 shows how semi-synthesis with amines of varying length impacts antiproliferative activity and how compounds derived from δ-tocotrienol (Compounds 10, 13, 18, 24, 27) compared to compounds derived from γ-tocotrienol (Compounds 9, 12, 17, 23, 26) in activity against +SA mammary tumor cells.

Figure 32:
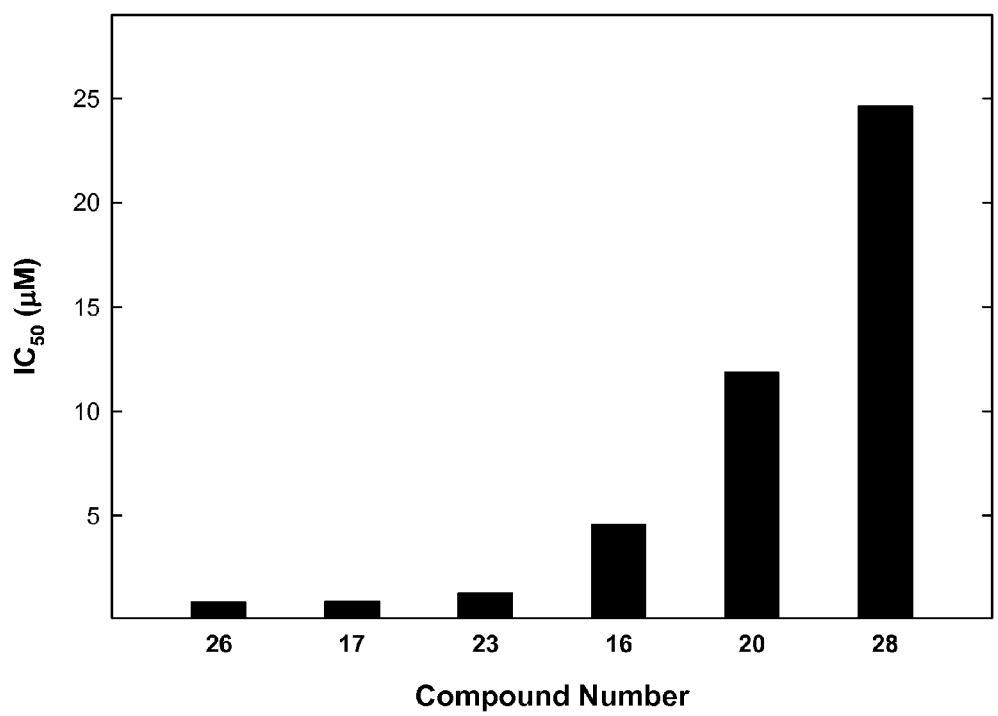

FIG. 32 shows antiproliferative activity for several tested compounds as $IC_{50}$ values. FIG. 32 demonstrates the importance of the terminal amine functional group against +SA mammary tumor cells. Compounds 17 and 26 which have a free OH group have very high activities. Compound 23 has terminal $OCH_3$ groups and also displayed very high activity. Compound 16 which terminates in an NH group showed strong activity. Compound 20 which terminates in a carboxylic acid group showed strong activity but less so than the aforementioned compounds. Compound 28 which terminates in $NO_2$ showed significant activity but less so than Compounds 20.

Figure 33:
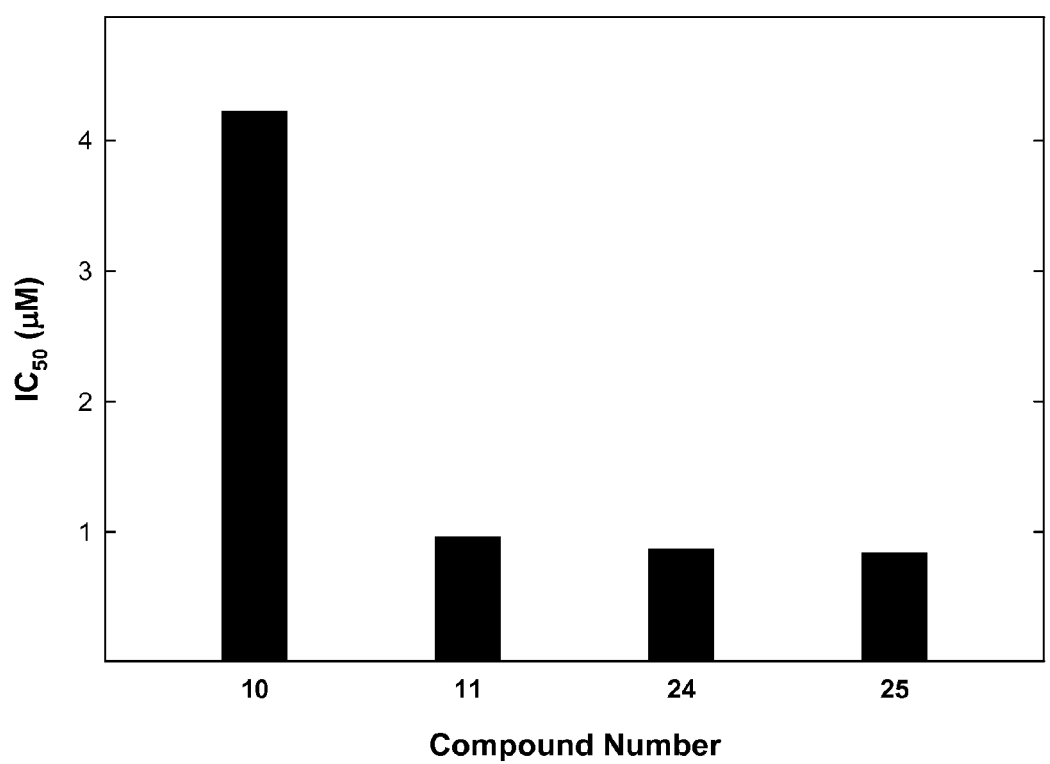

FIG. 33 shows antiproliferative activity for several tested compounds as $IC_{50}$ values. FIG. 33 shows the variation of the activity of different δ-tocotrienol positional isomers against +SA mammary tumor cells. The reactant 2-aminoethanol was used to produce Compounds 10 and 11 which are isomers. FIG. 33 shows that Compounds 10 and 11 varied significantly in potency while Compounds 24 and 25 isomers created with 3,4-dimethoxyphenethylamine have nearly equal potency.

Figure 34:
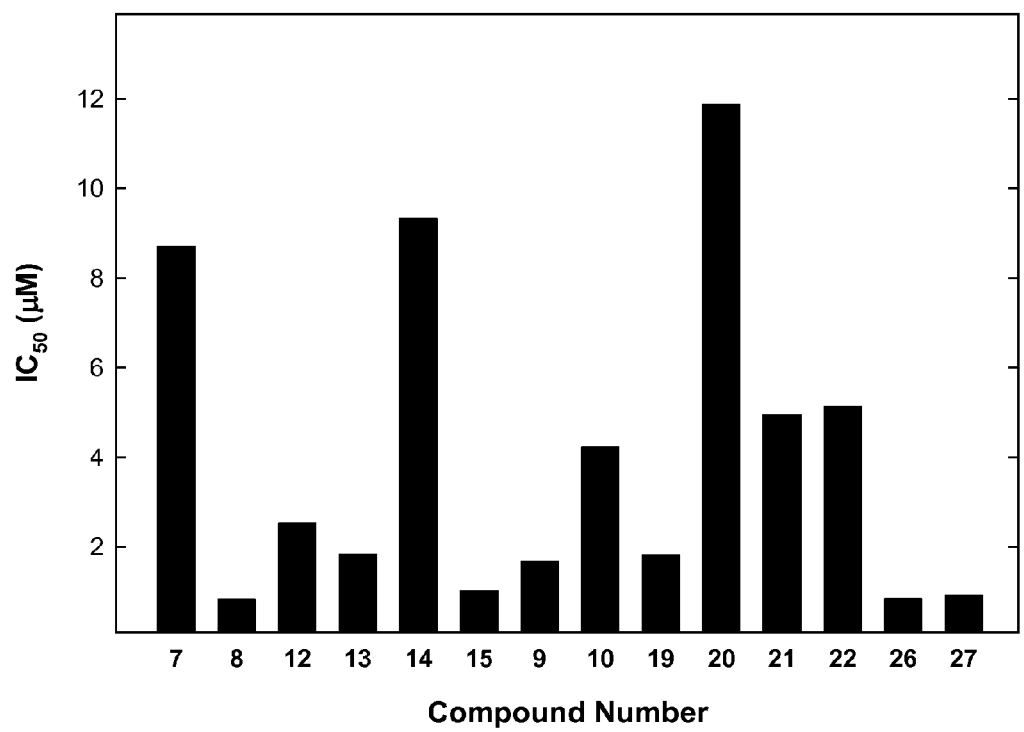

FIG. 34 shows antiproliferative activity for several tested compounds as $IC_{50}$ values. In FIG. 34 γ-tocotrienol and δ-tocotrienol isomer analogs appear next to each other for comparison purposes.

Not wishing to be bound by theory, the presence of a terminal OH group such as in Compound 9 may be important for the activity of the compound. However, compounds with N-methyl, such as Compounds 3 and 4, or N-benzyl groups, such as Compound 6, also showed good antiproliferative activities ($IC_{50}$ range of 1.2-2.2 μM), superior to those of Compounds 1 and 2 ($IC_{50}$ of 4 and 3 (μM, respectively). Further, extending the length of the alkyl chain of the primary amine proved to enhance the activity. This pattern was more evident in analogs of Compound 2 than it was for analogs of Compound 1. Masking the OH by etherification did not affect the activity with the exception of Compound 14 which showed a significantly decreased activity.

The terminal OH group, either free (Compounds 17 and 26) or etherified (Compounds 23), was the most active compared to other terminal groups such as COOH (Compound 20), NH (Compound 16), and $NO_2$ (Compound 28).

Although Compound 2 has two available o-positions for aminomethylation, the reaction proceeded predominantly at the position that is a to the pyran ring. Two positional isomers Compounds 10 and 11 were isolated after reacting Compound 2 with 2-aminoethanol while 3,4-dimethoxyphenethylamine afforded Compounds 24 and 25. Although Compound 11 was significantly more active than Compound 10, both Compounds 24 and 25 were nearly equipotent.

The antiproliferative activities of Compound 30 ($IC_{50}$ 3.19 (μM) and Compound 31 $IC_{50}$ 0.47 (μM) against the highly metastatic +SA mammary epithelial cancer cell line were higher than the activity of Compound 1.

Hydroxymethylation did not remarkably affect the activity. Only Compound 32 showed better activity than Compound 1 against the +SA mammary epithelial cells, with $IC_{50}$ value 2.6 (μM). Meanwhile, Compounds 33 and 34 were less active than Compound 2 and had $IC_{50}$ values of 6.6 μM and higher.

Thirty out of 42 prepared compounds have shown $IC_{50}$ values less than 3 μM, with better activity than δ-tocotrienol (Compound 2). Of these, seven compounds showed nanomolar $IC_{50}$ values.

Generally, the oxazine analogs of Compound 2 (δ-isomer) showed lower $IC_{50}$ values than the corresponding analogs of Compound 1 (γ-isomer). This pattern was consistent along most of the prepared oxazines except this pattern was reversed in the Manasse-Lederer-based analogs, Compounds 32-34. The γ-isomer analog Compound 32 showed lower $IC_{50}$ value the than the δ-isomers, Compounds 33 and 34.

Example 4B

MTT Assay of MCF7 and MDA-MB-231 Cells

The antiproliferative effects of tocotrienol analogs on the highly metastatic MDA-MB-231 and MCF7 human breast cancer cell lines were evaluated using procedures comparable to those described in Example 4A. MDA-MB-231 and MCF7 cells were plated at a density of $8\times10^3$ cells/well and $10^4$ cells/well in 96-well culture plates, respectively. The compounds were fed in serum free media containing 5% and 1% fetal bovine serum for MDA-MB-231 and MCF7 cells, respectively. Antiproliferative activity of various compounds displayed as $IC_{50}$ values (μM) against the highly metastatic MDA-MB-231 and MCF7 human cancer cell lines and the non-tumorigenic MCF 10A epithelial cell line is shown in Table I. $IC_{50}$ values were calculated using statistical software.

TABLE I

| Compound | MCF7 | MDA-MB-231 | MCF 10A |
|---|---|---|---|
| 1 | 7.1 | 9.4 | 4.4 |
| 6 | >20.0 | 27.3 | |
| 10 | 6.0 | >5.0 | 3.1 |
| 12 | >20.0 | 9.6 | |
| 13 | >20.0 | >10.0 | 6.5 |
| 16 | >20.0 | 0.8 | |
| 17 | >20.0 | >50.0 | 8.9 |
| 18 | 9.1 | 9.0 | 4.6 |
| 23 | >20.0 | >50.0 | 0.7 |
| 26 | 10.6 | >5.0 | 8.5 |
| 27 | 18.2 | >5.0 | 1.9 |
| 35 | >20.0 | 13.8 | |
| 36 | 16.3 | >5.0 | 4.2 |
| 37 | >20.0 | >10.0 | |
| 38 | >20.0 | >5.0 | 2.5 |
| 39 | >20.0 | >20.0 | 2.0 |
| 40 | >20.0 | 11.7 | 1.7 |
| 41 | 19.4 | 15.7 | |
| 42 | 4.6 | 12.4 | |
| 43 | >20.0 | >50.0 | |
| 44 | >20.0 | >50.0 | |

Example 4C

MTT Assay of MCF10A Cells

MCF 10A (ATCC cat # CRL-10317) normal human non-tumorigenic mammary epithelial cells were maintained in serum-free defined medium consisting of Dulbecco's modified Eagle's medium (DMEM)/F12 containing 5% horse serum, 1% penicillin/streptomycin, 0.5 μg/mL hydrocortisone, 100 ng/mL cholera toxin, 10 μg/mL insulin, and 20 ng/mL epidermal growth factor (rhEGF). For subculturing, cells were rinsed twice with sterile Ca2+ and Mg2+-free phosphate buffered saline (PBS) and incubated in 0.25% trypsin containing 0.025% EDTA in PBS for 5 min at 37° C. The released cells were centrifuged, re-suspended in fresh media and counted using a hemocytometer. For testing, MCF 10A cells were plated at a density of $10\times10^4$ cells/well. A stock solution of the compounds was prepared in DMSO. DMSO was added to all treatment media such that the final DMSO concentration was the same in all treatment groups within a given experiment and was always less than 0.1%. The compounds were fed in serum free media. MCF10A mammary epithelial cell's viable number was determined by MTT colorimetric assay. Antiproliferative activity of selected active compounds against the MCF10A cell line are displayed in Table II below. $IC_{50}$ values were calculated by non-linear regression using statistical software. The selectivity index indicated in the table represents the $IC_{50}$ value for the MCF 10A cell line divided by the $IC_{50}$ value for the +SA cell line.

TABLE II

| Compound | MCF10A | Selectivity index |
|---|---|---|
| 1 | 4.4 | 1.10 |
| 13 | 6.5 | 3.61 |
| 17 | 8.9 | 5.24 |
| 18 | 4.6 | 6.57 |
| 23 | 0.7 | 0.39 |
| 26 | 8.5 | 5.67 |
| 27 | 1.9 | 2.09 |
| 36 | 4.2 | 2.34 |
| 38 | 2.5 | 1.92 |
| 39 | 2.0 | 1.43 |
| 40 | 1.7 | 2.15 |

Example 5

Wound-Healing Assay

The highly metastatic human breast cancer MDA-MB-231 cells were cultured in RPMI 1640 medium containing 10 mM HEPES, 4 mM L-glutamine, 10% fetal bovine serum, penicillin (100 IU/mL), and streptomycin (50 µg/mL), and grown in a 5% $CO_2$ atmosphere at 37° C. Cells were plated onto sterile 24-well and allowed to recover for a confluent cell monolayer formed in each well (>95% confluence). Wounds were then inflicted to each cell monolayer using a sterile 200 µL pipette tip. Media were removed, cells monolayers were washed twice with PBS, and then fresh media containing test compounds were added to each well. Test compounds were prepared in DMSO at 5 µM concentration and added to the plates, each in triplicate using DMSO as negative control. The incubation was carried out for 24 h under serum-starved conditions, after which media was removed and cells were fixed and stained using a staining composition sold under the trade name Diff Quick (Dade Behring Diagnostics, Aguada, Puerto Rico). The stain comprised a fixative reagent containing 1.8 mg/L triarylmethane dye in methyl alcohol; a first solution of 1 g/L xanthene dye, buffer, and sodium azide (0.01%) as preservative; and a second solution of 1.25 g/L Thiazine dye mixture (0.625 g/L azure A and 0.625 g/L methylene blue) and buffer. The number of cells migrated on the scratched wound were counted under the microscope in three or more randomly selected fields (magnification: 400×). Final results are expressed as mean±SEM per 400× field. The wound-healing assay is a simple method for the study of directional cell migration in vitro.

Figure 35A:
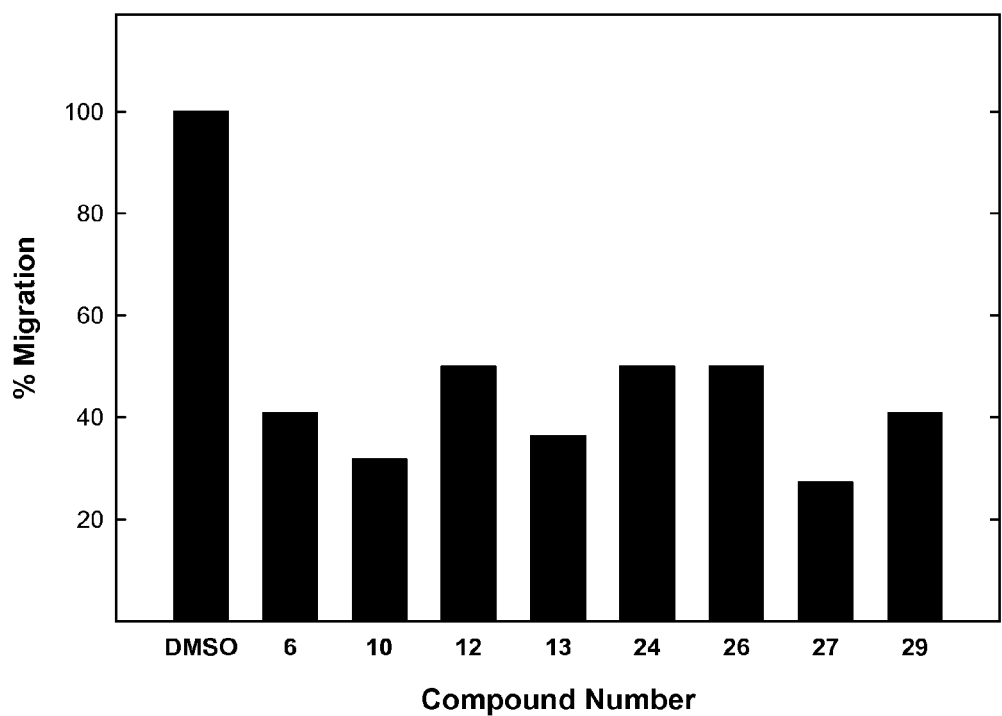
FIGS. 35A and 35B show anti-migratory activity of Compounds 6, 10, 12, 13, 24, 26, 27, and 29 and Compounds 12, 27, 35, 39, 40, and 42 respectively.

Compounds were tested for their ability to inhibit the migration of the highly metastatic MDA-MB-231 human breast cancer cells in the wound-healing assay using the procedure described above. Compounds 6, 10, 12, 13, 24, 26, 27, and 29 inhibited the migration of more than 50% of the human breast cancer cells MDA-MB-231 in the wound healing assay at 5 µM dose. FIG. 35 shows the anti-migratory activity of the most active analogs, Compounds 6, 10, 12, 13, 24, 26, 27, and 29, against the human highly metastatic breast cancer cells MDA-MB-231 in that wound-healing assay. Although most of the active compounds in wound healing assay were also active as antiproliferative, Compounds 6 and 29 were highly active as antimigratory but were inactive as antiproliferative. The antimigratory activity of tocotrienols may be enhanced by a terminal aromatic functionality. The presence of electron withdrawing group, such as nitro in Compound 29, may eliminate the antiproliferative activity yet retain the antimigratory activity of the compound. While the electron donating groups, such as OH and OMe found in Compounds 23 and 26, respectively, retained both antiproliferative and antimigratory activities.

Figure 35B:
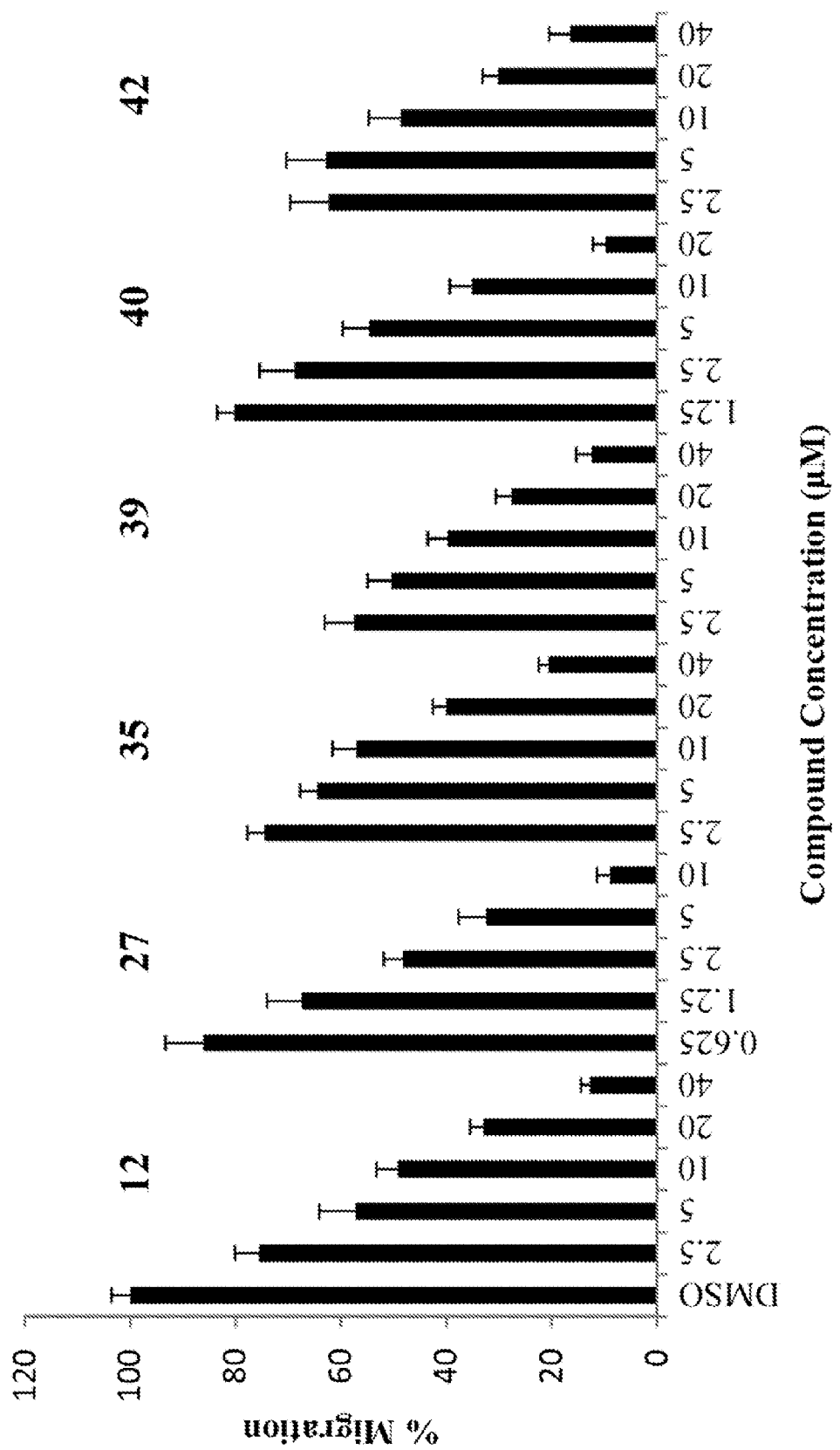

Utilizing similar procedures follow-up testing was conducted on a variety of compounds using a range of compound concentrations. The results of follow-up antimigratory testing are shown in FIG. 35B and Table III below with $IC_{50}$ values calculated using statistical software. FIG. 35 B shows the dose response antimigratory activity of Compounds 12, 27, 35, 39, 40, and 42 against the highly metastatic MDA-MB-231 human breast cancer cells in the wound-healing assay. $IC_{50}$ values were calculated for the tocotrienol analogs that had the greatest antimigratory activity against the highly metastatic human breast cancer cell line MDA-MB-231 and are presented below in Table III.

TABLE III

| Compound | $IC_{50}$ (µM) |
|---|---|
| 1 | >40.0 |
| 2 | >40.0 |
| 10 | 1.3 |
| 12 | 8.1 |
| 13 | 6.0 |
| 26 | 4.5 |
| 27 | 2.4 |
| 35 | 10.7 |
| 36 | 2.2 |
| 38 | 1.5 |
| 39 | 4.7 |
| 40 | 4.9 |
| 42 | 7.2 |

Figure 21:
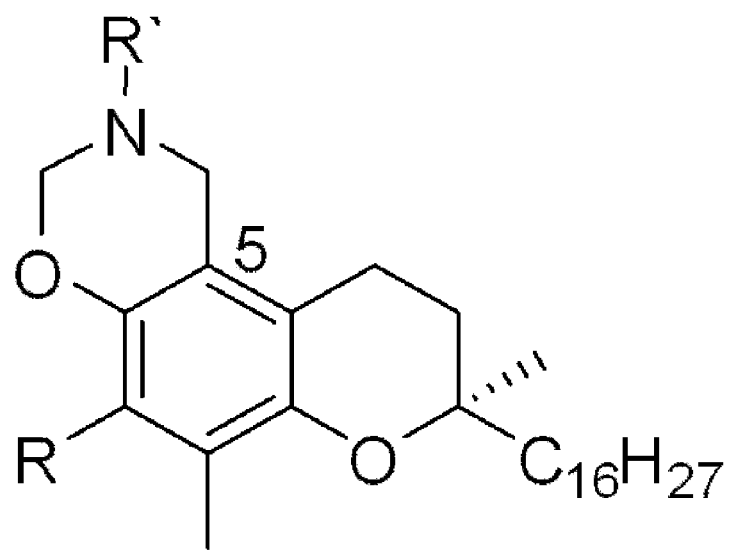
Figure 23:
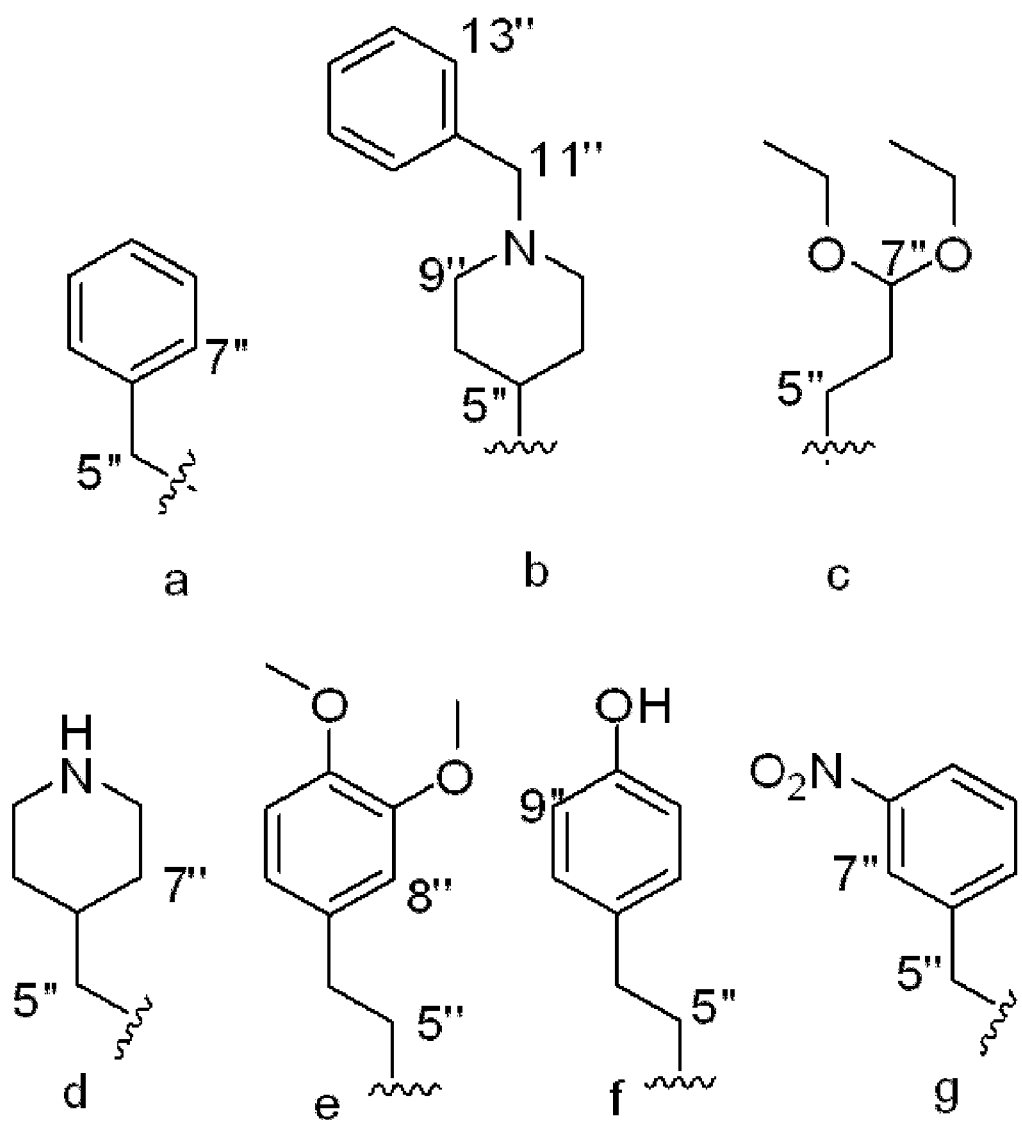
Figure 24:
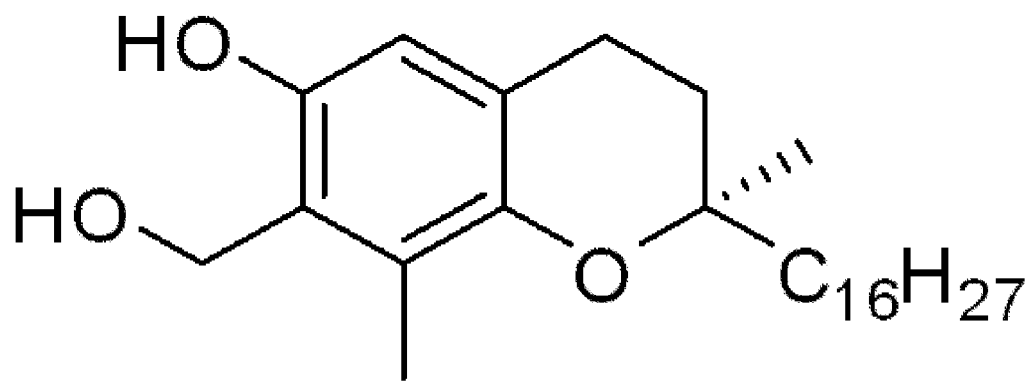
FIG. 24 shows the structure of Compound 34.
Figure 25:
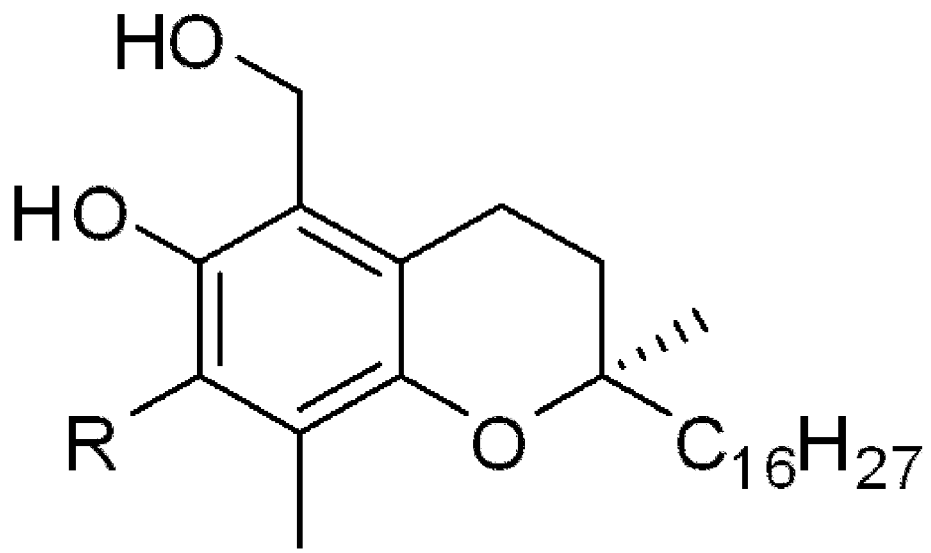
FIG. 25 shows the structure of Compounds 32 and 33.
Figure 26:
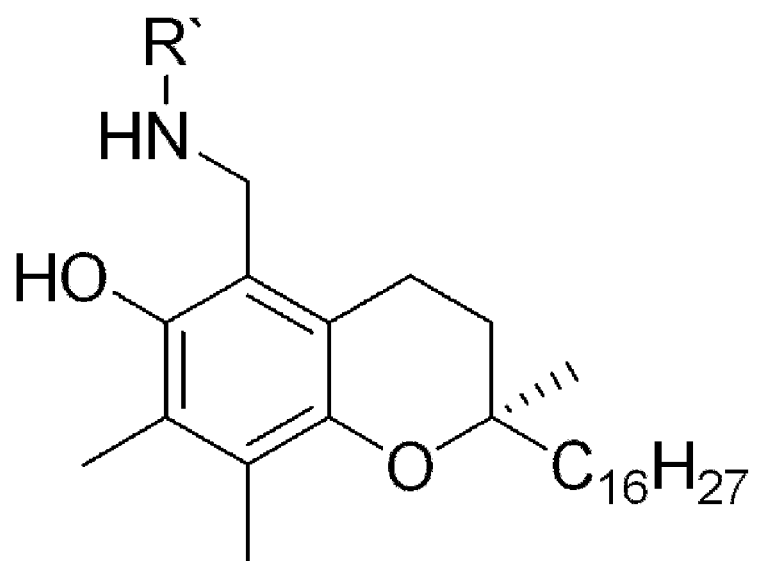
FIG. 26 shows the structure of Compounds 30 and 31.

Test results indicated that the 1,3-oxazine analogs were more active than the Mannich bases and the hydroxymethyl derivatives as antimigratory agents. A terminal OH group, alcoholic or phenolic, may also be important for antimigratory activity. Also, the oxazine analogs of 2 (δ-isomer) were more active than the corresponding analogs of Compound 1 (γ-isomer) as antimigratory agents. The most active compounds were Compounds 10, 38, 36, and 27 with $IC_{50}$ values of 1.3, 1.5, 2.2, and 2.4 µM, respectively. Compounds 10, 38, and 36 possess linear aliphatic ethanol, hexanol, or butanol side chains attached at R' as shown in FIG. 21. This is evidence of a potential preference for a terminal free hydroxy functionality at 2-6 carbons distance from at R' as shown in FIG. 21. The only analog among the most active compounds with aromatic (tyramine) side chain, Compound 27, can still be envisioned as a 6-carbons chain separating the free phenol hydroxy from the position of connection represented by R' as shown in FIG. 21.

Example 6

Tumor Implantation into Mammary Fat Pads of Syngeneic BALB/c Mice

The malignant +SA mammary epithelial cell line was derived from an adenocarcinoma that developed spontaneously in a female BALB/c mouse. These cells can be grown on plastic in culture and display the ability to grow in soft agarose. Re-implantation of +SA mammary tumor cells back into the mammary fat pad of syngeneic mice results in the rapid development and growth of metastatic tumors. Prior to experimentation, +SA cells were serially passaged at subconfluent cell density. For subculturing, cells are rinsed with calcium/magnesium-free phosphate buffered saline (PBS) and incubated in 0.05% trypsin containing 0.025% EDTA in PBS for 5 min at 37° C. The released cells are then diluted in a nutrient mixture sold as Dulbecco's Modified Eagle Medium: Nutrient Mixture F-12 media and pelleted by centrifugation. Cell pellets are then resuspended in control culture media, counted by hemocytometer, and then plated at the desired density in culture plates. Cells were then fed fresh media every other day. On the day of tumour implantation, +SA cells grown in culture are isolated with trypsin, washed, counted and diluted to the desired concentration in fresh culture medium. Female BALB/c mice, 3-4 months old, were purchased from Harlan laboratories (Indianapolis, Ind.) and housed in plastic cages in a temperature-regulated (24±0.5° and light-controlled (14 hr light/10 hr dark) room and allowed standard laboratory mouse chow and water ad libitum. At the time of experimentation, animals were anesthetized with an ip injection of ketamine/xylazine (10 mg ketamine:1 mg xylazine/mL saline, Henry Schein, Inc, Melville, N.Y.) at a dose of 0.1 mL/10 gm bw. A small incision was then made in the skin along the midline of the abdomen, and a single injection of 0.1 mL containing $1 \times 10^6$ cells was injected into the #4 mammary gland fat pad (1 tumor/mouse). The incision was then closed, animals allowed to recover, and then returned to their treatment group cages. Approximately 40 days after transplantation, tumors became palpable at an average size of approximately 5 mm in diameter. Tumor bearing mice were then divided into the following treatment groups: 1) Vehicle-treated controls; and 2) 0.5 mg of Compound 30 in 0.1 mL of propylene glycol/DMSO (1:1) vehicle. Treatments were administered daily by tail vein injection throughout the entire 14 day experimental period. Tumor size and body weighs were recorded every other day. Average tumor diameter for each palpable tumor was determined using the mean of the 2 largest perpendicular diameters as measured with vernier calipers. Tumor volume was determined using the equation:

$$\text{Volume} = \text{Length (cm)} \times \text{Width}^2 \text{ (cm)}/2 \text{ or } V = L \times W^2/2$$

Figure 36:
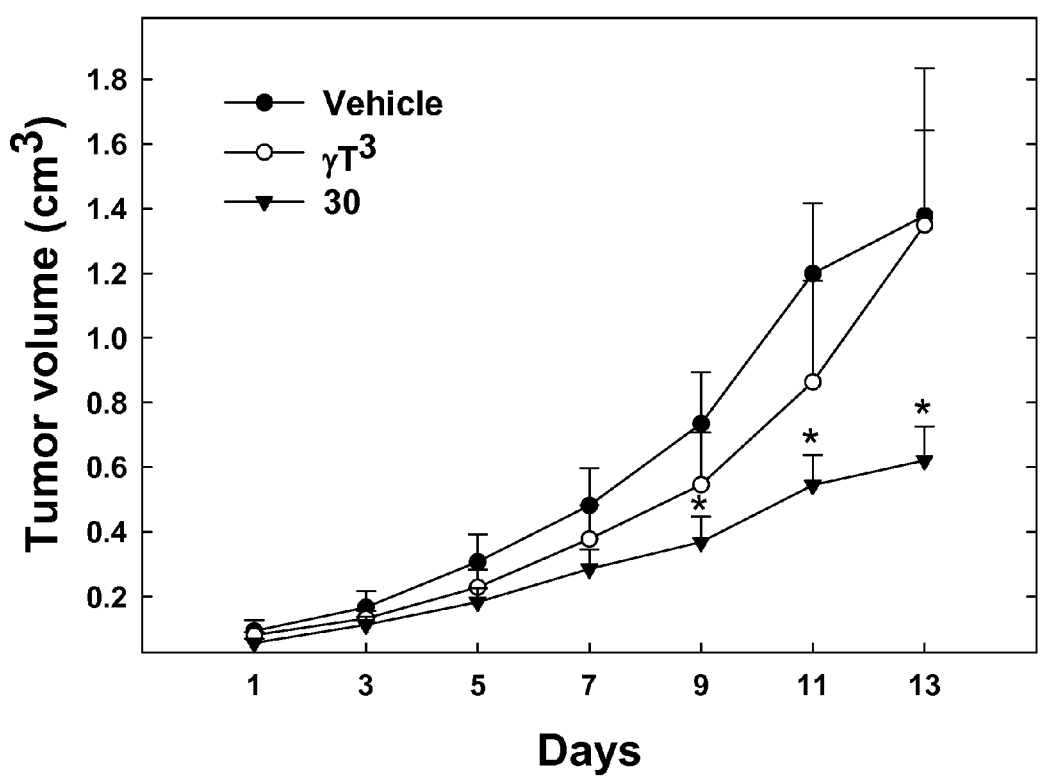
FIG. 36 shows the effect of Compound 30 on +SA mammary tumor growth in syngeneic BALB/c mice.
Figure 39:
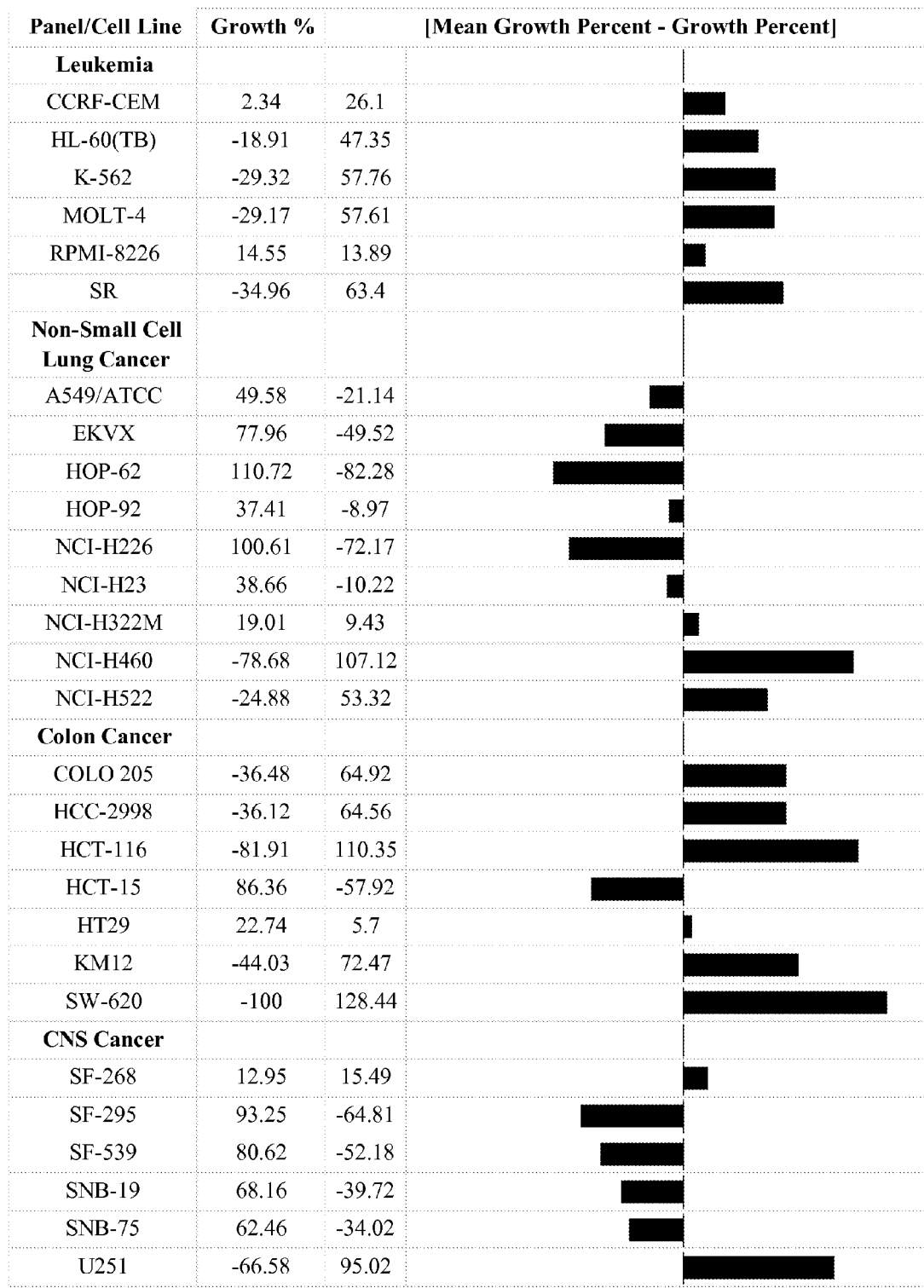
Figure 43:
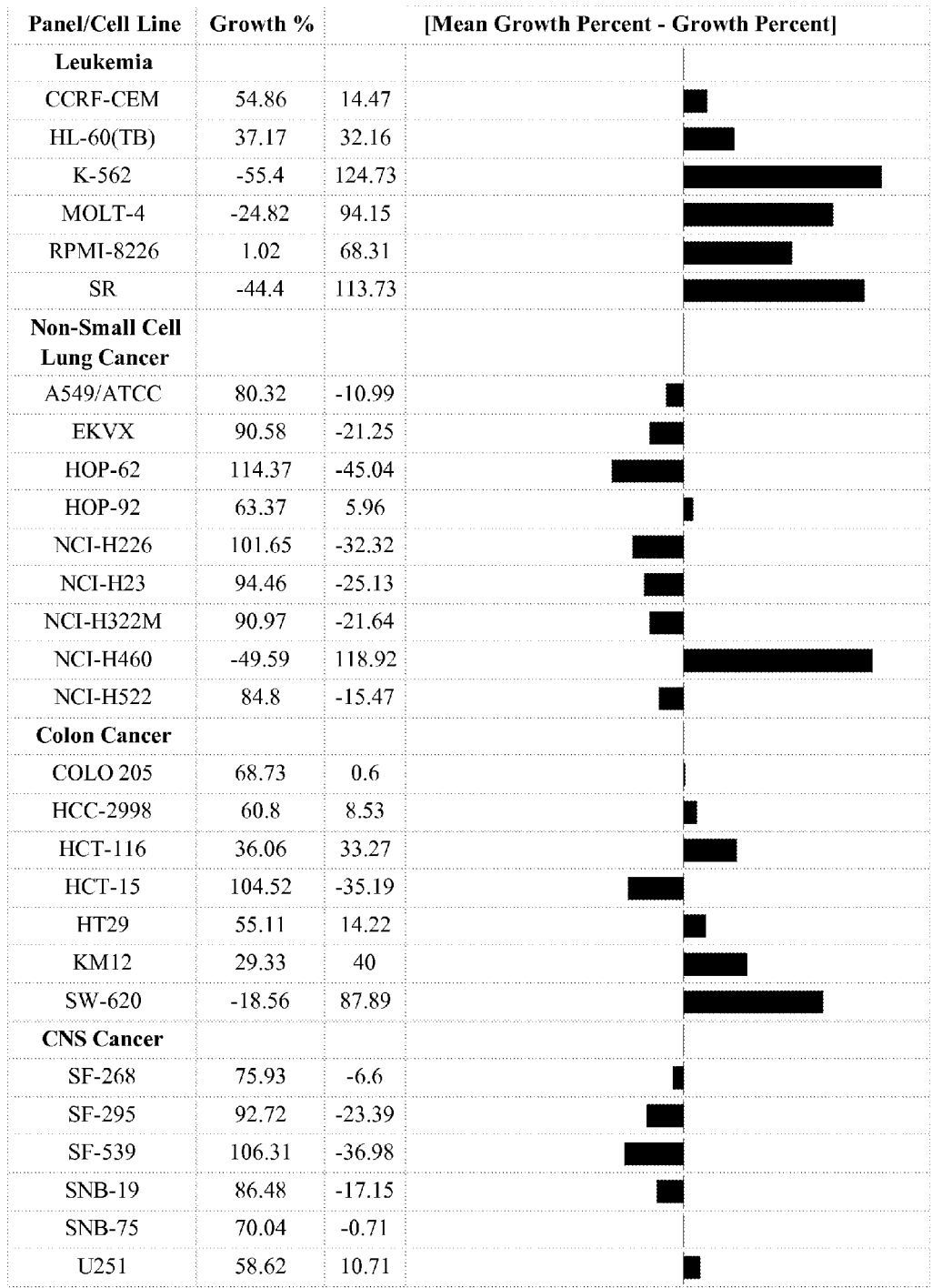
Figure 45:
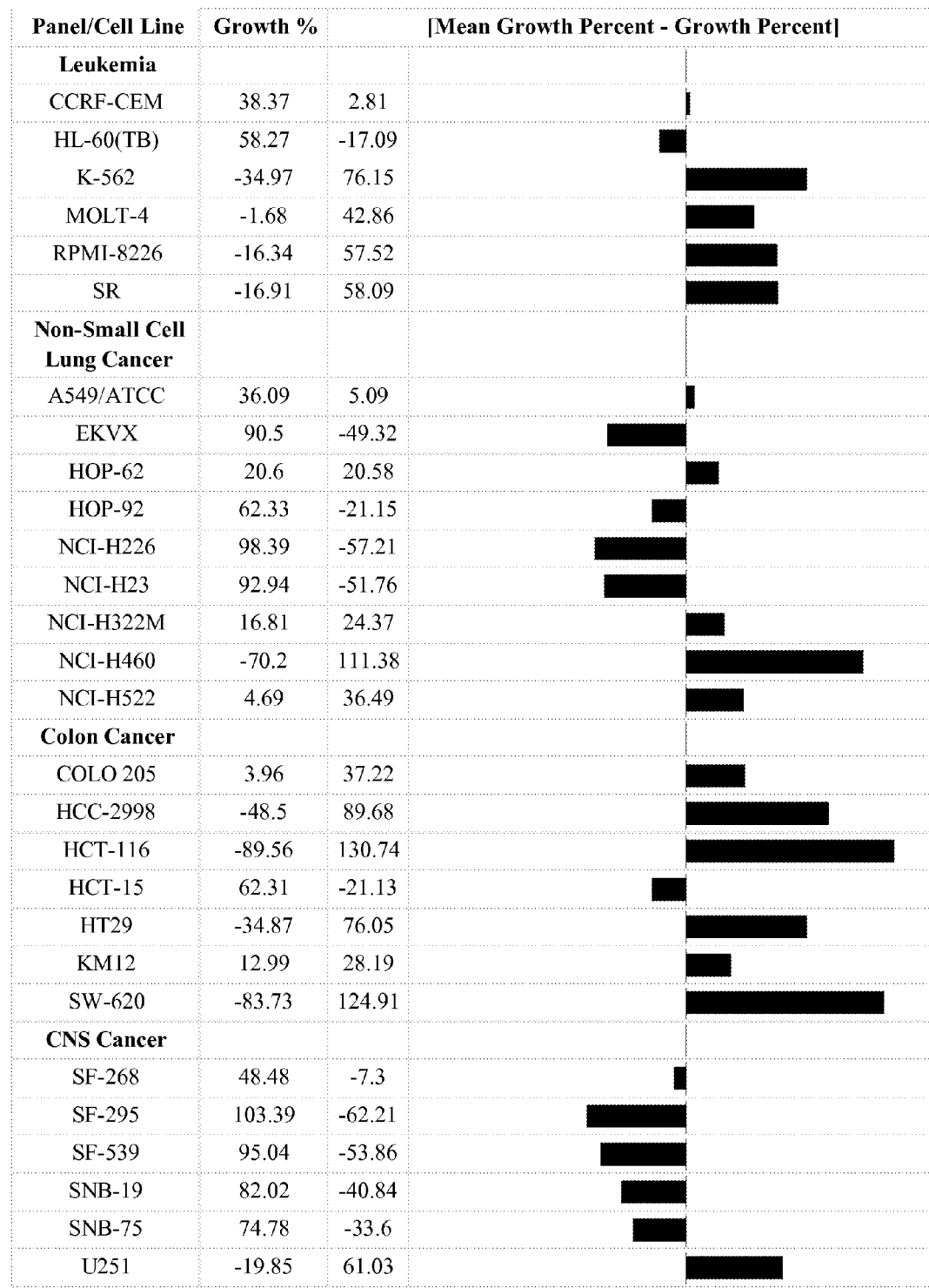
Figure 46:
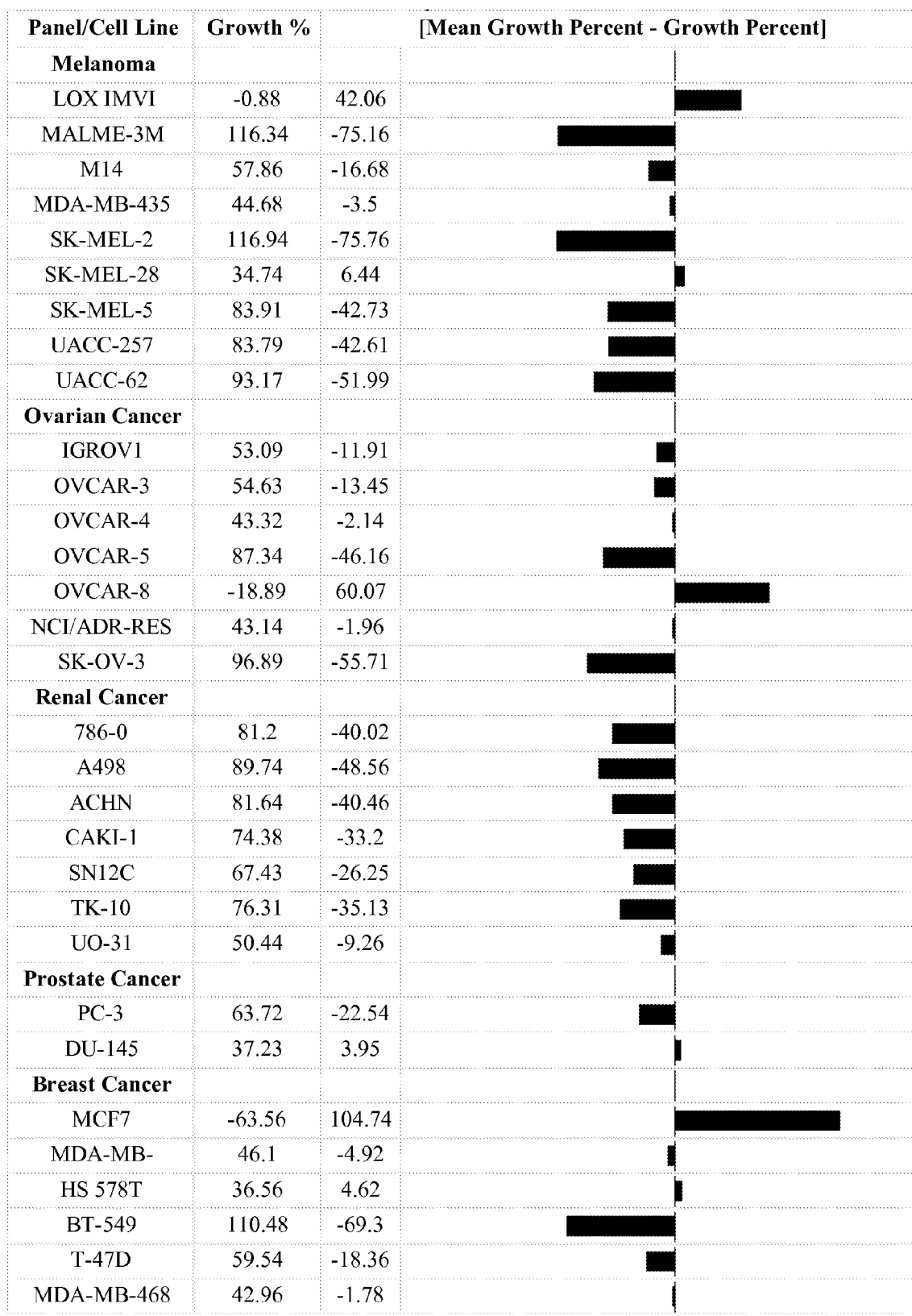
Figure 49:
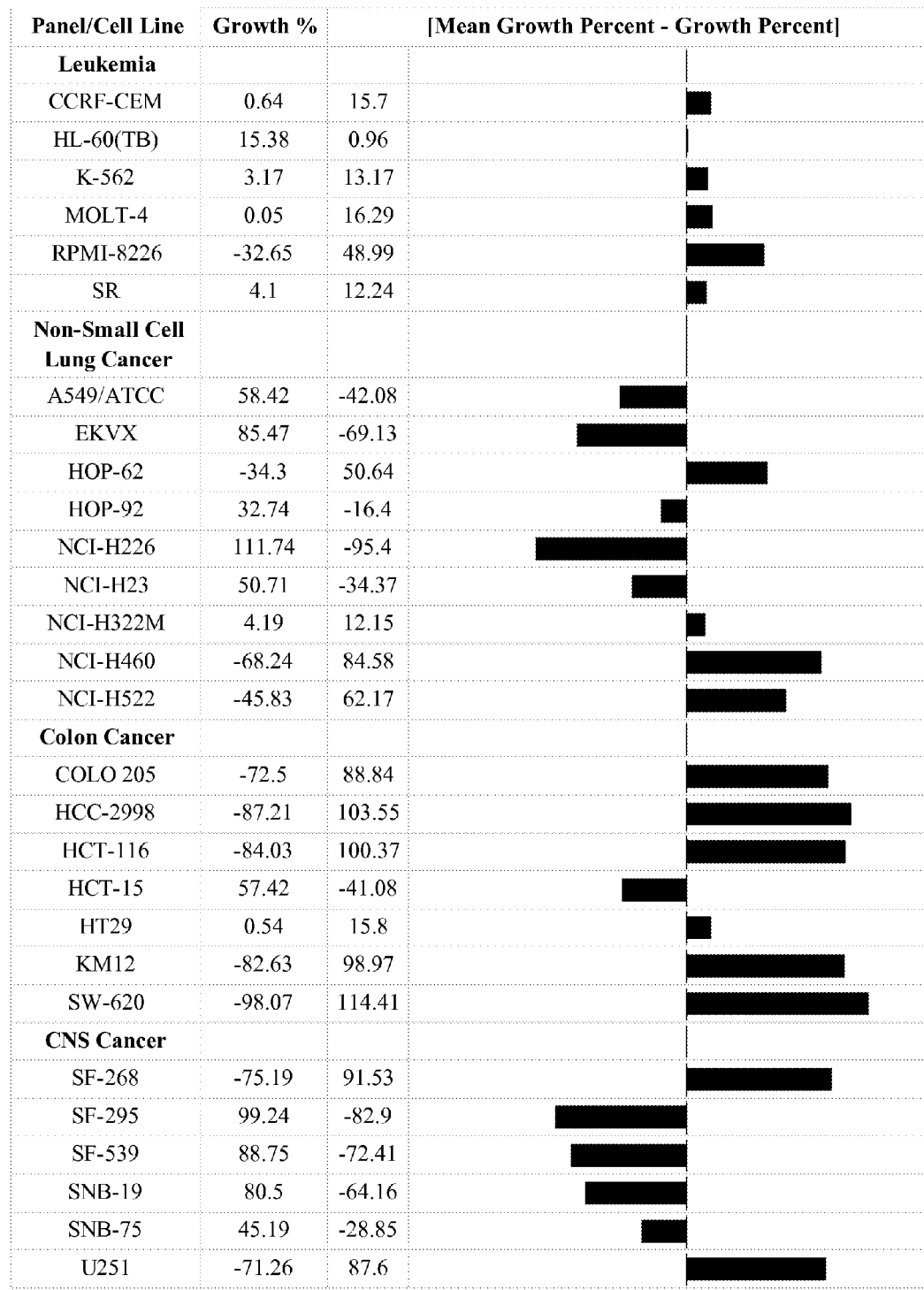
Figure 54:
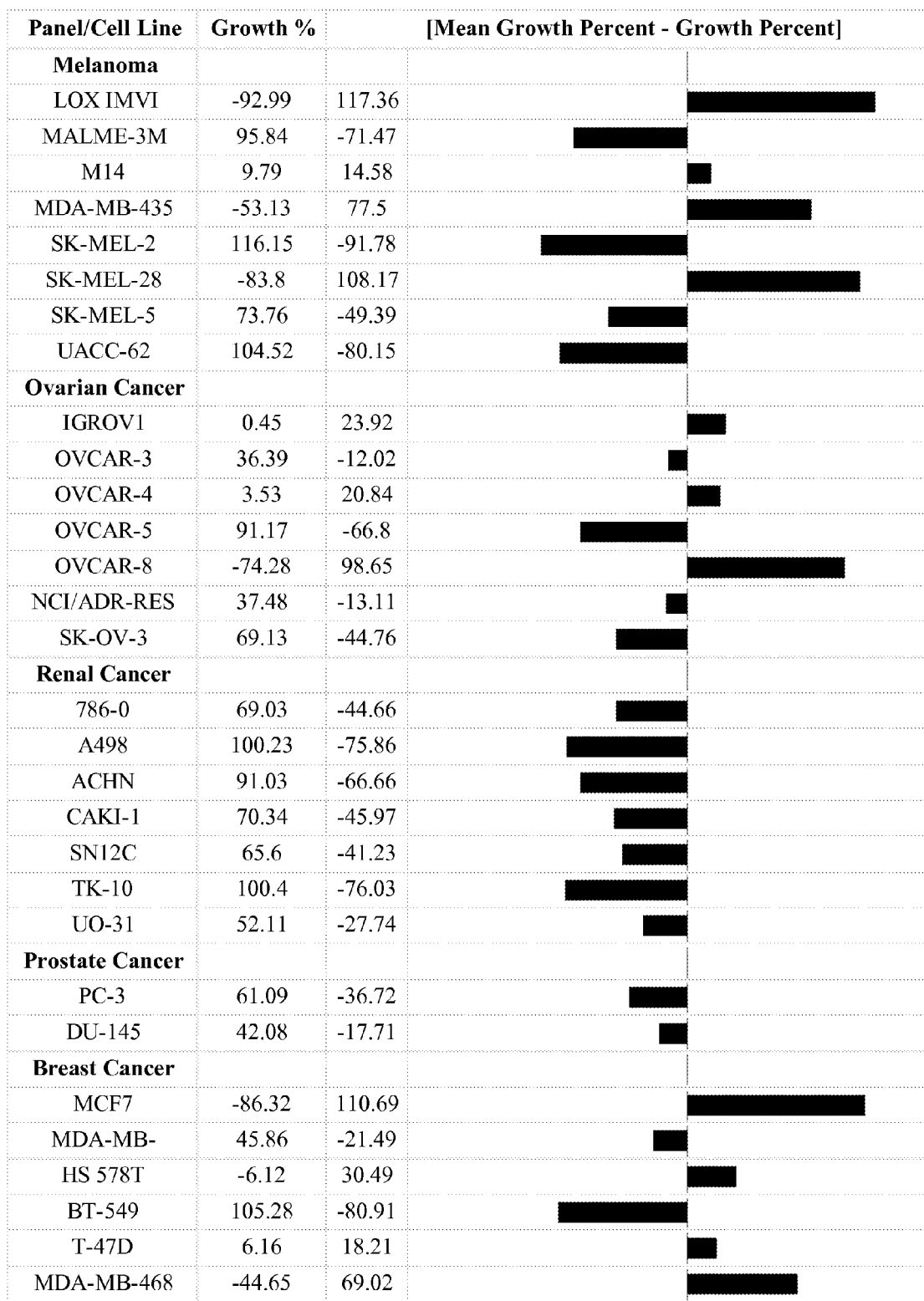
Figure 56:
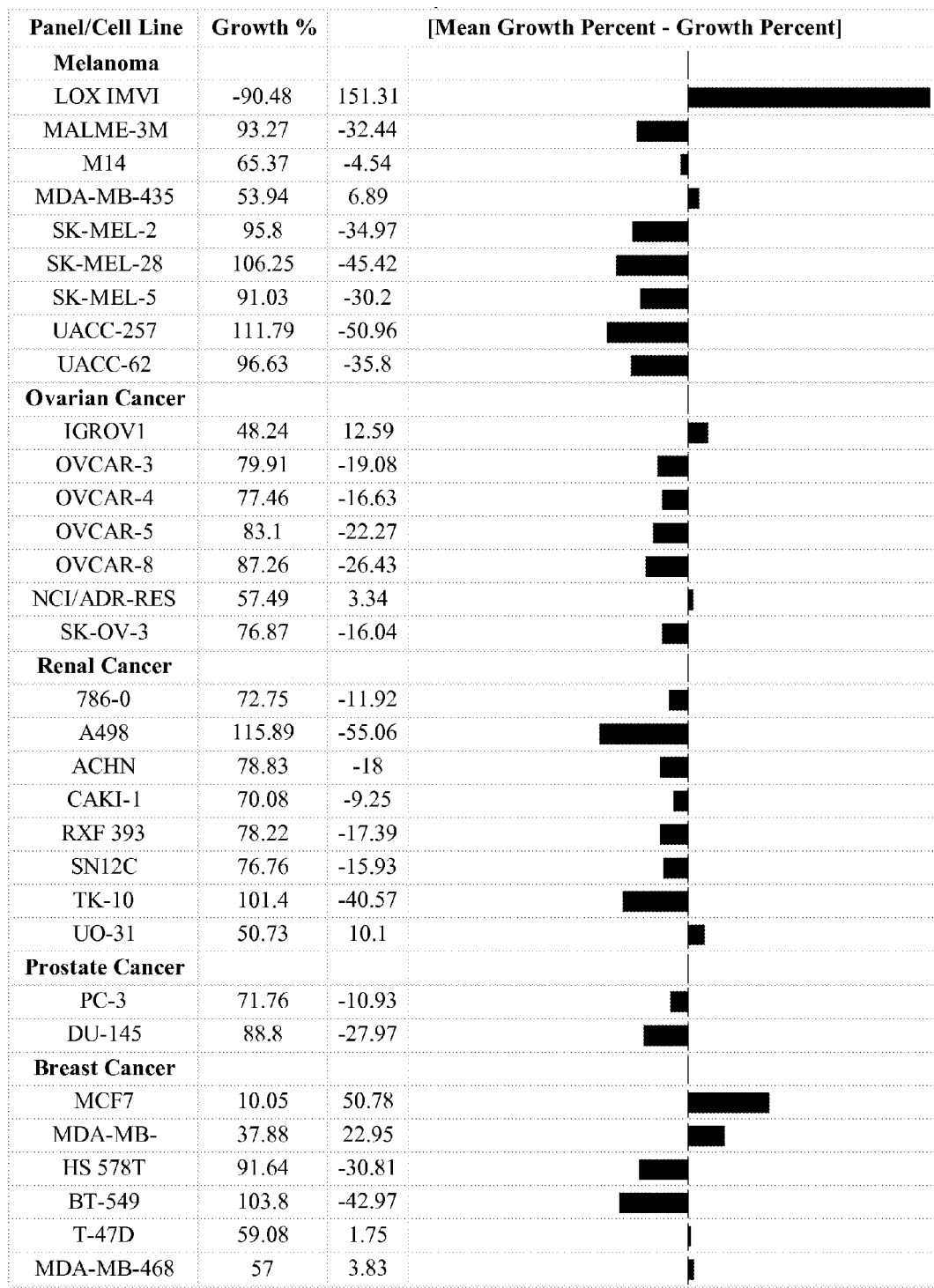
Figure 57:
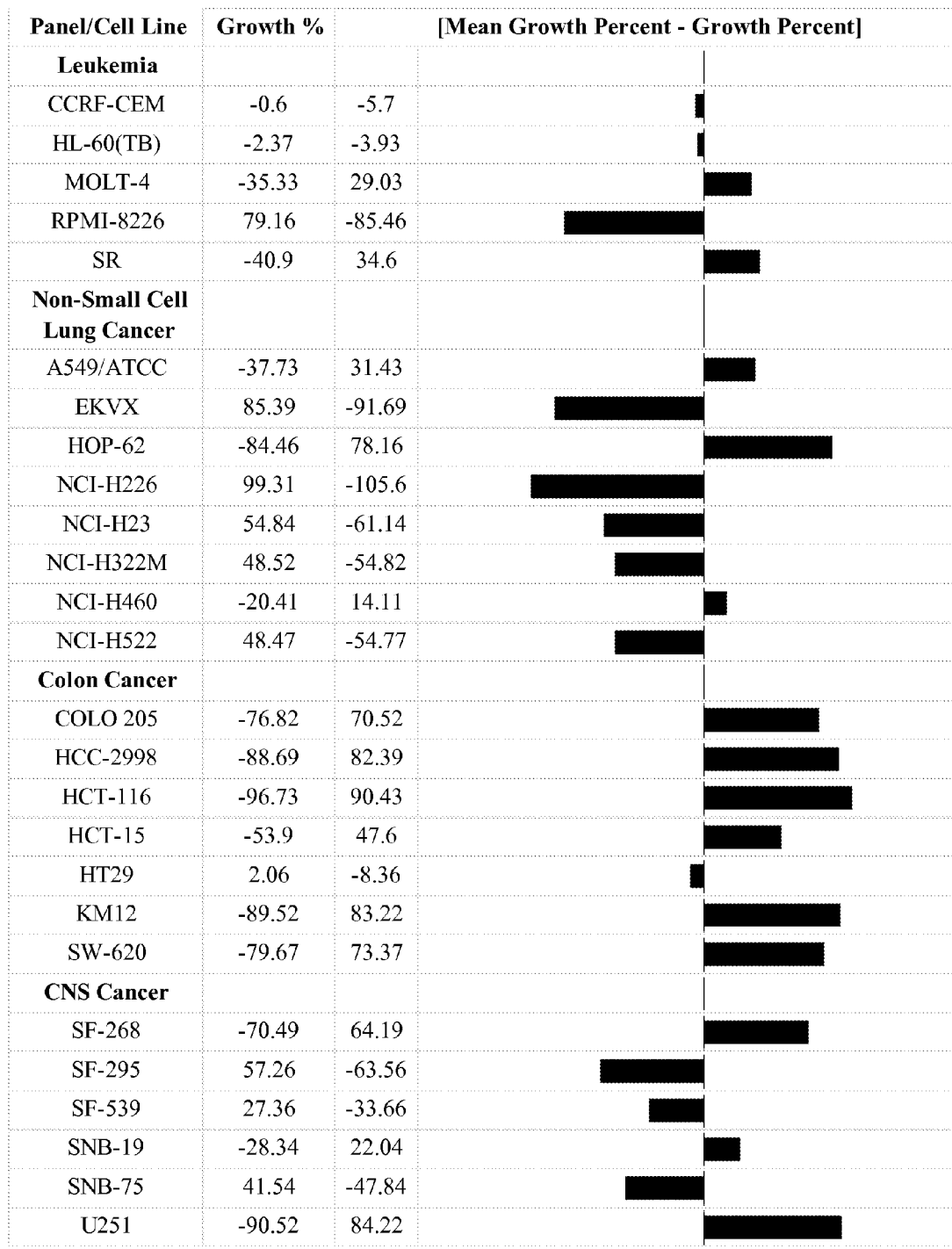
Figure 58:
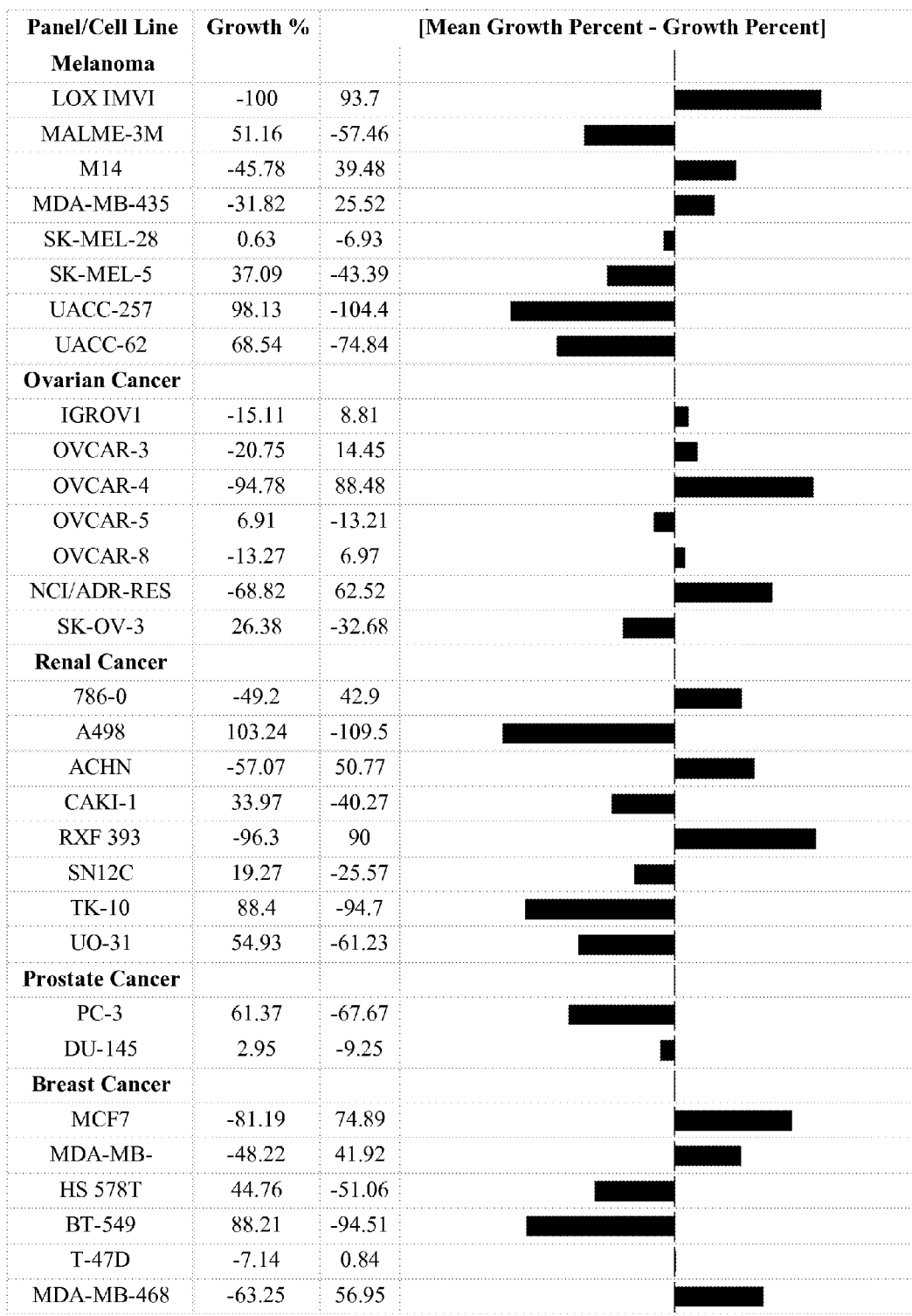
Figure 59:
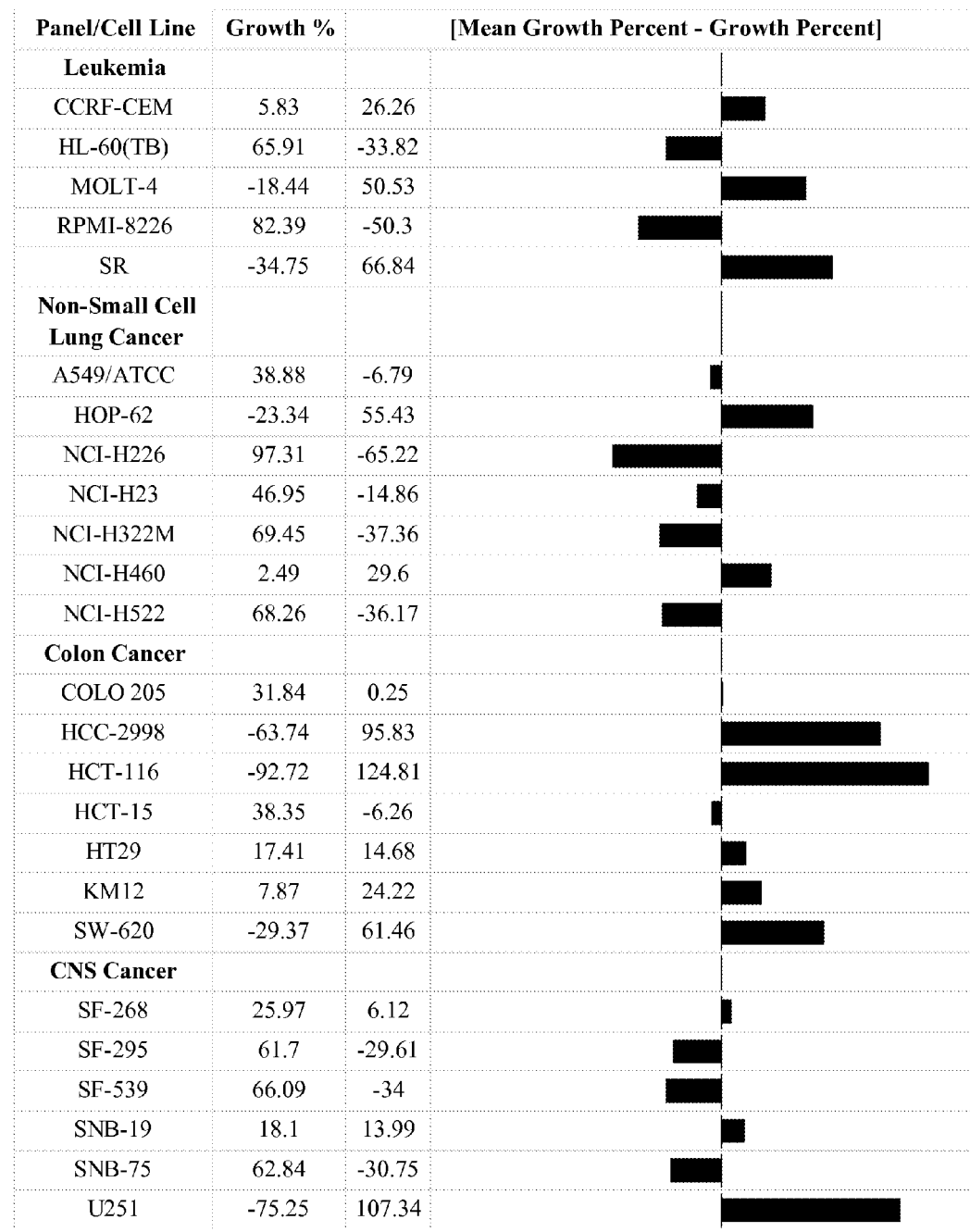
Figure 60:
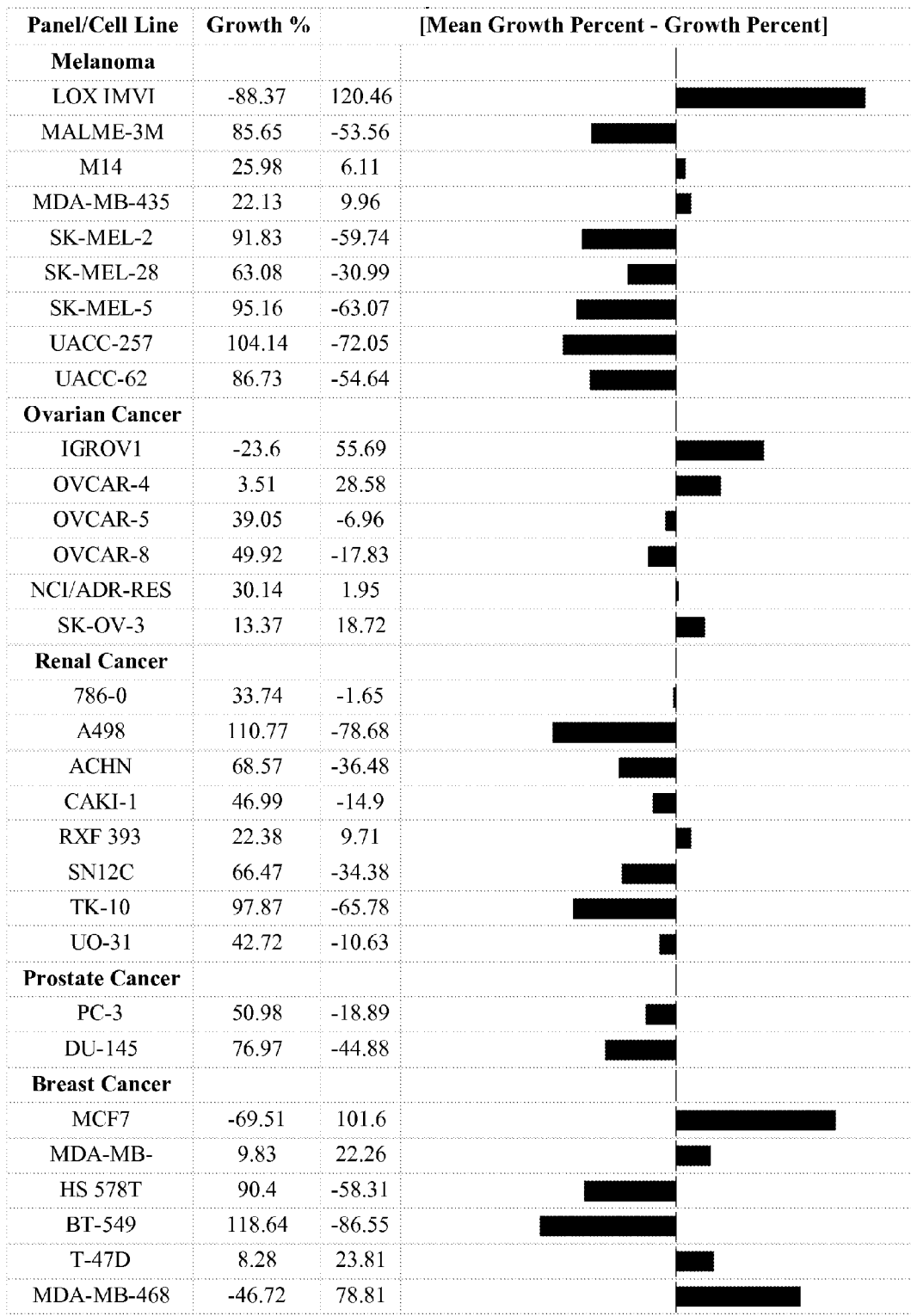
Figure 63:
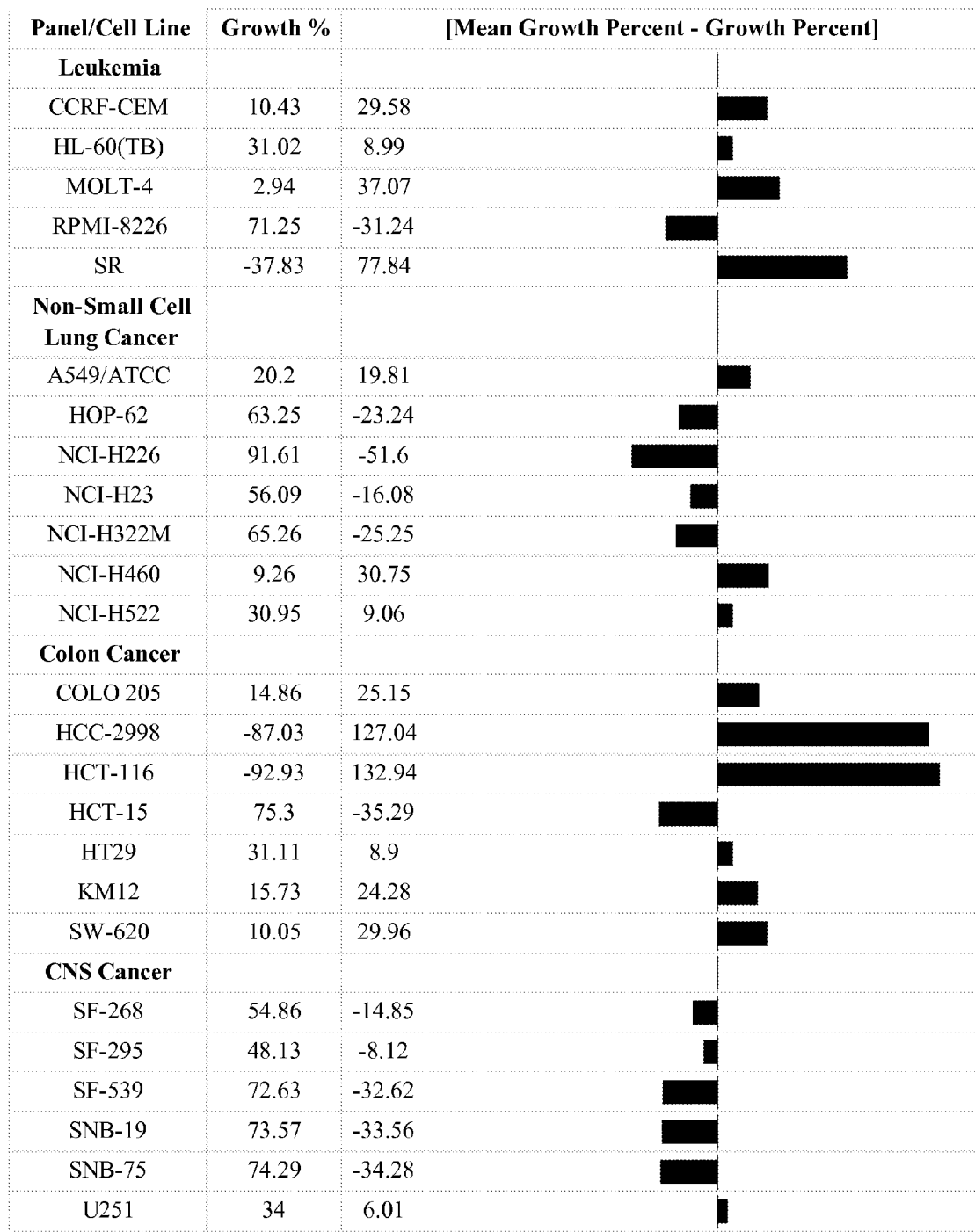
Figure 67:
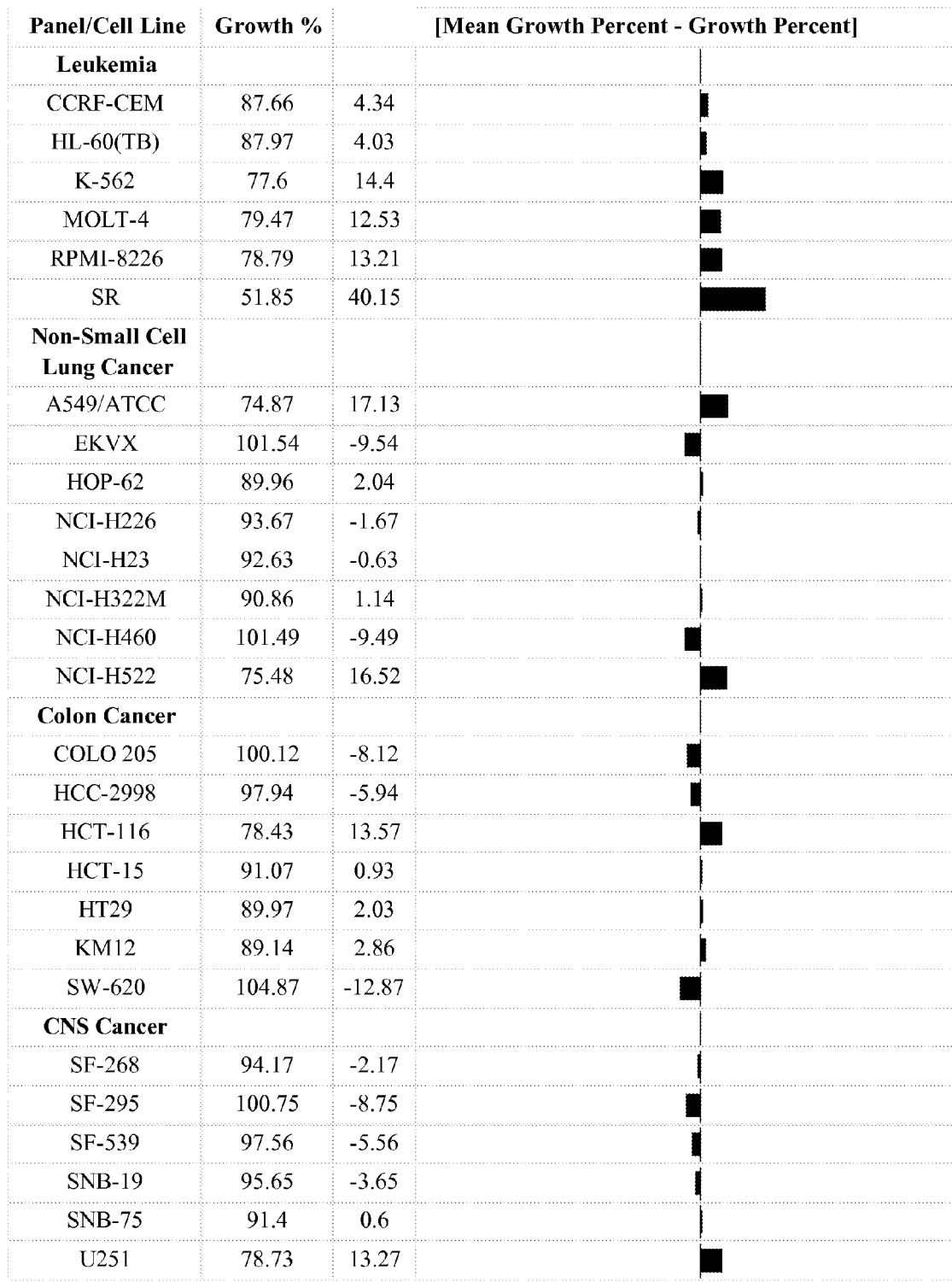

The effects of daily intravenous treatment with 0.5 mg of Compound 30 or 0.5 mg of γ-tocotrienol ($\gamma T^3$) dissolved in 0.1 mL propylene glycol on +SA mammary tumor growth in syngeneic BALB/c mice is shown in FIG. 36 throughout a 14-day experimental period. Palpable +SA mammary tumors started to appear in all groups approximately 40 days following tumor cell injection into the #4 mammary gland fat pad. In a vehicle-treated control group, measurable tumors continued to grow throughout the 14 day treatment period. In contrast, +SA mammary tumors in animals receiving 0.5 mg/day of Compound 30 grew at a significantly slower rate, as compared to tumors in the vehicle-treated controlled group. Body weights did not significantly differ among the different treatment groups at any time during the 14-day treatment experimental period. FIG. 36 shows the effect of Compound 30 on +SA mammary tumor growth in syngeneic BALB/c mice.

Example 7

Screening Compounds Against Cell Lines

Compounds selected from Compounds 3-44 were provided to the National Cancer Institute for in vitro screening against 60-human cell lines for their ability to inhibit the growth of tumor cells in a full panel representing nine different organs (blood, lung, colon, CNS, skin, ovary, kidney, prostate, and breast). The compounds were tested at a single concentration of 10 μM, and the percentages of growth inhibitions over the sixty tested cell lines were determined. Compounds showing the highest activity were chosen for secondary assays using five different compound concentrations.

The human tumor cell lines of the cancer screening panel were grown in RPMI 1640 medium containing 5% fetal bovine serum and 2 mM L-glutamine. For a typical screening experiment, cells are inoculated into 96 well microtiter plates in 100 μL at plating densities ranging from 5000 to 40,000 cells/well depending on the doubling time of individual cell lines. After cell inoculation, the microtiter plates are incubated at 37° C., 5% $CO_2$, 95% air and 100% relative humidity for 24 hours prior to addition of experimental drugs. After 24 hours, two plates of each cell line are fixed in situ with Trichloroacetic acid ("TCA"), to represent a measurement of the cell population for each cell line at the time of drug addition. Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 ng/mL gentamicin. An aliquot of 100 μL of this drug dilution is added to the appropriate microtiter wells already containing 100 μL of medium, resulting in the required final drug concentrations. Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 μL of cold 50% (w/v) TCA (final concentration, 10% TCA) and incubated for 60 min at 4° C. The supernatant is discarded, and the plates are washed five times with tap water and air dried. Sulforhodamine B (SRB) solution (100 μL) at 0.4% (w/v) in 1% acetic acid is added to each well, and plates are incubated for 10 min at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μL of 80% TCA (final concentration, 16% TCA). FIGS. 37-74 indicate the growth inhibition effects of selected Compounds against a variety of cell lines based on the above described testing configuration. FIGS. 37-74 present the Growth percent for a given compound against the cell lines and both values and a bar chart of the difference between the mean growth percent and the growth percent which is an indication of the selectivity of the compound for that particular cell line.

Example 8

Screening Compounds Against Cell Lines

FIGS. 75-100 indicate the calculated $GI_{50}$, TGI, and $LC_{50}$ molar concentration values for selected compounds based on testing of the compounds at 0.01 μM, 0.1 μM, 1.0 μM, and 10.0 μM concentrations against a variety of cell lines. Testing procedures were conducted by the National Cancer Institute utilizing methods comparable to those of Example 7.

Figure 101:
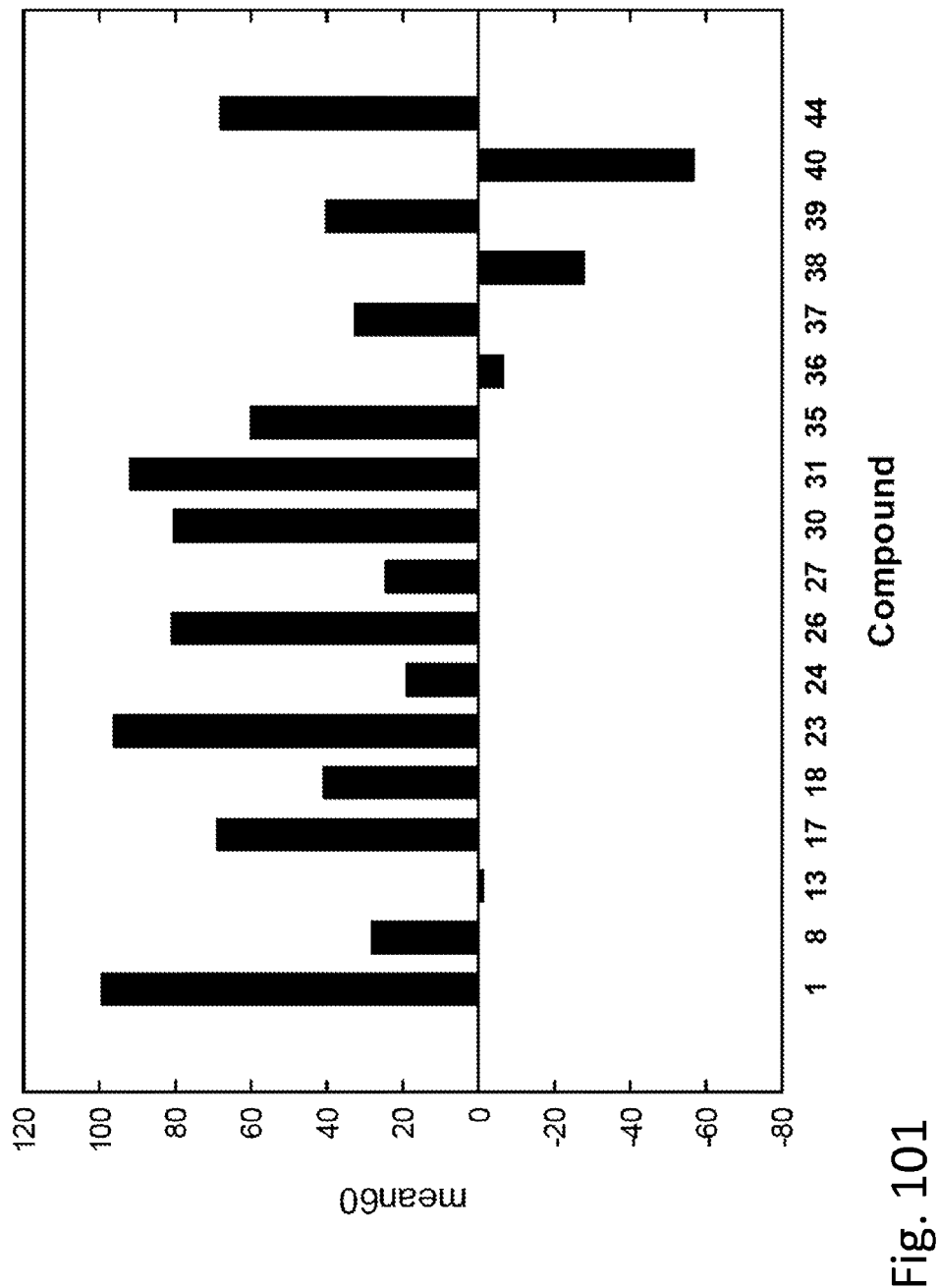
FIG. 101 shows the mean percent growth activity of Compounds 1, 8, 13, 17, 18, 23, 24, 26, 27, 30, 31, 35-40, and 44 across 60 cell lines.
Figure 102:
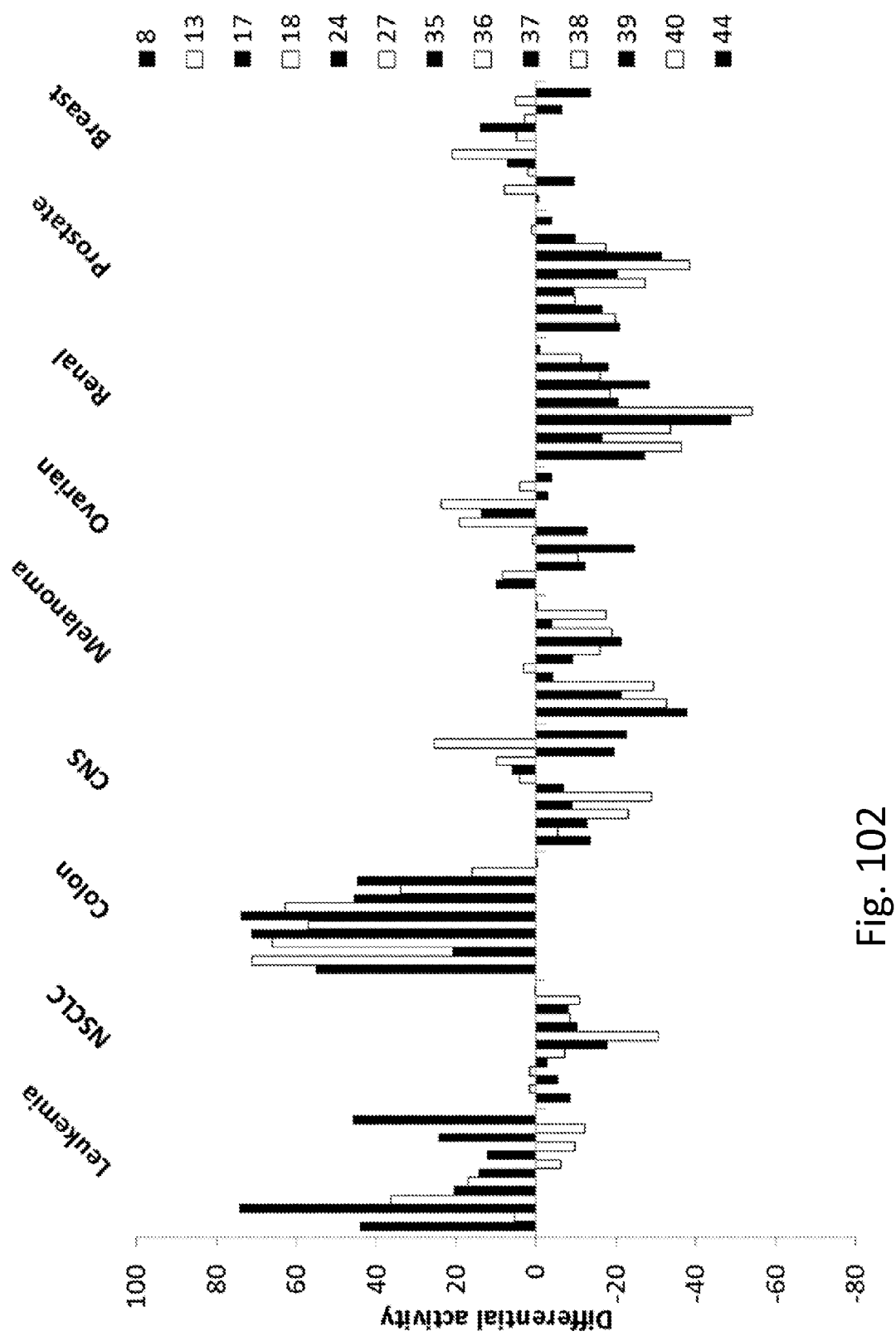
FIG. 102 shows the selectivity pattern of tocotrienol analogs on the cell lines belonging to different tissues.

Compounds 13, 36, 38, and 40 were lethal to the cells at 10 μM dose, showing negative mean percent growth values across all 60 cell lines (mean 60), while 1 was inactive. FIG. 101 shows the mean percent growth activity of Compounds 1, 8, 13, 17, 18, 23, 24, 26, 27, 30, 31, 35-40, and 44 across all the 60 cell lines (mean 60) with negative values indicating cytotoxicity. Mean percent growth values showed that the oxazine ring is an important pharmacophore for the shown activity since the Mannich bases without the oxazine ring, Compounds 30 and 31, showed activity comparable to the activity of Compound 1. The mean percent growth decreased by increasing the length of the R' as R' is shown in FIG. 21 from 4-carbons, Compound 36, to 6-carbons, Compound 38, to 8-carbons, Compound 40. However, increasing the length of the R' substituent of FIG. 21 to a length of 12-carbons, led to reducing the activity and increasing the mean percent growth value. This may indicate that the optimal length of the R' substituent for the best activity is at or near 8-carbons. Comparison of the mean percent growth values for γ- and δ-isomers substituents indicate that the oxazine analogs of Compound 2 (δ-isomer) were more cytotoxic or growth inhibitors than the corresponding Compound 1 analogs. Representing the data in the form of mean graphs, in which the percent growth of each cell line is subtracted from the mean percent growth, enables the detection of the differential growth inhibition activity of the compound on different tumor tissues and cell lines. Tocotrienol analogs showed selective growth inhibition of blood and colon malignant cell lines. FIG. 102 shows the selectivity pattern of tocotrienol analogs on the cell lines belonging to different tissues. The selectivity is calculated by subtracting the mean growth percent of each tissue from the mean 60. A positive value indicates selectivity of the compound for the tissue. Compounds 8, 17, 38, and 40 inhibited the growth of leukemia and colon cancer cell lines at nanomolar $GI_{50}$ values. In FIG. 102 each compound is presented from left to right in the following order: Compound 8, Compound 13, Compound 17, Compound 18, Compound 24, Compound 27, Compound 35, Compound 36, Compound 37, Compound 38, Compound 39, Compound 40, and Compound 44 with that pattern repeating for each cancer type.

All reagents and chemicals were purchased from Sigma-Aldrich Chemical Co. and VWR International. Tocotrienol-rich fraction 50 g (Palm TRF 70%, low in tocopherol from First Tech International Ltd., Hong Kong) was fractionated on Si gel 60 using n-hexane/ethyl acetate (gradient elution). Optical rotations were measured on a Rudolph Research Analytical Autopol III polarimeter. IR spectra were recorded on a Varian 800 FT-IR spectrophotometer. The $^1$H- and $^{13}$C-NMR spectra were recorded in $CDCl_3$, using TMS as an internal standard, on a JEOL Eclipse-400 NMR spectrometer, operating at 400 MHz for $^1$H and 100 MHz for $^{13}$C. The HREIMS experiments were conducted at Louisiana State University on a 6200-TOF LCMS (Agilent) equipped with multimode source (mixed source that can ionized the compounds alternatively by ESI and APCI). The ESIMS was conducted using 3200 Q-trap LC/MS/MS system (Applied Biosystems, Foster City, Calif.) using Analyst version 1.4.1 software (MDS Sciex; Toronto, Canada). The analytes were ionized using electro-spray ionization (ESI) interface operated in the positive mode. The analysis was conducted using Q1 scan and mass scan range was m/z 50-500 (0.15 s/scan). TLC analysis was carried on precoated Si gel 60 $F_{254}$ 500 µm TLC plates (EMD Chemicals), using variable proportions of n-hexane-ethyl acetate and ethyl acetate-methanol-water as a mobile phase. Vanillin in concentrated $H_2SO_4$ (1% w/v) was used as visualizing reagent. For column chromatography, Si gel 60 (Natland, 63-200 µm) was used.

Statistical differences between treatment groups were determined using analysis of variance, followed by Duncan's multiple range test. A difference of p<0.05 was considered to be significant, as compared to the vehicle-treated control group.

The compositions disclosed herein may be delivered intravenously, intraperitoneally, subcutaneously, intramuscularly, ocularly, orally, transdermally, topically, by inhalation or by other suitable means.

Individual compositions disclosed herein may be used in the treatment of a cancer selected from leukemia, non-small cell lung cancer, colon cancer, central nervous system cancer, melanoma, ovarian cancer, renal cancer, prostate cancer, and breast cancer. The compositions disclosed herein may be used in the treatment of a cancer selected from one of the cell lines disclosed. For each instance in which this disclosure shows that one of the compounds disclosed herein substantially inhibited the growth of a particular cell line disclosed herein, that compound may be used to treat cell lines that are substantially similar to the cell line for which the growth was inhibited.

As used herein, the term "therapeutic amount" indicates an amount which is sufficient to effect beneficial or desired clinical results. Non-limiting examples of these types of results include significant slowing or stopping of the proliferation of cancer cells in a mammal and decreasing the number of live cancer cells in a patient. As used herein, the term "pharmaceutically acceptable salt" refers to a salt prepared from any one or multiple non-toxic acid(s) or base(s), including both organic and inorganic acids and bases that are suitable for use in contact with living animal or human tissue without causing adverse physiological responses.

Any and all reference to patents, documents and other writings contained herein shall not be construed as an admission as to their status with respect to being or not being prior art. It is understood that the array of features and embodiments taught herein may be combined and rearranged in a large number of additional combinations not directly disclosed, as will be apparent to one having skill in the art and that various embodiments of the invention may have less than all of the benefits and advantages disclosed herein.

There are, of course, other alternate embodiments which are obvious from the foregoing descriptions, which are intended to be included within the scope of the invention, as defined by the following claims.

We claim:

1. A composition of matter comprising a compound selected from:
   2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol;
   (R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine;
   (R)-5-((3,4-dimethoxyphenethylamino)methyl)-2,7,8-trimethyl-2-((3E,7E)-4,8,12-trimethyltrideca-3,7,11-trienyl)chroman-6-ol;
   (R)-5-((4-hydroxyphenethylamino)methyl)-2,7,8-trimethyl-2-((3E,7E)-4,8,12-trimethyltrideca-3,7,11-trienyl)chroman-6-ol;
   (R)-5-(hydroxymethyl)-2,7,8-trimethyl-2-((3E,7E)-4,8,12-trimethyltrideca-3,7,11-trienyl)chroman-6-ol;
   (R)-5-(hydroxymethyl)-2,8-dimethyl-2-((3E,7E)-4,8,12-trimethyltrideca-3,7,11-trienyl)chroman-6-ol; and
   (R)-7-(hydroxymethyl)-2,8-dimethyl-2-((3E,7E)-4,8,12-trimethyltrideca-3,7,11-trienyl)chroman-6-ol.

2. The composition of matter of claim 1 wherein the compound is 2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol.

3. The composition of matter of claim 1 wherein the compound is (R)-3-(3,4-dimethoxyphenethyl)-5,7-dimethyl-7-

((3E,7E)-4,8,12-trimethyltrideca-3,7,11-trienyl)-2,3,4,7,8,9-hexahydrochromeno[7,6-e][1,3]oxazine.

4. The composition of matter of claim 1 wherein the compound is (R)-5-((3,4-dimethoxyphenethylamino)methyl)-2,7,8-trimethyl-2-((3E,7E)-4,8,12-trimethyltrideca-3,7,11-trienyl)chroman-6-ol.

5. The composition of matter of claim 1 wherein the compound is (R)-5-((4-hydroxyphenethylamino)methyl)-2,7,8-trimethyl-2-((3E,7E)-4,8,12-trimethyltrideca-3,7,11-trienyl)chroman-6-ol.

6. The composition of matter of claim 1 wherein the compound is (R)-5-(hydroxymethyl)-2,7,8-trimethyl-2-((3E,7E)-4,8,12-trimethyltrideca-3,7,11-trienyl)chroman-6-ol.

7. The composition of matter of claim 1 wherein the compound is (R)-5-(hydroxymethyl)-2,8-dimethyl-2-((3E,7E)-4,8,12-trimethyltrideca-3,7,11-trienyl)chroman-6-ol.

8. The composition of matter of claim 1 wherein the compound is (R)-7-(hydroxymethyl)-2,8-dimethyl-2-((3E,7E)-4,8,12-trimethyltrideca-3,7,11-trienyl)chroman-6-ol.

9. A composition of matter comprising a pharmaceutically acceptable salt of a compound selected from:
- 2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol;
- (R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine;
- (R)-5-((3,4-dimethoxyphenethylamino)methyl)-2,7,8-trimethyl-2-((3E,7E)-4,8,12-trimethyltrideca-3,7,11-trienyl)chroman-6-ol;
- (R)-5-((4-hydroxyphenethylamino)methyl)-2,7,8-trimethyl-2-((3E,7E)-4,8,12-trimethyltrideca-3,7,11-trienyl)chroman-6-ol;
- (R)-5-(hydroxymethyl)-2,7,8-trimethyl-2-((3E,7E)-4,8,12-trimethyltrideca-3,7,11-trienyl)chroman-6-ol;
- (R)-5-(hydroxymethyl)-2,8-dimethyl-2-((3E,7E)-4,8,12-trimethyltrideca-3,7,11-trienyl)chroman-6-ol; and
- (R)-7-(hydroxymethyl)-2,8-dimethyl-2-((3E,7E)-4,8,12-trimethyltrideca-3,7,11-trienyl)chroman-6-ol.

10. The composition of matter of claim 9 wherein the compound is 2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol.

11. The composition of matter of claim 9 wherein the compound is (R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine.

12. The composition of matter of claim 9 wherein the compound is (R)-5-((3,4-dimethoxyphenethylamino)methyl)-2,7,8-trimethyl-2-((3E,7E)-4,8,12-trimethyltrideca-3,7,11-trienyl)chroman-6-ol.

13. The composition of matter of claim 9 wherein the compound is (R)-5-((4-hydroxyphenethylamino)methyl)-2,7,8-trimethyl-2-((3E,7E)-4,8,12-trimethyltrideca-3,7,11-trienyl)chroman-6-ol.

14. The composition of matter of claim 9 wherein the compound is (R)-5-(hydroxymethyl)-2,7,8-trimethyl-2-((3E,7E)-4,8,12-trimethyltrideca-3,7,11-trienyl)chroman-6-ol.

15. The composition of matter of claim 9 wherein the compound is (R)-5-(hydroxymethyl)-2,8-dimethyl-2-((3E,7E)-4,8,12-trimethyltrideca-3,7,11-trienyl)chroman-6-ol.

16. The composition of matter of claim 9 wherein the compound is (R)-7-(hydroxymethyl)-2,8-dimethyl-2-((3E,7E)-4,8,12-trimethyltrideca-3,7,11-trienyl)chroman-6-ol.

17. A composition of matter comprising a compound having the general formula:

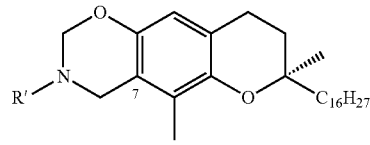

wherein $C_{16}H_{27}$ is

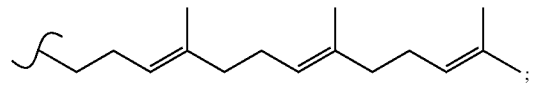

wherein R' is selected from

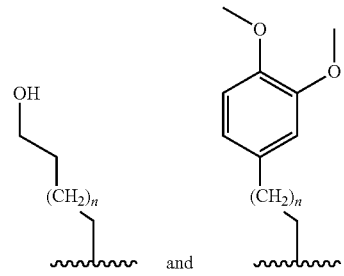

and wherein "n" is an integer selected from 1, 2, 3, 4, 5, 6, and 7.

18. A method of treating a form of cancer comprising administering to a mammalian patient in need of said treatment either a therapeutic amount of a compound or a therapeutic amount of a pharmaceutically acceptable salt of said compound, wherein said compound is selected from:
- 2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol;
- (R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine;
- (R)-5-((3,4-dimethoxyphenethylamino)methyl)-2,7,8-trimethyl-2-((3E,7E)-4,8,12-trimethyltrideca-3,7,11-trienyl)chroman-6-ol;
- (R)-5-((4-hydroxyphenethylamino)methyl)-2,7,8-trimethyl-2-((3E,7E)-4,8,12-trimethyltrideca-3,7,11-trienyl)chroman-6-ol;
- (R)-5-(hydroxymethyl)-2,7,8-trimethyl-2-((3E,7E)-4,8,12-trimethyltrideca-3,7,11-trienyl)chroman-6-ol;
- (R)-5-(hydroxymethyl)-2,8-dimethyl-2-((3E,7E)-4,8,12-trimethyltrideca-3,7,11-trienyl)chroman-6-ol; and
- (R)-7-(hydroxymethyl)-2,8-dimethyl-2-((3E,7E)-4,8,12-trimethyltrideca-3,7,11-trienyl)chroman-6-ol.

19. A method of treating a form of cancer comprising exposing a mammalian cell to either a therapeutic amount of a compound or a therapeutic amount of a pharmaceutically acceptable salt of said compound, wherein said compound is selected from:
- 2-((R)-5,7-dimethyl-7-((3E,7E)-4,8,12-trimethyltrideca-3,7,11-trienyl)-8,9-dihydrochromeno[7,6-e][1,3]oxazin-3 (2H,4H,7H)-yl)ethanol;
- (R)-3-(3,4-dimethoxyphenethyl)-5,7-dimethyl-7-((3E,7E)-4,8,12-trimethyltrideca-3,7,11-trienyl)-2,3,4,7,8,9-hexahydrochromeno[7,6-e][1,3]oxazine;

(R)-5-((3,4-dimethoxyphenethylamino)methyl)-2,7,8-trimethyl-2-((3E,7E)-4,8,12-trimethyltrideca-3,7,11-trienyl)chroman-6-ol;

(R)-5-((4-hydroxyphenethylamino)methyl)-2,7,8-trimethyl-2-((3E,7E)-4,8,12-trimethyltrideca-3,7,11-trienyl)chroman-6-ol;

(R)-5-(hydroxymethyl)-2,7,8-trimethyl-2-((3E,7E)-4,8,12-trimethyltrideca-3,7,11-trienyl)chroman-6-ol;

(R)-5-(hydroxymethyl)-2,8-dimethyl-2-((3E,7E)-4,8,12-trimethyltrideca-3,7,11-trienyl)chroman-6-ol; and (R)-7-(hydroxymethyl)-2,8-dimethyl-2-((3E,7E)-4,8,12-trimethyltrideca-3,7,11-trienyl)chroman-6-ol.

* * * * *